United States Patent [19]

Breuer et al.

[11] Patent Number: 4,743,685

[45] Date of Patent: May 10, 1988

[54] 2-OXO-1-[[(SUBSTITUTED SULFONYL)AMINO]CARBONYL]AZETIDINES

[75] Inventors: Hermann Breuer, Schoenhofen; Uwe D. Treuner, Etterzhausen, both of Fed. Rep. of Germany; William H. Koster, Pennington; Robert Zahler, Princeton, both of N.J.

[73] Assignee: E. R. Squibb & Sons, Inc., Princeton, N.J.

[21] Appl. No.: 907,441

[22] Filed: Sep. 15, 1986

Related U.S. Application Data

[63] Continuation-in-part of Ser. No. 780,479, Sep. 26, 1985, abandoned.

[51] Int. Cl.$^4$ .................. C07D 401/12; C07D 401/14; C07D 417/14; A61K 31/425
[52] U.S. Cl. .................... 540/363; 540/357; 540/360; 540/364; 546/278; 546/296; 544/360
[58] Field of Search ................ 540/363, 364, 357, 360

[56] References Cited

U.S. PATENT DOCUMENTS 4,587,047 5/1986 Breuer et al. ........................ 540/355
4,670,553 6/1987 Breuer et al. ........................ 540/363

FOREIGN PATENT DOCUMENTS 0062876 10/1982 European Pat. Off. .

OTHER PUBLICATIONS

Squibb, Chem. Abs. 99, 175469f (1983).
Abstract No. 646 from 1984 ICAAC meeeting, "Antimicrobial Activities of 1-Carbacephem Compounds and their Structure-Activity Relationships", Mochida et al.
American Society for Microbiology, Program and Abstracts of the Twenty-Fifth Interscience Conference on Antimicrobial Agents and Chemotherapy, 1985, pp. 158 and 159.
American Society for Microbiology, Program and Abstracts of the Twenty-Sixth Interscience Conference on Antimicrobial Agents and Chemotherapy, 1986, pp. 253 and 254.

*Primary Examiner*—Mark L. Berch
*Attorney, Agent, or Firm*—Lawrence S. Levinson; Donald J. Barrack

[57] ABSTRACT

Antibacterial activity is exhibited by 2-azetidinones having a 3-acylamino substituent and having an activating group in the 1-position of the formula $$-\overset{O}{\underset{\|}{C}}-NH-SO_2-R \text{ wherein}$$

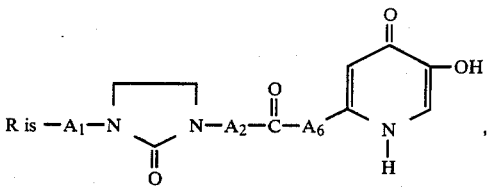

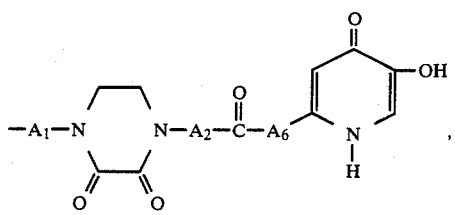

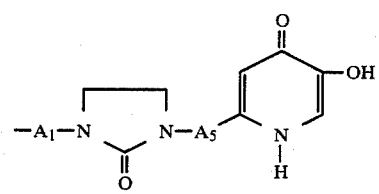

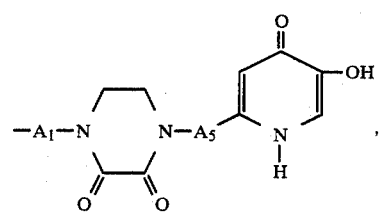

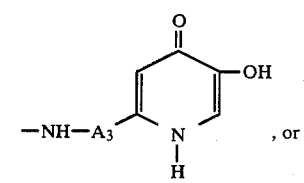

, or

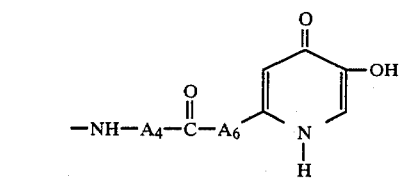

26 Claims, No Drawings

2-OXO-1-[[(SUBSTITUTED SULFONYL)AMINO]CARBONYL]AZETIDINES

This application is a continuation-in-part of copending U.S. patent application Ser. No. 780,479, filed Sept. 26, 1985 and now abandoned.

BRIEF DESCRIPTION OF THE INVENTION

Compounds having the formula

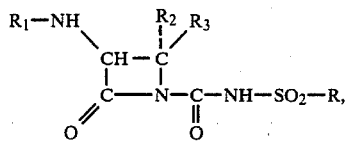

and pharmaceutically acceptable salts thereof, exhibit antibacterial activity. In formula I, and throughout the specification, the symbols are as defined below.

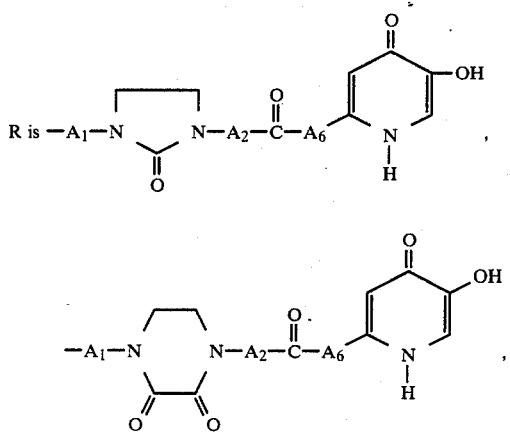

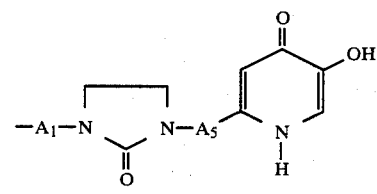

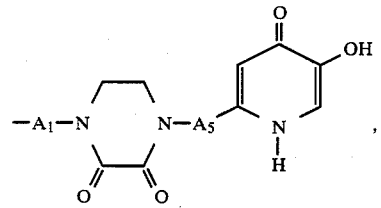

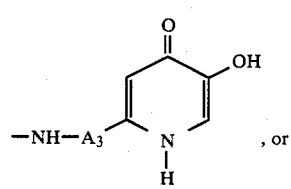, or

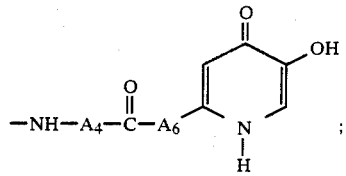

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

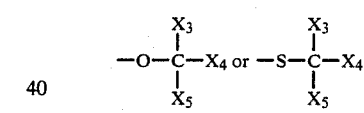

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl], $$-O-\underset{X_5}{\overset{X_3}{\underset{|}{C}}}-X_4 \text{ or } -S-\underset{X_5}{\overset{X_3}{\underset{|}{C}}}-X_4$$

wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

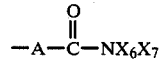

(substituted amino)carbonyl, or cyano (—C≡N)], or $$-A-\overset{O}{\underset{\|}{C}}-NX_6X_7$$

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino opr alkoxy, or $X_6$ and $X_7$ when taken together with the nitrogen atom to which they are attached form a 4, 5, 6 or 7-membered heterocycle];

$A_1$ is a single bond,

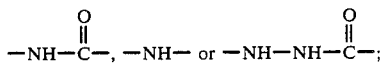

A₂ is a single bond, —NH—, —CH₂—CH₂—NH—, or

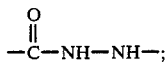

A₃ is —(CH₂)p— wherein p is 0 or 1,

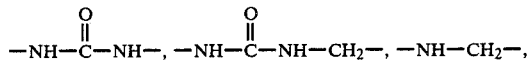

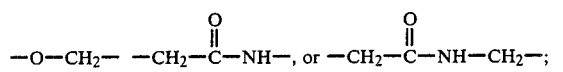

A₄ is —NH—, —(CH₂)$_p$—, —(CH₂)$_y$—NH—,

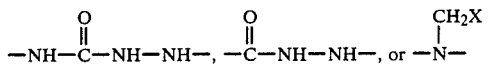

wherein X is hydrogen, carboxyl or carbamoyl and p is 0 or 1, and y is 2, 3 or 4;

A₅ is a single bond, —CH₂—, —NH—CH₂—, —N=CH—, or

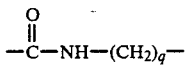

wherein q is 0 or 1;

A₆ is a single bond, —CH=CH— or —(CH₂)$_t$ wherein t is 1, 2, 3 or 4.

the above symbols (e.g., A₁, A₂, A₃, A₄, A₅ and A₆) are used to represent groups of multiple atoms. These groups are inserted in the structural formulas shown herein in the order in which they are presented (i.e., from left to right). For example, if R is

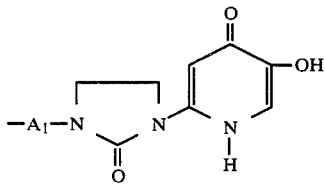

and A₁ is

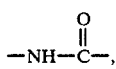

the R group would be

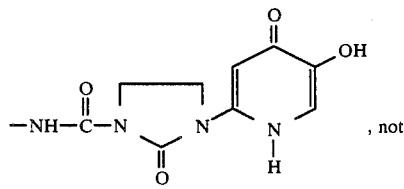

, not

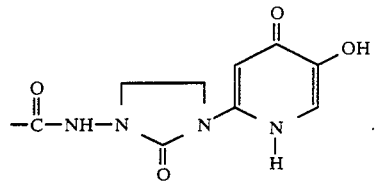

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one or more (preferably 1, 2 or 3) azido, amino (—NH₂), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "R$_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino ( 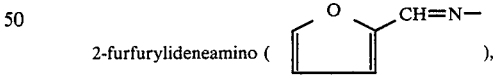 ), benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7- membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino (—$NH_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian patent No. 867,994, published Dec. 11, 1978, U.S. Pat. Nos. 4,152,432, issued May 1, 1979, 3,971,778, issued July 27, 1976, and 4,172,199, issued Oct. 23, 1979, and British patent No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexedienyl; or alkyl or alkenyl substituted with one or more halogen, cyano, nitro, amino, mercapto, alkylthio, or cyanomethylthio groups.

(b) Carbocycylic aromatic groups having the formula

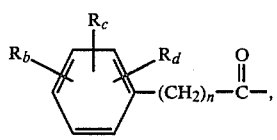

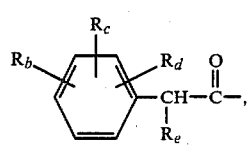

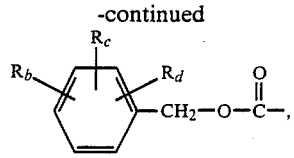

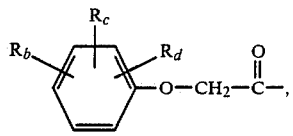

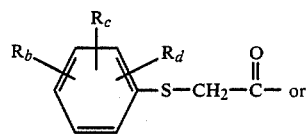

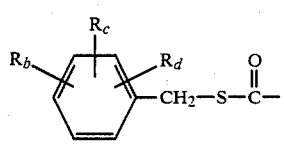

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl] thio.

Preferred carbocyclic aromatic acyl groups include those having the formula

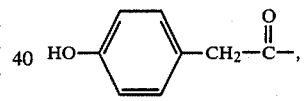

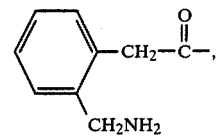

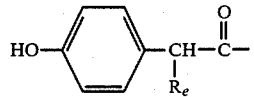

($R_e$ is preferably a carboxyl salt or sulfo salt) and

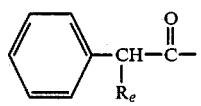

($R_e$ is preferably a carboxyl salt or sulfo salt).

(c) Heteroaromatic groups having the formula

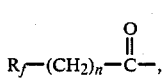

-continued

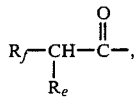

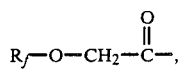

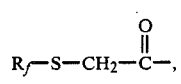

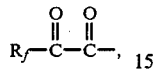

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

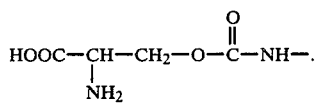

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino] arylacetyl groups having the formula

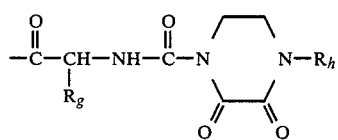

wherein $R_g$ is an aromatic group (including caroxyclic aromatics such as those of the formula

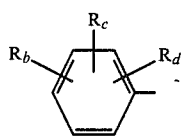

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

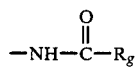

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oximino)arylacetyl groups having the formula

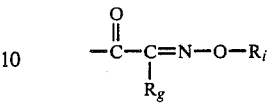

wherein $R_g$ is as defined above and $R_i$ is hydrogen, alkyl, cycloalkyl,

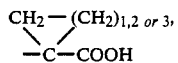

2-pyrrazolylmethyl, (2-oxo-3-pyrrolidinyl)methyl, alkylaminocarbonyl, arylaminocarbonyl (i.e.,

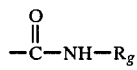

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino) arylacetyl groups include those wherein $R_g$ is 2-amio-4-thiazolyl. Also preferered are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

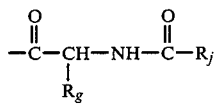

wherein $R_g$ is as defined above and $R_j$ is

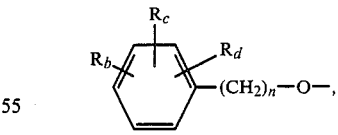

amino, alkylamino, (cyanoalkyl)amino, amido, alkylamido, (cyanoalkyl)amido,

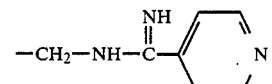

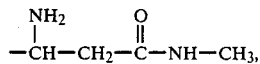

-continued

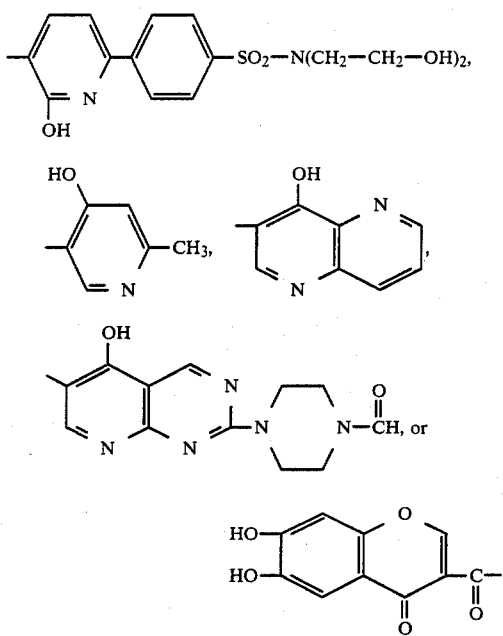

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

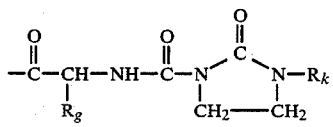

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mecapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino òr 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). Also included within the scope of this invention are racemic mixtures which contain the above-described β-lactams.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

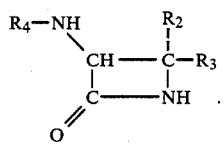

In formula II, and throughout the specification, the symbol "$R_4$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula

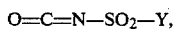

wherein Y is a leaving group such as chlorine, yields the corresponding compound having the formula

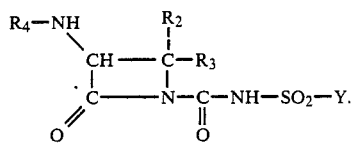

IV

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group "R" can be accomplished using the appropriate nucleophile having the formula

RH,   V optionally in the presence of a base (e.g., triethylamine), and yields the corresponding compound having the formula

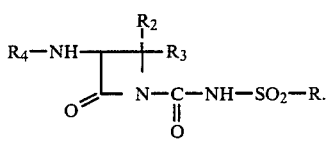

VI

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI.

Protected forms of a compound of formula V, and of all reactants described herein which contain a 3-hydroxy-4-pyridone moiety, include those compounds wherein the hydroxyl group is protected, those compounds wherein the hydroxyl group and the ring nitrogen are protected, and those compounds wherein both pyridone oxygens are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Deprotection of a compound of formula VI using conventional techniques yields the corresponding key intermediate having the formula

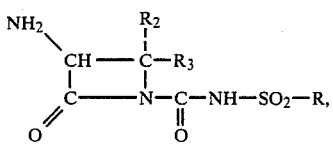

VII or a salt thereof. The particular deprotection reaction used will, of course, depend on the protecting group ("R$_4$") present. If, for example, R$_4$ is a t-butoxycarbonyl protecting group, deprotection can be accomplished by treatment of a compound of formula VI with acid (e.g., formic acid or trifluoroacetic acid). If, for example, R$_4$ is a benzyloxycarbonyl protecting group, deprotection can be accomplished by catalytic hydrogenation of a compound of formula VI. Alternatively, the R$_4$ protecting group can be removed simultaneously with the other pyridone protecting groups immediately following the above-described displacement reaction.

Well known acylation techniques can be used to convert an intermediate of formula VII to a corresponding product of formula I. Exemplary techniques include reaction of a compound of formula VII with a carboxylic acid (R$_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group (R$_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

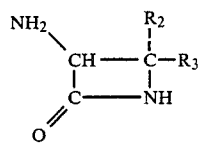

VIII to yield an intermediate having the formula

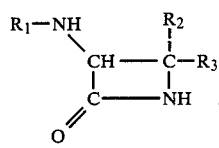

IX

A

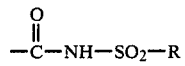

activating group can be introduced in the 1-position of a compound of formula IX (using the procedures described above) to obtain the corresponding product of formula I. In those instances wherein the acyl side-chain "R$_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

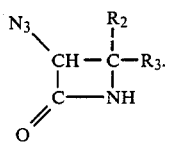

X

A

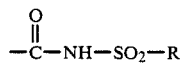

activating group can be introduced in the 1-position of a compound of formula X (using the procedures described above) to obtain the corresponding compound having the formula

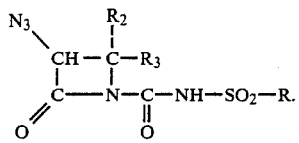

Reduction of an intermediate of formula XI yields the corresponding intermediate having the formula

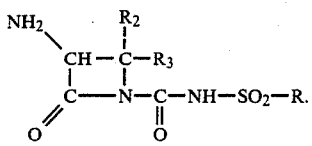

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

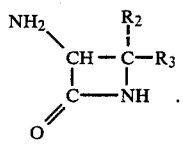

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

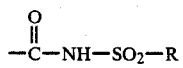

activating group in the 1-position) to yield the products of formula I.

Still another synthesis for preparing the compounds of formula I wherein $R_2$ and $R_3$ are each hydrogen utilizes a 6-acylaminopenicillanic acid having the formula

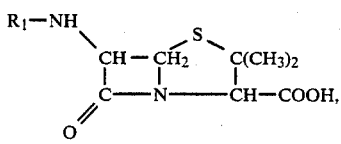

or a salt thereof, as the starting material. By adapting procedures described in the literature, 3-acylamino-2-azetidinone can be obtained from the corresponding 6-acylaminopenicillanic acid of formula XII: see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

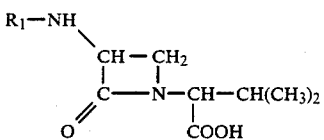

by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

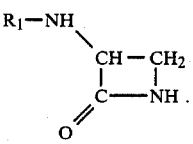

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A

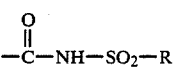

activating group can be introduced in the 1-position of a compound of formula XIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula

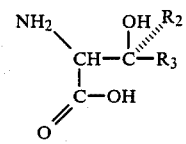

The amino group is first protected (with a protecting group "$R_4$", e.g., t-butoxycarbonyl). The carboxyl group of the protected amino acid is then reacted with an amine having the formula $$Z-O-NH_2,\qquad XVI$$

wherein Z is alkyl, benzyl or triphenylmethyl, in the presence of a carbodiimide to yield a compound having the formula

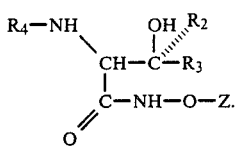
XVII

The hydroxyl group of a compound of formula XVII is converted to a leaving group ("OL") with a reagent, such as methanesulfonyl chloride or pyridine-SO$_3$ complex.

The fully protected compound having the formula

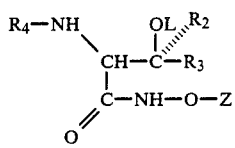
XVIII is cyclized by treatment with base, e.g., potassium carbonate. The reaction is preferably carried out in an organic solvent or an organic solvent/water mixture under reflux conditions, and yields a compound having the formula

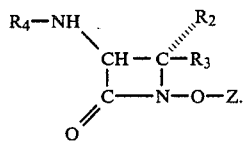
XIX

Alternatively, cyclization of a compound of formula XVII can be accomplished without first converting the hydroxyl group to a leaving group. Treatment of a compound of formula XVII with triphenylphosphine and diethylazodicarboxylate, yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the stereochemistry at the carbon atom bearing the R$_2$ and R$_3$ substituents when R$_2$ and R$_3$ are not the same.

Removal of the protecting group from the 1-position of an azetidinone of formula XIX can be accomplished via sodium reduction when Z is alkyl, and yields an intermediate having the formula

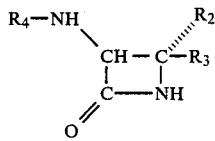
II (at least one of R$_2$ and R$_3$ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound.

An

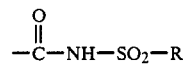

activating group can be introduced in the 1-position of a compound of formula II using the procedures described above, and the resulting compound can be deprotected and acylated.

The nucleophiles of formula V wherein R is

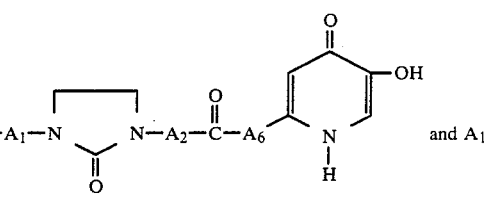

and A$_1$ and A$_2$ are each a single bond can be prepared by reacting a silylated derivative of

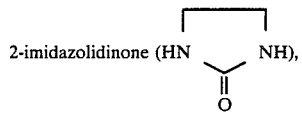

2-imidazolidinone (HN    NH), or the anion of 2-imidazolidinone formed with a strong non-nucleophilic base, with an activated, suitably protected derivative of an acid having the formula

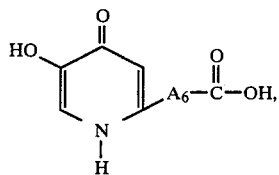
XX to obtain, upon deprotection, the corresponding compound having the formula

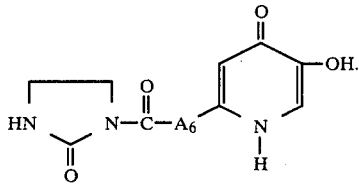
XXI

The reaction can be run in an inert organic solvent such as dimethylformamide, acetonitrile, dichloromethane, or tetrahydrofuran. The acid of formula XX can be activated with dicyclohexylcarbodiimide, or a combination of dicyclohexylcarbodiimide and hydroxybenzotriazole. An activated and suitably protected derivative of a compound of formula XX can also be the corresponding acid chloride (prepared with reagents such as phosphorus pentachloride, thionyl chloride, oxalyl chloride or triphenylphosphine/carbon tetrachloride) or a mixed anhydride (prepared with such reagents as diphenylphosphoryl chloride, pivaloyl chloride, or isobutyl chloroformate).

The compound of formula XX wherein $A_6$ is a single bond can be prepared as described in the literature; see *Helv. Chem. Acta*, 43, 469 (1960) and *J. Med. Chem.*, 17, 1 (1974).

The compound of formula XX wherein $A_6$ is —CH=CH— can be formed by oxidizing

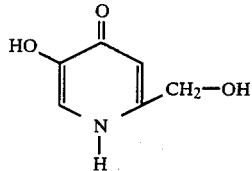
XXII (suitably protected) to the corresponding aldehyde having the formula

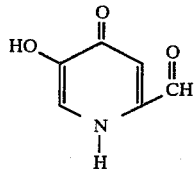
XXIII (suitably protected), reacting the aldehyde with a carboxyl protected derivative

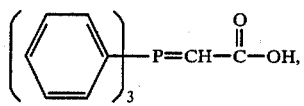
XXIV and deprotecting to yield

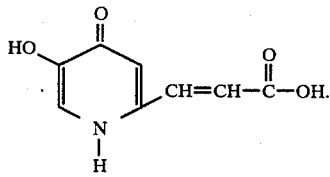
XXV

The compounds of formula XX wherein $A_6$ is —(CH$_2$)$_t$— and t is 2, 3 or 4 can be formed by conjugation of a compound of formula XXIII (suitably protected) with a Wittig reagent having the formula

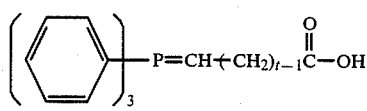
XXVI (suitably protected at the carboxyl group), subsequent hydrogenation of the resulting exocylic double bond, and deprotection to yield

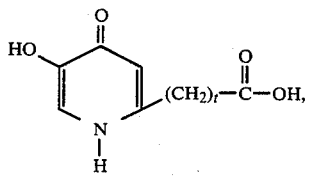
XXVII wherein t is 2, 3 or 4.

The compounds of formula XX wherein $A_6$ is —(CH$_2$)$_t$— and t is 1 can be formed by reaction of a suitably protected compound having the formula

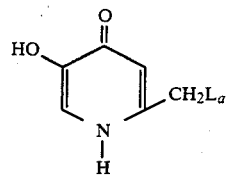
XXVIII (wherein $L_a$ is a leaving group such as chloride, bromide, methanesulfonyloxy or toluensesulfonyloxy) with cyanide and subsequent hydrolysis and deprotection to yield the compound of formula XXVII wherein t is 1. A compound of formula XXVIII can be prepared from a compound of formula XXII (suitably protected) by methods familiar in the art (such as thionyl chloride or methanesulfonylchloride/triethylamine).

The nucleophile of formula V wherein R is

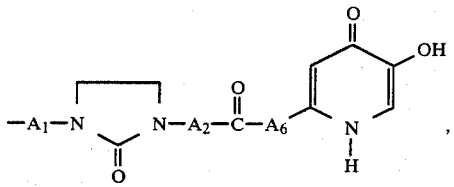

$A_1$ is a single bond and $A_2$ is —NH— can be prepared by reacting an activated and optionally protected derivative of a compound of formula XX with

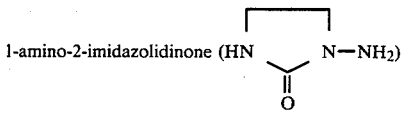

1-amino-2-imidazolidinone (HN   N—NH$_2$)

to yield upon deprotection

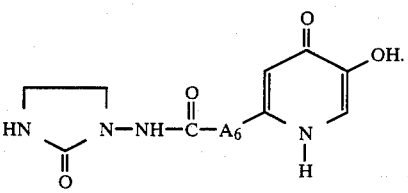
XXIX

The nucleophiles of formula V wherein R is

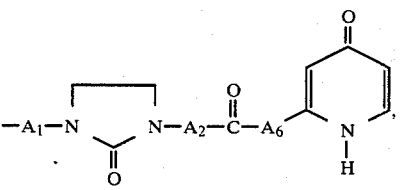

$A_1$ is a single bond and $A_2$ is —CH$_2$—CH$_2$—NH— can be prepared by reacting an activated and optionally protected derivative of a compound of formula XX with 1-(2-aminoethyl)-2-imidazolidinone (HN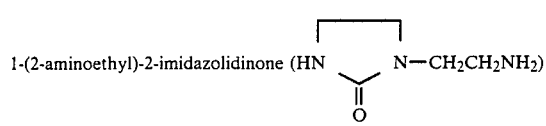N—CH₂CH₂NH₂)

to yield upon deprotection

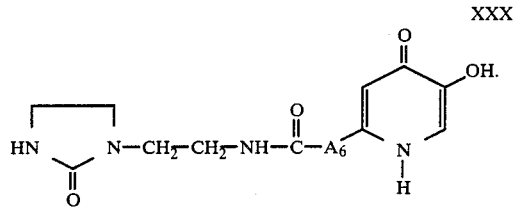   XXX

The nucleophiles of formula V wherein R is

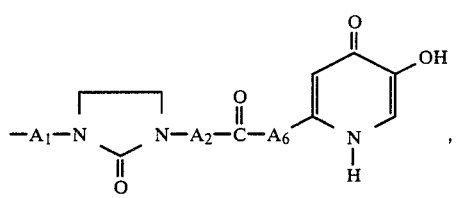

is a single bond and A₂ is

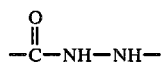

can be prepared by reacting

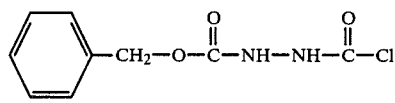   XXXI with a silylated form of 2-imidazolidinone, the anion of 2-imidazolidinone formed with a strong non-nucleophilic base, or with 2-imidazolidinone in the presence of an organic base to yield

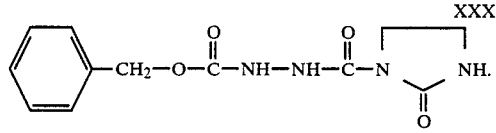   XXXII

Catalytic hydrogenation of the compound of formula XXXII yields the compound having the formula

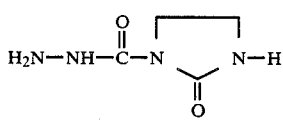   XXXIII which can be coupled with an activated and optionally protected derivative of a compound of formula XX to yield, upon deprotection,

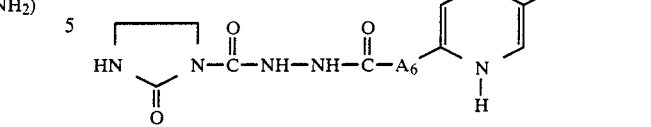   XXXIV

Alternatively, the compound of formula XXXIII can be prepared by first reacting 1-chlorocarbonyl2-imidazolidinone with t-butoxycarbonyl protected hydrazine to yield

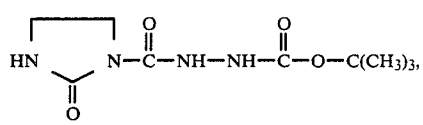   XXXV and deprotecting the compound of formula XXXV.

The nucleophiles of formula V wherein R is

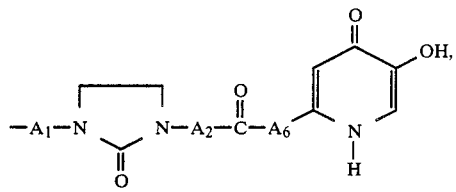

A₁ is

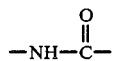

and A₂ is a single bond can be prepared by reacting a compound having the formula

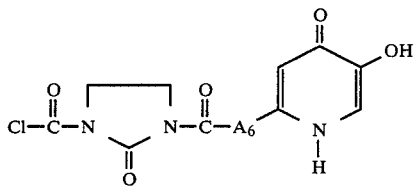   XXXVI (suitably protected) with hexamethyldisilazane to yield upon hydrolysis and deprotection a compound having the formula

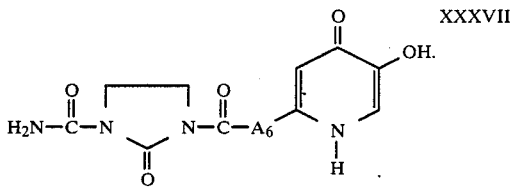   XXXVII

The compounds of formula XXXVI (suitably protected) can be prepared by reacting a silylated form of a compound of formula XXI (optionally protected) with phosgene.

Alternatively, a compound of formula XXXVII can be prepared by reacting a protected form of a compound of formula XXI with chlorosulfonyl isocyanate followed by hydrolysis of the resulting intermediate and cleavage of the protecting groups.

The nucleophiles of formula V wherein R is

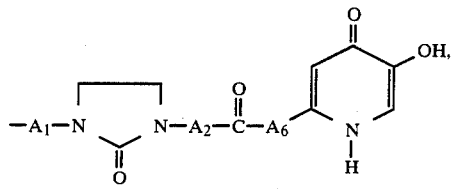

$A_1$ is

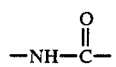

and $A_2$ is —NH— can be prepared by reacting a silylated form of the compound

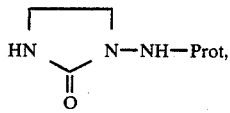  XXXVIII wherein the symbol Prot can be an amino protecting group such as t-butoxycarbonyl or benzyloxycarbonyl, with phosgene to yield

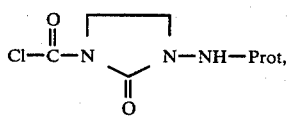  XXXIX which can be reacted with hexamethylsilazane to yield upon deprotection

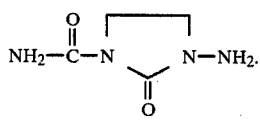  XL

Reaction of the compound of formula XL with an optionally protected activated form of a compound of formula XX yields upon deprotection

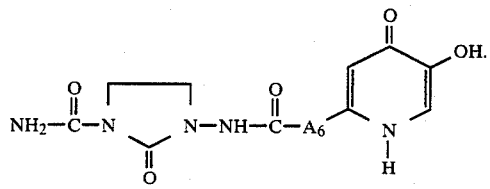  XLI

Alternatively, a compound of formula XL can be prepared by reacting the compound having the formula

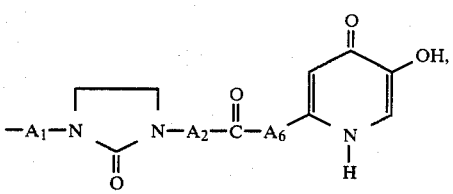  XLII with chlorosulfonyl isocyanate to yield upon hydrolysis

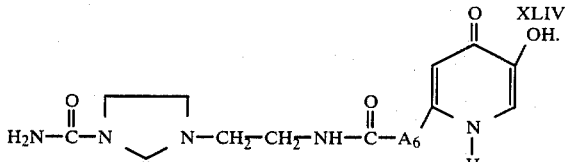  XLIII

Treatment of this compound with aqueous acid yields a salt of the compound of formula XL.

The nucleophiles of formula V wherein R is

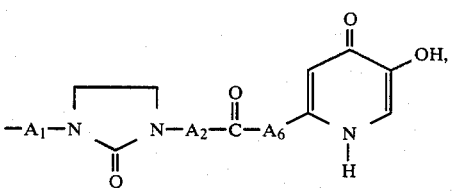

$A_1$ is

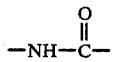

and $A_2$ is —CH$_2$—CH$_2$—NH— can be prepared by first deprotecting 1-(aminocarbonyl)-3-[2-[[(t-butoxy)carbonyl]amino]ethyl]-2-imidazolidinone and coupling the resulting compound with an activated form of a compound of formula XX (optionally protected) to obtain after deprotection

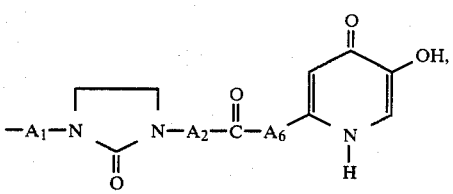  XLIV

The nucleophiles of formula V wherein R is

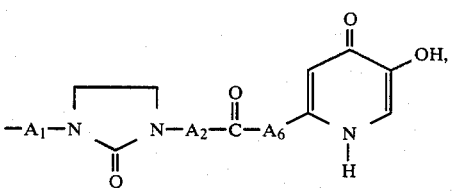

$A_1$ is

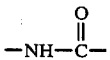

and $A_2$ is

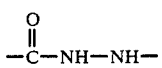

can be prepared by reacting a silylated form of a compound of formula XXXIV (optionally protected) with phosgene followed by hexamethyldisilazane to yield upon hydrolysis and deprotection

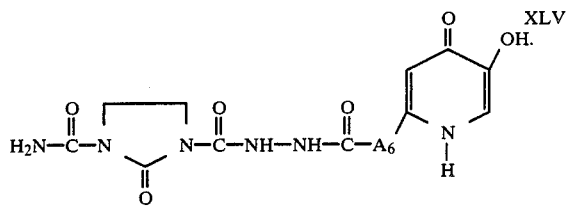
XLV

Alternatively, a compound of formula XLV can be prepared by reacting a protected form of a compound of formula XXXIV with chlorosulfonylisocyanate followed by hydrolysis of the resulting intermediate and cleavage of the protecting groups. Alternatively, compound XXXII can be reacted with chlorosulfonyl isocyanate followed by hydrolysis of the resulting intermediate to yield

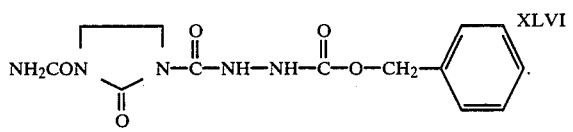
XLVI

Deprotection of XLVI by hydrogenolysis yields

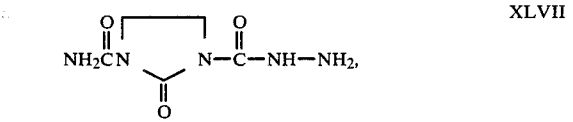
XLVII which can be coupled with an activated and optionally protected derivative of a compound of formula XX to yield upon deprotection a compound of formula XLV.

The nucleophiles of formula V wherein R is

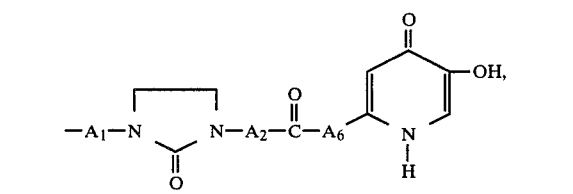

$A_1$ is —NH— and $A_2$ is a single bond can be prepared by coupling the compound of formula XXXVIII to an activated form of a compound of formula XX (optionally protected) and cleaving the protecting group to yield

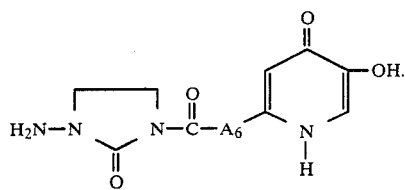
XLVIII

The nucleophiles of formula V wherein R is

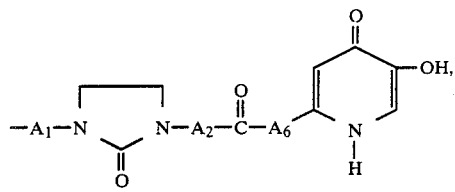

$A_1$ is —NH— and $A_2$ is —NH— can be prepared by coupling a monoprotected (preferably with t-butoxycarbonyl or benzyloxycarbonyl) derivative of 1,3-diamino-2-imidazolidinone with an activated form of a compound of formula XX (optionally protected) and deprotecting the resulting compound to yield.

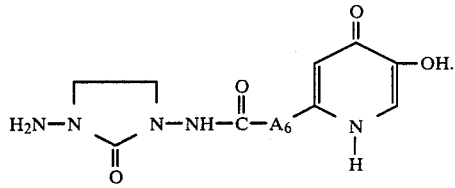
XLIX

Alternatively, a compound of formula XLIX can be formed by nitrosating a protected form of a compound of formula XXIX followed by reduction of the nitroso group and cleavage of the protecting groups.

The nucleophiles of formula V wherein R is

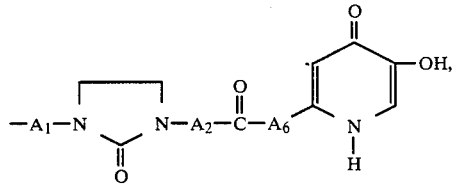

$A_1$ is —NH— and $A_2$ is —CH$_2$—CH$_2$—NH— can be prepared by nitrosating a compound of formula XXX (suitably protected) to yield a compound having the formula

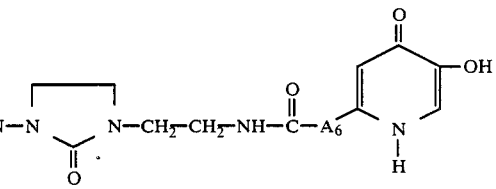
L (suitably protected) and reducing and deprotecting that compound to yield.

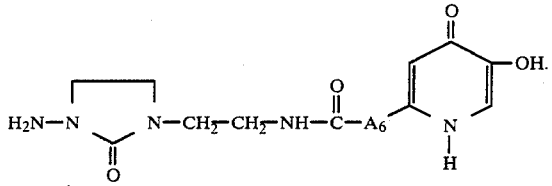

LI

The nucleophiles of formula V wherein R is

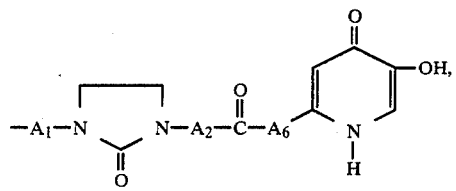

$A_1$ is —NH— and $A_2$ is

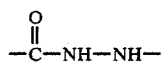

can be prepared by nitrosating, reducing and deprotecting a protected derivative of a compound of formula XXXIV. The resulting compound has the formula

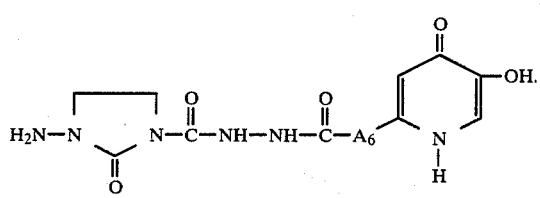

LII

Alternatively, a compound of formula LII an be prepared by reacting a compound of formula XXXVIII with phosgene to yield

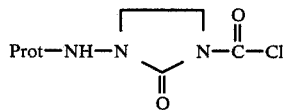

LIII which, on reaction with a monoprotected hydrazine in the presence of base, yields

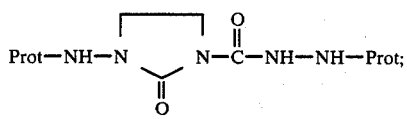

LIV (The two protecting groups must be different). Selective removal of the hydrazide protecting group yields

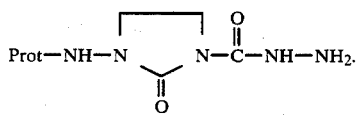

LV

Coupling of a compound of formula LV with an activated optionally protected form of a compound of formula XX, followed by deprotection, yields a compound of formula LII.

The nucleophiles of formula V wherein R is

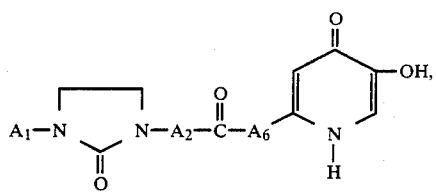

$A_1$ is

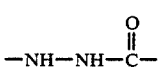

and $A_2$ is a single bond can be prepared by reacting a compound of formula XXXVI (preferably a protected derivative thereof) with hydrazine (preferably in monoprotected form) in the presnce of a base or with a silylated form of hydrazine or monoprotected hydrazine to yield a protected derivative of

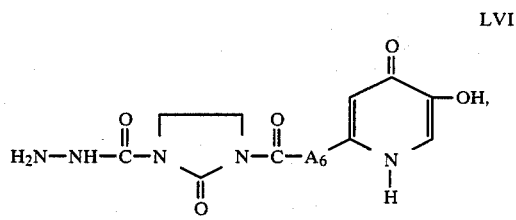

LVI which can be deprotected using conventional techniques.

Alternatively, a compound of formula XXXV (either a silylated derivative thereof or an anion thereof formed by reaction with a strong base) can be reacted with an activated form of formula XX (suitably protected) and deprotected to yield a compound of formula LVI.

The nucleophiles of formula V wherein R is

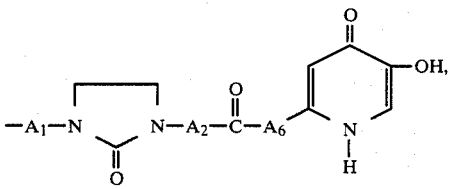

$A_1$ is

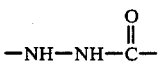

and $A_2$ is —NH— can be prepared by selective removal of the non-hydrazide protecting group of a compound of formula LIV, followed by coupling with an activated optionally protected compound of formula XX and subsequent deprotection to yield a compound having the formula

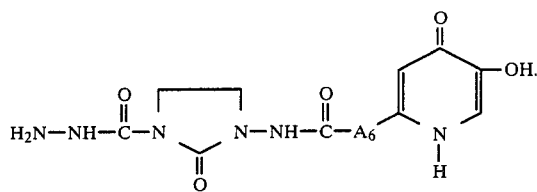

The nucleophiles of formula V wherein R is

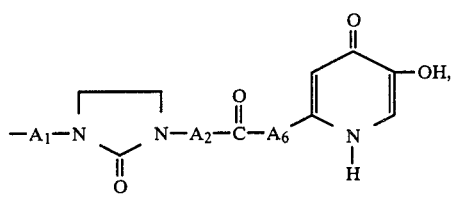

$A_1$ is

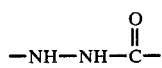

and $A_2$ is —CH$_2$—CH$_2$—NH— can be prepared by sequentially reacting a compound of formula XXX (or a protected derivative thereof) with phosgene followed by hydrazine (or a monoprotected derivative thereof) in the presence of a silylating agent such as N-methyl-N-(trimethylsilyl)trifluoroacetamide to yield upon deprotection

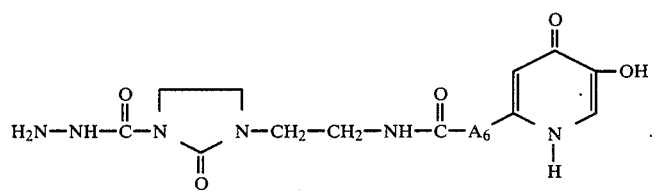

LVIII

Alternatively, an amino protected derivative of 1-(2-aminoethyl)-2-imidazolidinone (optionally silylated) can be reacted with phosgene, and then with a monoprotected derivative of hydrazine in the presence of a base or a silylating agent (e.g., N-methyl-N-(trimethylsilyl)trifluoroacetamide or bis(trimethylsilyl)acetamide) to yield a protected derivative of the compound having the formula

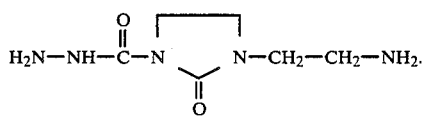

LIX

The groups used to protect the terminal amino groups in a compound of formula LIX should have been chosen so that the protecting group on the aminoethyl group can be selectively removed. The resulting monodeprotected compound can be coupled with an activated form of an acid of formula XX (or a prtected derivative thereof) to yield (after deprotection) a compound of formula LVIII.

The nucleophiles of formula V wherein R is

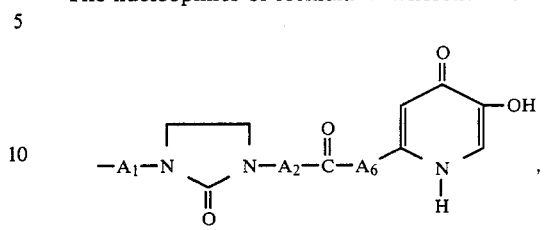

$A_1$ is

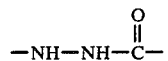

and $A_2$ is

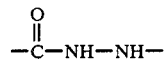

can be prepared by reacting the compound of formula XXXII (optionally as a silylated derivative thereof) with phosgene to yield a protected derivative of the compound having the formula

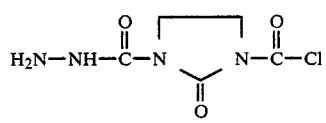

LX which can be coupled with a protected derivative of hydrazine to yield a protected derivative of

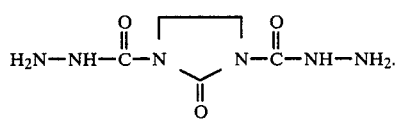

LXI

The groups used to protect the terminal amino groups in a compound of formula LXI should be chosen so that one of the protecting groups can be selectively removed. The resulting monodeprotected compound can be coupled with an optionally protected activated form of an acid of formula XX to yield (after deprotection) a compound having the formula

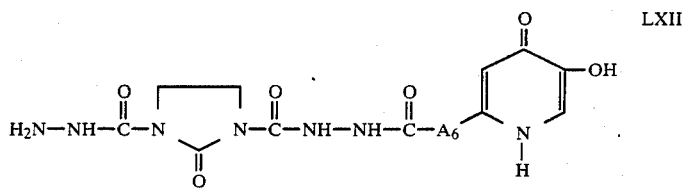

The nucleophiles of formula V wherein R is

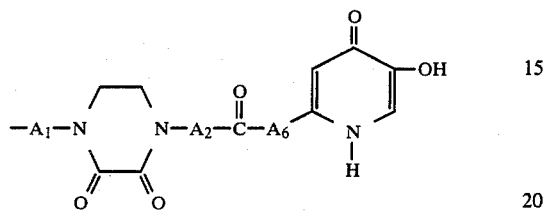

can be prepared using the methodology described above for the preparation of the nucleophiles of formula V wherein R is

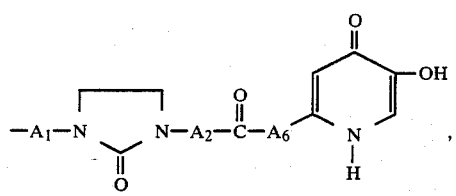

but substituting the appropriate 2,3-piperazinedione reactants for the 2-imidazolidinone reactants.

The nucleophiles of formula V wherein R is

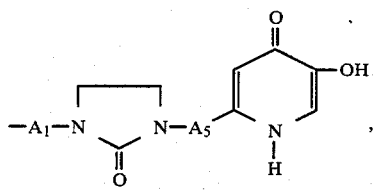

$A_1$ is a single bond and $A_5$ is a single bond can be prepared utilizing a suitably protected derivative of the compound

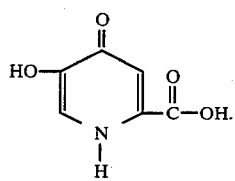

A compound having the formula

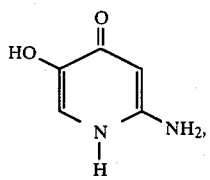

can be prepared by converting a protected form of the compound having the formula

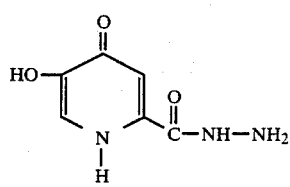

to a protected form of the compound of formula LXIV by the procedure of K. Heyns et al., *Chem. Ber.*, 87, 1440 (1954), followed by deprotection to yield the compound of formula LXIV, per se.

A compound of formula LXV can be prepared from a suitably protected form of a compound of formula LXIII by conversion to an ester (such as ethyl or methyl), reaction with hydrazine and deprotection. Alternatively, a suitably protected, activated form of a compound of formula LXIII can be reacted with a monoprotected hydrazine to yield upon deprotection a compound of formula LXV.

Reaction of the compound of formula LXIV (or a suitably protected derivative thereof) with 2-(chloroethyl)isocyanate optionally in the presence of a base (such as triethylamine) or a silylating agent yields upon deprotection the compound having the formula

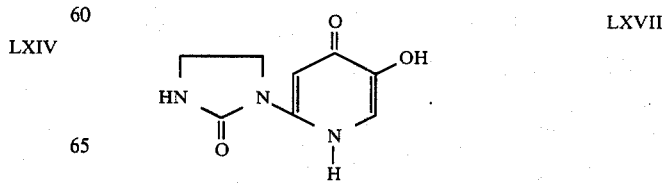

Treatment of LXVI (or a suitably protected derivative thereof) with base yields upon deprotection the compound having the formula

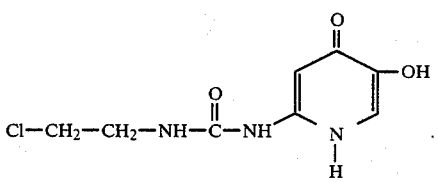

The nucleophiles of formula V wherein R is

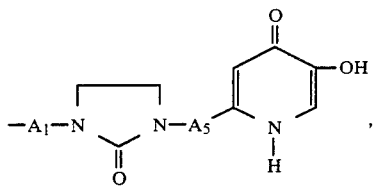

$A_1$ is a single bond and $A_5$ is —$CH_2$— can be prepared by reacting the compound having the formula

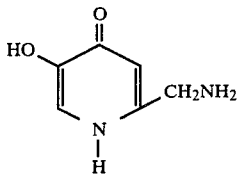

LXVIII (or an derivative in which the pyridone is suitably protected and the primary amine is unprotected) with 2-(chloroethyl)isocyanate to obtain the compound having upon deprotection the formula

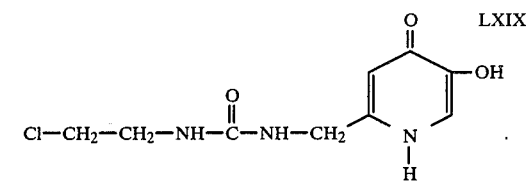

LXIX

Treatment of LXIX (or a suitably protected derivative thereof) with base yields the compound having the formula

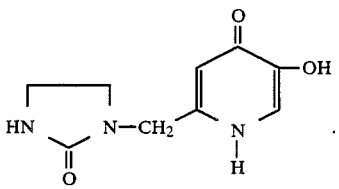

LXX

A compound of formula LXVIII can be prepared from a compound of formula XXVIII (suitably protected) by treatment with azide, reduction of the azide, and deprotection.

The nucleophiles of formula V wherein R is

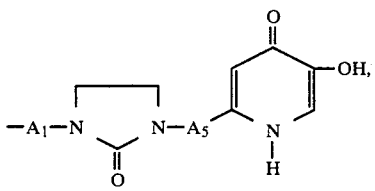

$A_1$ is a single bond and $A_5$ is —N=CH— or —NH—$CH_2$ can be prepared by condensing 1-amino-2-imidazolidinone with the aldehyde having the formula XXIII (optionally protected) to yield (after deprotection) the compound having the formula

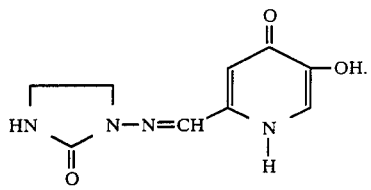

LXXI

Reduction of the compuond of formula LXXI (optionally protected) by catalytic hydrogenation or using sodium cyanoborohydride yields the compound having the formula

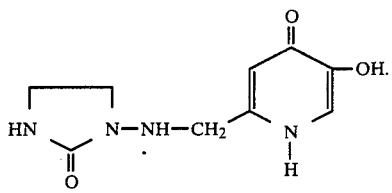

LXXII

The nucleophiles of formula V wherein R is

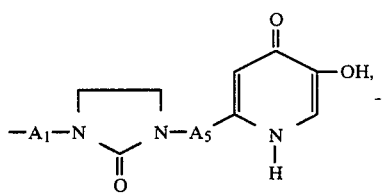

$A_1$ is a single bond and $A_5$ is

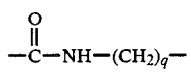

can be prepared by reacting 1-chlorocarbonyl- 2-imidazolidinone with a compound having the formula

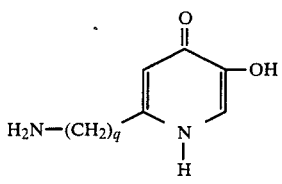

LXXIII (or a suitably protected derivative thereof) in the presence of a base, or with a silylated derivative of a compound of formula LXXIII, to yield following deprotection the compound having the formula

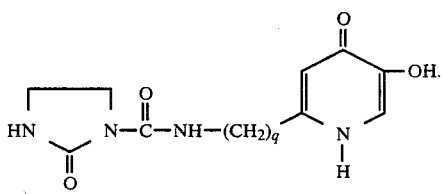

LXXIV

The nucleophiles of formula V wherein R is

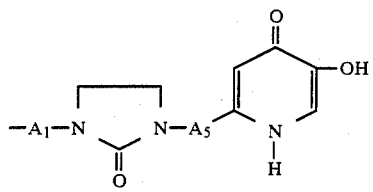

and A₁ is

can be prepared by racting a suitably protected derivative of a compound of formula LXVII, LXX, LXXI, LXXII or LXXIV with phosgene to yield a protected derivative of

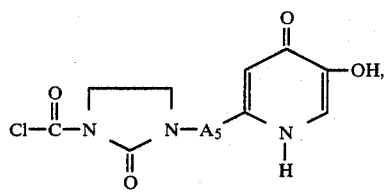
LXXV which can be reacted with hexamethylsilazane to yield upon deprotection and hydrolysis

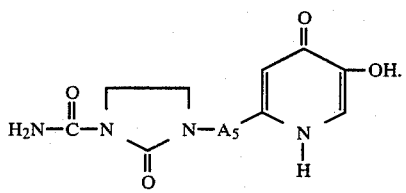
LXXVI

Alternatively, nucleophiles of formula V wherein R is

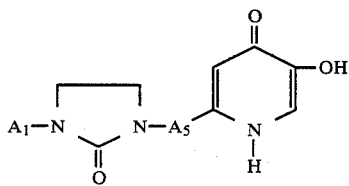

and A₁ is

can be preapred by reacting a suitably protected derivative of a compound of formula LXVII, LXX, LXXI, LXXII, or LXXIV with chlorosulfonyl isocyanate to yield upon hydrolysis and deprotection a compound of formula LXXVI.

The nucleophiles of formula V wherein R is

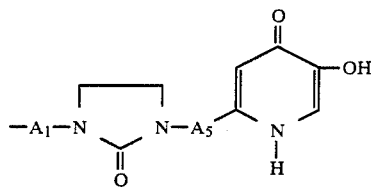

and A₁ is —NH— can be prepared by nitrosating a suitably protected derivative of a compound of formula LXVII, LXX, LXXI, LXXII or LXXIV (with, for example, nitrous acid), reducing the resulting compound (using, for examplie, zinc under acidic conditions) and deprotecting to yield

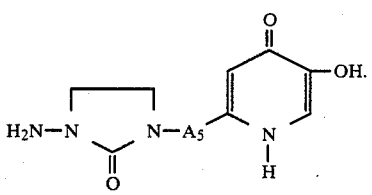
LXXVII

Alternately, the compounds of formula LXXVII wherein A₅ is

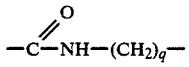

can be prepared by reacting a compound of formula XXXIX with a optionally protected form of a compound of formula LXIV or LXVIII in the presence of base or a silylating agent to yield upon deprotection

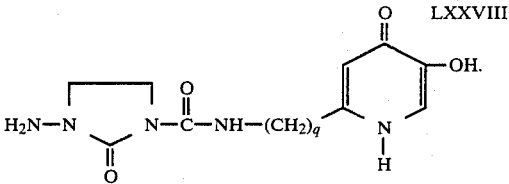
LXXVIII

Alternately, those compounds of formula LXXVII wherein A₅ is —N═CH— or —NH—CH₂— can be prepared by reacting monoprotected 1,3-diamino-2-imidazolidinone with a compound of formula XXIII (or a protected derivative thereof) and deprotecting the product top yield the derivative of formula LXXVII wherein A₅ is —N═CH—. Reduction of that derivative yields the compound of formula LXXVII wherein A₅ is —NH—CH₂—.

The nucleophiles of formula V wherein R is

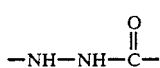

can be prepared by reacting a compound of formula LXXV (suitably protected) with a monoprotected hydrazine in the presence of a base or a silylating agent. The products, after deprotection, have the formula

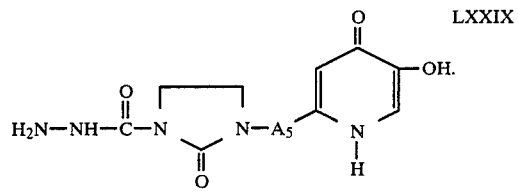

LXXIX

The nucleophiles of formula V wherein R is

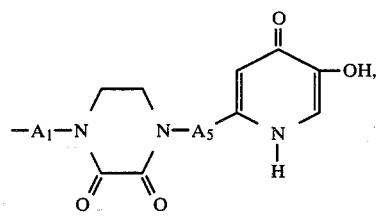

$A_1$ is a single bond and $A_5$ is a single bond or $-CH_2-$ can be prepared by reacting a compound having the formula LXIV or LXVIII (or a suitably protected derivative thereof) with aziridine or an activated aziridine (activated with such groups as acyl or sulfonyl) to yield upon deprotection.

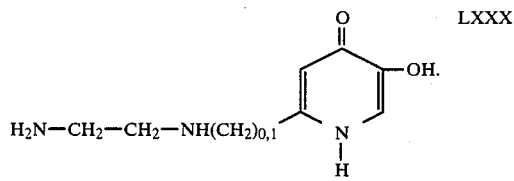

LXXX

A compound of formula LXXX (or a suitably protected derivative thereof) can be converted to the desired piperazinedione having the formula

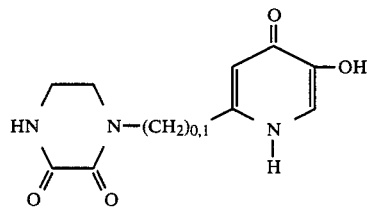

LXXXI by reaction with a dialkyl oxalate (and subsequent deprotection if necessary).

The nucleophiles of formula V wherein R is

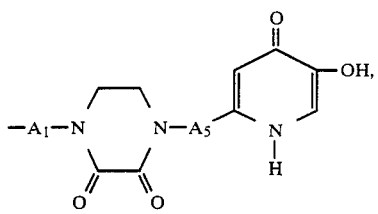

$A_1$ is a single bond and $A_5$ is $-N=CH-$ or $-NHCH_2-$ can be prepared using the methodology described above for the preparation of the nucleophiles of formula V wherein R is

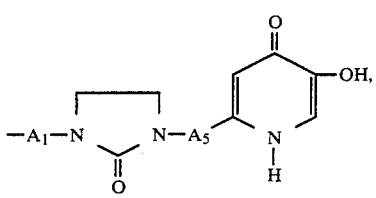

$A_1$ is a single bond and $A_5$ is $-N=CH-$ or $-NHCH_2-$, but substituting 1-amino-2,3-piperazinedione for 1-amino-2-imidazolidinone. The resulting compounds would have the formulas

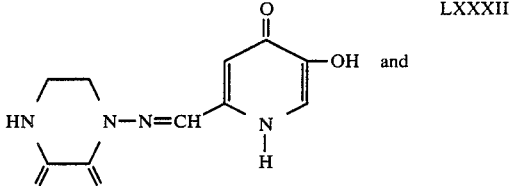

LXXXII and

LXXXIII

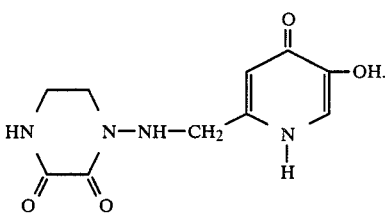

The nucleophiles of formula V wherein R is

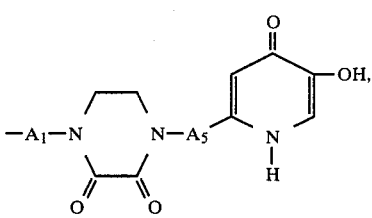

$A_1$ is a single bond and $A_5$ is

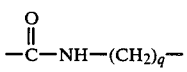

can be prepared by reacting an optionally protected derivative of

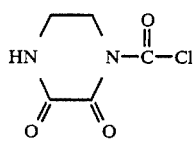
LXXXIV with a compound of formula LXXIII (or a suitably protected derivative thereof) in the presence of a base or a silylating agent. The resulting intermediate can be deprotected to yield

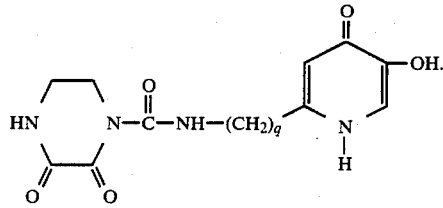
LXXXV

The nucleophiles of formula V wherein R is

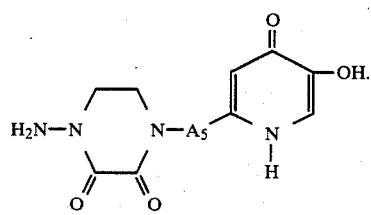

and $A_1$ is —NH— can be preapared by nitrosation of a protected derivative of a compound having the formula LXXXI, LXXXII, LXXXIII or LXXXV (with, for example, nitrous acid), reducing the resulting compound (using, for example, zinc under acidic conditions) and deprotecting to yield

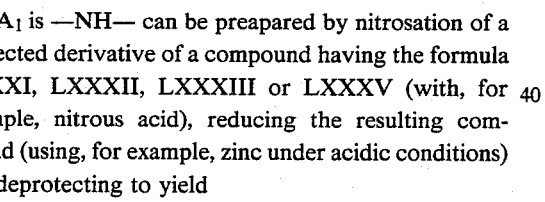
LXXXVI

Alternatively, those compounds of formula LXXXVI wherein $A_5$ is —N=CH— or —NH—CH$_2$— can be prepared by reacting monoprotected, 1,4-diamino2,3-piperazinedione with a compound of formula XXIII (or a protected derivative thereof) and deprotecting the product to yield a compound of formula LXXXVI, wherein $A_5$ is —N=CH— which can then be reduced to a compound of formula LXXXVI wherein $A_5$ is —NH—CH$_2$—. Alternatively, reduction of —N=CH— can precede deprotection.

The nuceleophiles of formula V wherein R is

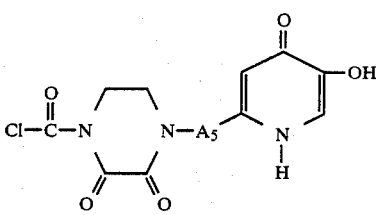

and $A_1$ is

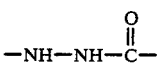

can be prepared by reacting a suitably protected derivative of a compund of formula LXXXI, LXXXII, LXXXIII, or LXXXV with phosgene to yield

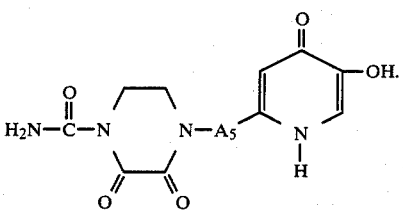
LXXXVII which can be reacted with hexamethyldisilazane to yield upon deprotection and hydrolysis

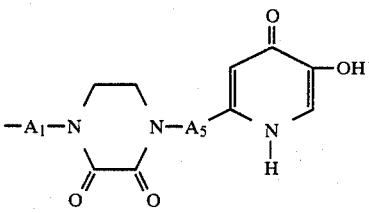
LXXXVIII

Alternatively, the nucleophiles of formula V wherein R is

and $A_1$ is $$-\text{NH}\overset{\text{O}}{\underset{\|}{\text{C}}}-$$

can be prepared by reacting a suitably protected derivative of a compuond of formula LXXXI, LXXXII, LXXXIII, or LXXXV with chlorosulfonyl isocyanate to yield a compound of formula LXXXVIII upon hydrolysis and deprotection.

The nuceleophiles of formula V wherein R is

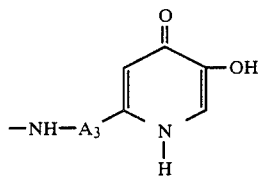

and $A_3$ is -$(CH_2)_p$- have been described; see formula LXIV and LXVIII.

The nucleophiles of formula V wherein R is

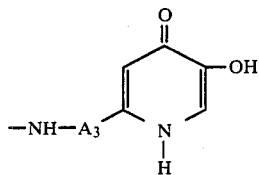

and $A_3$ is

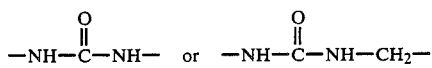

can be prepared by reacting a compound of formula XXXI with a compound of formula LXIV or LXVIII (optionally protected) in the presence of base or a silylating agent, followed by removal of any protecting groups.

Alternatively, nucleophiles of formula V wherein R is

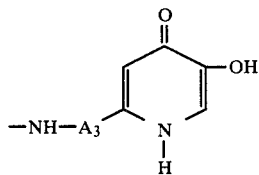

and $A_3$ is

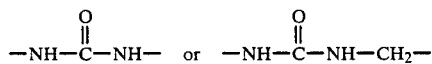

can be prepared from a suitably protected form of a compound formula LXIV or LXVIII by reaction with phosgene followed by treatment with a monoprotected derivative of hydrazine in the presence of base or a silylating agent and deprotection.

The nucleophiles of formula V wherein R is

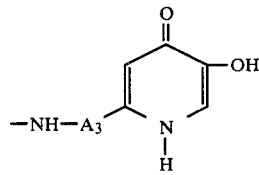

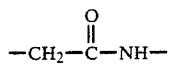

or —$CH_2$—CO—NH—$CH_2$— can be prepared by coupling an activated N-protected glycine derivative with a compound of formula LXIV or LXVIII (optionally protected) followed by deprotection.

The nucleophiles of formula V wherein R is

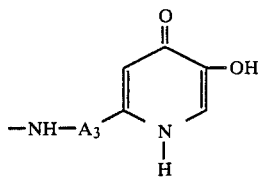

and $A_3$ is —NH—$CH_2$— can be prepared by reacting an optionally protected derivative of the aldehyde of formula XXIII with hydrazine or monoprotected hydrazine followed by reduction of the carbon-nitrogen double bond and subsequent deprotection.

Alternatively, a monoprotected hydrazine may be monoalkylated on the free amino group with a compund of formula XXVIII (suitably protected) followed by deprotection to give a nucleophile of formula V wherein R is

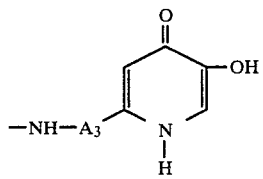

and $A_3$ is —NH—$CH_2$—.

The nucleophiles of formula V wherein R is

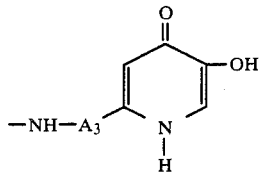

and $A_3$ is —O—$CH_2$— can be prepared by reacting a suitably protected derivative of the compound of formula XXII with N-hydroxyphthalimide under Mitsunobu conditions (presence of triphenylphosphine and diethylazodicarboxylate) to yield a protected derivative of the compound

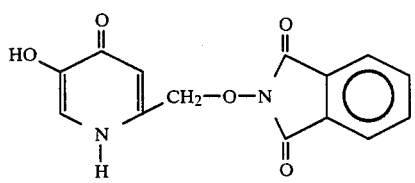

LXXXIX which can be deprotected to the compound

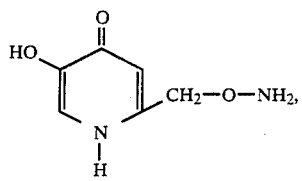

XC

Alternatively, the compound of formula XC can be prepared by reacting a compound of forumula XXVIII (suitably protected) with N-hydroxyphthalimide in the presence of a base.

The nucleophiles of formula V wherein R is

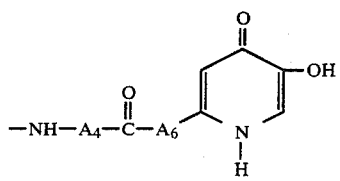

and $A_4$ is —NH— can be prepared by reacting a monoprotected hydrazine with an activated, optionally protected derivative of an acid of formula XX to obtain, after deprotection, a compound of the formula

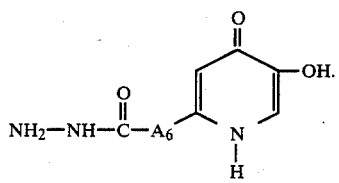

XCI

Alternatively, the compounds of formula XCI can be prepared by reacting a carboxylic acid ester of a suitably protected derivative of a compound of formula XX with hydrazine and then deprotecting.

The nucleophiles of formula V wherein R is

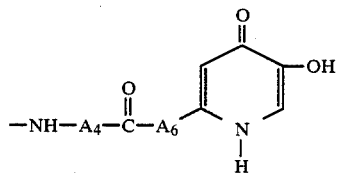

and $A_4$ is —$(CH_2)_p$— and p is 0 can be prepared by reacting ammonia or hexamethyldisilizane with an activated, optionally protected derivative of an acid of formula XX to obtain, after deprotection, a compound having the formula

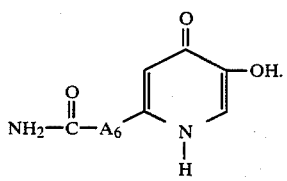

XCII

The nucleophiles of formula V wherein R is

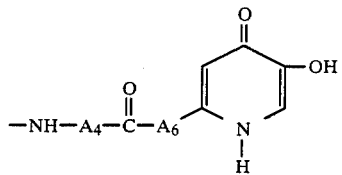

and $A_4$ is —$(CH_2)_p$— and p is 1 can be prepared by treatment of a suitably protected activated derivative of a compound of formula XX with diazomethane followed by hydrochloric acid to yield a protected derivative of a compound having the formula

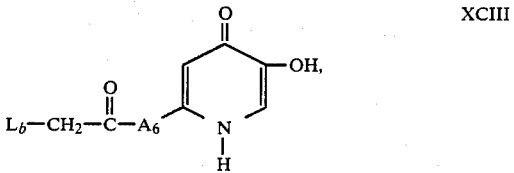

XCIII wherein "$L_b$" is chlorine. A compound of formula XCIII wherein $L_b$ is chlorine can then be treated with an iodide or bormide salt (such as sodium iodide or lithium bromide) to give a protected derivative of a compound of formula XCIII wherein $L_b$ is bromine or iodine. Displacement of the leaving group "$L_b$" (wherein $L_b$ is chlorine, bromine or iodine) with azide followed by reduction and deprotection yields

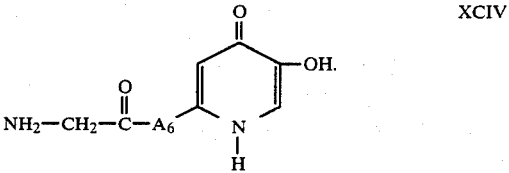

XCIV

The nucleophile of formula V wherein R is

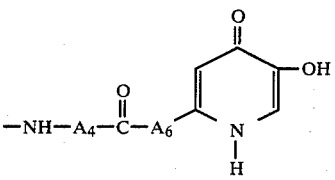

and $A_4$ is —$(CH_2)_y$—NH— can be prepared by reacting a (optionally monoprotected) compound of formula $NH_2$—$(CH_2)_y$—$NH_2$   XCV with an activated, optionally protected derivative of an acid of formula XX to obtain, after deprotection, a compound having the formula

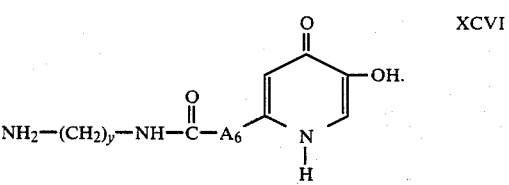

XCVI

The nucleophiles of formula V wherein R is

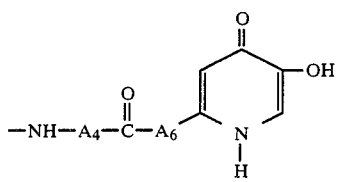

and A₄ is

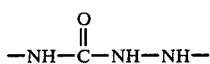

can be prepared by reacting a compound of formula XCI (suitably protected) with a compound having the formula

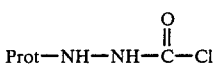 XCVII in the presence of a silylating agent and then removing the protecting groups.

The nucleophiles of formula V wherein R is

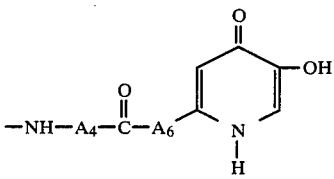

and A₄ is

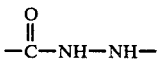

can be prepared by reacting

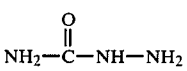

(in the presence of a base or a silylating agent) with an activated, optionally protected derivative of formula XX to obtain, after deprotection, a compound having the formula

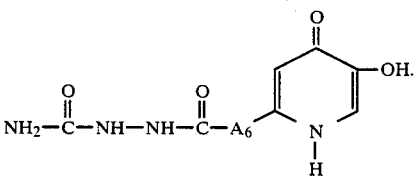 XCVIII

The nucleophile of formula V wherein R is

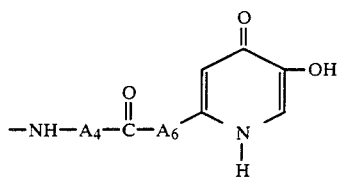

and A₄ is $$\begin{array}{c} CH_2X \\ | \\ -N- \end{array}$$

can be prepared by reacting an optionally protected hydrazine derivative of the formula $$NH_2-NH-CH_2-X \qquad XCIX$$

with an activated, optionally protected derivative of an acid of formula XX to obtain, after deprotection, a compound having the formula

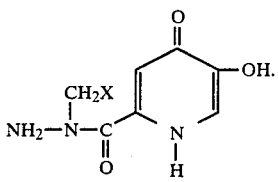 C

Alternatively, compounds of formula C wherein X is hydrogen can be prepared by reacting methylhydrazine with a carboxylic ester derivative of the acid of formula XX (or a suitably protected derivative thereof).

The compounds of formula I wherein R is

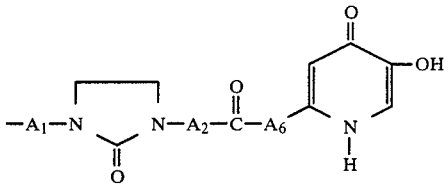

are preferred. Most preferred are those compounds of formula I wherein R is

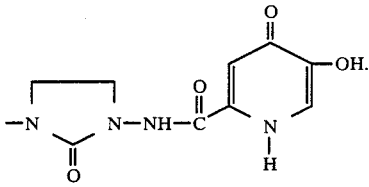

Also preferrred are those compounds of formula I wherein R₁ is

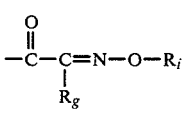

and $R_g$ is 2-amino-4-thiazolyl and $R_i$ is methyl, ethyl, carboxymethyl, 1-carboxy-1-methylethyl, 1-carboxy-1-ethyl or

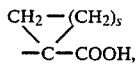

wherein s is 1, 2 or 3. The use of these preferred $R_1$ acyl groups yields a product which exists as the syn or anti isomer or as a mixture of isomers. The syn isomer exhibits greater activity than the anti isomer.

The following examples are specific embodiments of this invention.

EXAMPLE 1
[3S(Z)]-2-[[[1-(2-Amino-4-thiazolyl)-2-[[1-[[[[3-[[(1,-,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt

(A)
2-(Hydroxymethyl)-5-(phenylmethoxy)-4H-pyran-4-one 69 g (3 mol) of sodium were dissolved in 5 l of methanol. Subsequently 425.3 g (3 mol) of 5-hydroxy-2-(hydroxymethyl)-4H-pyran-4-one was added and stirred at 30° C. until a clear solution was obtained. 595 g (3.5 mol) of benzyl bromide was then added and stirred for 1 hour under reflux. The warm and very dark colored solution was poured into 15 l of ice water. The product crystallized immediately. The crystals were collected and washed first with 8 l of water and then twice with 2.5 l of ether. The product was left to stand overnight and finally dried at 50° C. for 16 hrs. Yield: 646 g=92.6%.

(B) 4-Oxo-5-(phenylmethoxy)-4H-pyran-2-carboxylic acid 232 g (1 mol) of 2-(hydroxymethyl)-5-(phenylmethoxy)-4H-pyran-4-one were put into a 10 l stirring flask containing 6.6 l of acetone and 400 ml of water. The clear solution was cooled to +5° C. by means of an ice-bath. While maintaining the temperature at +5° to 10° C., 640 ml of Jones Reagent (202 g $CrO_3$, 600 ml water, 174 ml $H_2SO_4$) was added dropwise over a period of 1 hr. Stirring was continued for 2 hours without cooling. The reaction mixture was filtered through a glass frit and the dark-green residue washed with 500 ml of acetone. The filtrate was then evaporated until all of the acetone was removed. To the aqueous, partly crystalline product was added 1.2 l of methanol, and this mixture was then heated to its boiling point. The resulting clear dark-green solution was placed in an ice-bath and the product allowed to crystallize. The crystalline product was filtered and washed with 500 ml of a cold solvent mixture consisting of 250 ml methanol +250 ml water and finally dried. Yield: 195 g=79%. From the mother liquor a further 5% of the product could be isolated.

(C)
1,4-Dihydro-4-oxo-5-(phenylmethoxy)-2-pyridinecarboxylic acid 300 g (1.22 mol) of 4-oxo-5-(phenylmethoxy)-4H-pyran-2-carboxylic acid was put into a flask and 5 l of 33% $NH_4OH$ was carefully added with stirring. The reaction mixture was then stirred under reflux. After 3 hours, one additional liter of 33% $NH_4OH$ was added slowly. Stirring was continued for further 2 hours under reflux. The reaction solution was then evaporated until the product crystallized. The product was transferred back into the reaction flask and water added until a clear solution was obtained (approximately 5 l, pH 6.38). This solution was stirred vigorously while concentrated hydrochloric acid was added dropwise until a pH of 3 was obtained. The precipitated white product was removed by filtration, thoroughly washed with water and dried. Yield: 273 g (1.12 mol)=91.8%.

(D)
1,4-Dihydro-4-oxo-N-(2-oxo-1-imidazolidinyl)-5-(phenylmethoxy)-2-pyridinecarboxamide 1,4-Dihydro-4-oxo-5-(phenylmethoxy)-2-pyridinecarboxylic acid (12.26 g, 0.05 mol) and 1-amino-2-imidazolidinone (5.56 g, 0.055 mol) were suspended in 120 ml of dimethylformamide. To the suspension was added 0.3 g of dimethylaminopyridine and 0.4 g of N-hydroxybenzotriazole. After stirring for 30 minutes at room temperature, a solution of 11.35 g of dicyclohexylcarbodiimide (0.055 mol) in 50 ml of dimethylformamide was added dropwise and the mixture was stirred overnight at room temperature. The precipitate (dicyclohexylurea) was filtered off and the filtrate evaporated in vacuo. The remaining syrup crystallized on treatment with aqueous sodium bicarbonate, yielding 11.7 g of the title compound, melting point 158°–160° C. An additional crop of 0.8 g of product, melting point 162°–164° C., crystallized from the aqueous filtrate.

(E)
1,4-Dihydro-5-hydroxy-4-oxo-N-(2-oxo-1-imidazolidinyl)-2-pyridinecarboxamide To a suspension of 12 g (0.0365 mol) of 1,4-dihydro-4-oxo-N-(2-oxo-1-imidazolidinyl)-5-(phenylmethoxy)-2-pyridinecarboxamide in 150 ml of acetonitrile was added 36.1 ml (0.146 mol) of bis(trimethylsilyl)acetamide to form a slightly turbid solution. After filtration, 6 g of 10% palladium on charcoal was added and hydrogen was passed through the stirred reaction mixture. After hydrogenation for 60 minutes, the catalyst was filtered off and 15 ml of methanol and 2 ml of acetic acid were added. Stirring was continued overnight; the title compound crystallized out, yielding 6.6 g, melting point 270°–275° C.

(F)
(3S)-[1-[[[[3-[[(1,4-Dihydro-5-hydroxy-4-oxo-2-pyridinyl)carbonyl]amino]-2-oxo-1-imidazolidinyl]sulfonyl]amino]carbonyl]-2-oxo-3-azetidinyl]carbamic acid, phenylmethyl ester To a suspension of 13.8 g of (S)-3-[[(phenylmethoxy)carbonyl]amino]-2-azetidinone in 500 ml of ethyl acetate was added 5.63 ml (0.0626 mol) of chlorosulfonyl isocyanate. The mixture was stirred for 1 hour at room temperature to form a solution of (S)-1-[[(chlorosulfonyl)amino]carbonyl]-3-[[(phenylmethoxy)carbonyl]amino]-2-azetidinone. The solution was cooled to 0° C., at which temperature a solution of silylated 1,4-dihydro-5-hydroxy-4-oxo-N-(2-oxo-1-imidazolidinyl)2-pyridinecarboxamide (prepared from a suspension of 14.9 g (0.0626 mol) of 1,4-dihydro-5-hydroxy-4-oxo-N-(2-oxo-1-imidazolidinyl)-2-pyridinecarboxamide in 500 ml of ethyl acetate by the addition of 46.4 ml of N-methyl-N-(trimethylsilyl)trifluoroacetamide (0.25 mol) and stirring for 30 minutes) was added slowly. Then 150 ml of dichloromethane was added, and the mixture was stirred at room temperature overnight. To the clear solution was added 26.2 ml of triethylamine (0.188 mol), followed by 300 g of ice and 200 ml of water. The pH was 6.5. After stirring for 1½ hours, the two phases were separated and the aqueous phase was washed with three 200 ml portions of ethyl acetate. After removal of residual ethyl acetate in vacuo, the pH of the aqueous phase was adjusted to 2 by the slow addition of 2N hydrochloric acid (47 ml) with cooling. The crystals were filtered off, suspended in 200 ml of ethyl acetate and stirred for one hour. Then the crystals were filtered off, washed twice with 30 ml of ethyl acetate and twice with 50 ml of petroleum ether and dried in vacuo, to yield 28.6 g of the title compound, melting point 190°–200° C., dec.

(G)
(3S)-3-Amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, trifluoroacetate (1:2) salt At room temperature, 4 g (0.00713 mol) of (3S)-[1-[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]carbamic acid, phenylmethyl ester was added to a mixture of 15 ml of trifluoroacetic acid and 3.5 ml of thioanisole at 10° C. The clear solution was stirred overnight at 10° C. After evaporation in vacuo at room temperature, the remaining syrup was treated with ether to yield the title compound as a yellowish solid. The yield was almost quantitative.

(H)
[3S(Z)]-2-[[[1-(2-Amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a solution of 3.08 g (0.007 mol) of (Z)-2-amino-α-[[2-(diphenylmethoxy)-1,1-dimethyl-2-oxoethoxy]imino]-4-thiazoleacetic acid in 70 ml of dimethylformamide was added 2.9 ml (0.021 mol) of triethylamine followed, after cooling to −30° C. under nitrogen, by 1.55 ml (0.007 mol) of diphenyl chlorophosphate. The mixture was stirred for 1 hour at −30° C. Then 1.95 ml of triethylamine (0.014 mol) was added followed by 0.007 mol of (3S)-3-amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, trifluoroacetate (1:2) salt. The reaction mixture was stirred at −10° C. for 2 hours and at 0° C. for 1 hour. Then the solvent was removed in vacuo. Treatment of the residue with water and ethyl acetate yielded an insoluble product which solidified on treatment with ether yielding 8.0 g of crude compound.

(I)
[3S(Z)]-2-[[[1-(2-Amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt Crude [3S(Z)]-2-[[[1-(2-amino-4-thiazolyl)-2-[[1-[[[[3-[[(1,4-dihydro-5-hydroxy-4-oxo-2pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (8 g) was suspended in 15 ml of anisole. After cooling to −10° C., 80 ml of trifluoroacetic acid was added dropwise and the mixture was stirred at −10° C. for 1 hour. The addition of ether at 0° C. precipitated the trifluoroacetate salt of the free acid of the product (4.1 g of crude material). The crude material was suspended in water; the pH was adjusted to 5.5 by the addition of sodium bicarbonate solution and the solution formed was freeze dried. The crude sodium salt was then purified by chromatography on HP-20*. The product was eluted with water, yielding 0.52 g of product.

*HP20: A macroreticular styrene-divinylbenzene copolymer resin sold by Mitsubishi Chemical Industries Ltd.

NMR (DMSOd$_6$): δ=1.35 (s, 3H); 1.40 (s, 3H), 3.37 (dd, 1H); 3.47 (t, 2H); 3.81 (t, 2H+dd, 1H); 5.05 (m, 1H); 6.75 (s, 1H); 7.27 (s, 1H); 7.72 (s, 1H); 11.52 (broad s, 1H).

EXAMPLE 2

[3S(Z)]-2-[[[1-(2-Amino-4-thiazolyl)-2-[[1-[[[[2-[(-1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, disodium salt (A)
1,4-Dihydro-4-oxo-5-(phenylmethoxy)-2-pyridinecarboxylic acid, 2-[(1,1-dimethylethoxy)carbonyl]-hydrazide 1,4-Dihydro-4-oxo-5-(phenylmethoxy)-2-pyridinecarboxylic acid (61.3 g, 0.25 mol) was suspended in 500 ml of dimethylformamide at room temperature, followed by the addition of 39.65 g (0.3 mol) of N-(t-butoxycarbonyl)hydrazine, 1.5 g of dimethylaminopyridine and 2.0 g of N-hydroxybenzotriazole, and the mixture was stirred for 30 minutes at room temperature. Then, 57.7 g (0.28 mol) of dicyclohexylcarbodiimide, dissolved in 100 ml of dimethylformamide, was added dropwise with stirring over 30 minutes, and the mixture was stirred at room temperature overnight. The precipitate (dicyclohexylurea) was filtered off and the filtrate evaporated in vacuo. The remaining syrup crystallized on treatment with diluted sodium bicarbonate solution. The dried crude product was recrystallized from 2 liters of ethyl acetate to yield 69.5 g of the title compound, melting point 173°–175° C. A second crop was obtained after evaporation of the mother liquor; 3.2 g, melting point 160°–165° C.

(B) 1,4-Dihydro-5-hydroxy-4-oxo-2-pyridinecarboxylic acid, hydrazide 1,4-Dihydro-4-oxo-5-(phenylmethoxy)-2-pyridinecarboxylic acid, 2-[(1,1-dimethylethoxy)carbonyl]hydrazide (69 g, 0.191 mol) was added at 0° C. to 370 ml of trifluoroacetic acid. The mixture was stirred for 1 hour at room temperature, then evaporated. The remaining syrup was treated with ether to yield 68.2 g of crude 1,4-dihydro-4-oxo-5-(phenylmethoxy)-2-pyridinecarboxylic acid, hydrazide, trifluoroacetate (1:2) salt as a solid.

The crude 1,4-dihydro-4-oxo-5-(phenylmethoxy)-2-pyridinecarboxylic acid, hydrazide, trifluoroacetate (1:2) salt was dissolved in 250 ml of acetonitrile and stirred with cooling for 1 hour. The crystals were then filtered off and resuspended in 600 ml of acetonitrile. Bis(trimethylsilyl)acetamide (135 ml) was added followed by 28 g of 10% palladium on charcoal. Then hydrogen was passed through the stirred solution. The hydrogenation was complete after 90 minutes. After filtration, 70 ml of methanol and 2 ml of acetic acid were added. After stirring overnight, the crystals formed were filtered off, yielding 19.4 g of the title compound, melting point 290°–340° C., dec.

(C)

(3S)-[1-[[[[[[1,4-Dihydro-4-oxo-5-(phenylmethoxy)-2-pyridinyl]carbonyl]hydrazino]sulfonyl]amino]carbonyl]-2-oxo-3-azetidinyl]carbamic acid, phenylmethyl ester To a suspension of 5.19 g (0.0236 mol) of (S)-3-[[(phenylmethoxy)carbonyl]amino]-2-azetidinone in 160 ml of ethyl acetate was added with stirring at room temperature 2.05 g (0.0236 mol) of chlorosulfonyl isocyanate. The mixture was stirred for 1 hour at room temperature to form a solution of (S)-1-[[(chlorosulfonyl)amino]carbonyl]-3-[[(phenylmethoxy)carbonyl]amino]-2-azetidinone. The solution was cooled to 0° C., 80 ml of dichloromethane was added followed by 9.9 ml (0.0707 mol) of triethylamine and a solution of silylated 1,4-dihydro-5-hydroxy-4-oxo-2-pyridinecarboxylic acid, hydrazide (obtained from a suspension of 3.99 g (0.0236 mol) of 1,4-dihydro-5-hydroxy-4-oxo-2-pyridinecarboxylic acid, hydrazide in 50 ml of ethyl acetate and 8.75 ml of N-methyl-N-(trimethylsilyl)trifluoroacetamide (8.75 ml=0.0472 mol)). The mixture was stirred at room temperature overnight, then ice water was added and stirring was continued for an additional 30 minutes. The aqueous phase was layered with ethyl acetate and acidified to pH 2.5. The precipitate crystallized after stirring for one hour, yielding 6.6 g of the title compound.

Evaporation of the ethyl acetate phase and treatment with petroleum ether yielded a second crop of 1.4 g of the title compound.

(D)

(3S)-3-Amino-N-[[2-[(1,4-dihydro-5-hydroxy-4-oxo-2-pyridinyl)carbonyl]hydrazino]sulfonyl]-2-oxo-1-azetidinecarboxamide, trifluoroacetate (1:2) salt (3S)-[1-[[[[[[1,4-Dihydro-4-oxo-5-(phenylmethoxy)-2-pyridinyl]carbonyl]hydrazino]sulfonyl]amino]carbonyl]-2-oxo-3-azetidinyl]carbamic acid, phenylmethyl ester (6.6 g, 0.0133 mol) was added to a stirred mixture of 22 ml of trifluoroacetic acid and 5.3 ml of thioanisole at room temperature and stirred overnight at room temperature. The trifluoroacetic acid was removed in vacuo and the remaining syrup treated with ether to yield the title compound in quantitative yield.

(E)

[3S(Z)]-2-[[[1-(2-Amino-4-thiazolyl)-2-[[1-[[[[2-[-(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, diphenylmethyl ester To a solution of 5.84 g (0.0133 mol) of (Z)-2-amino-α-[[2-(diphenylmethoxy)-1,1-dimethyl-2-oxoethoxy]imino]-4-thiazoleacetic acid in 135 ml of dimethylformamide was added 5.6 ml of triethylamine and (after cooling to −30° C.) 3.57 g (0.0133 mol) of diphenyl chlorophosphate. The mixture was stirred for 1 hour at −30° C., then 3.72 ml of triethylamine was added, followed by 0.0133 mol of (3S)-3-amino-N-[[2-[(1,4-dihydro-5-hydroxy-4-oxo-2-pyridinyl)carbonyl]hydrazino]sulfonyl]-2-oxo-1-azetidinecarboxamide, trifluoroacetate (1:2) salt.

The mixture was stirred at −10° C. for 2 hours and at 0° C. for 1 hour, the solvent was removed in vacuo and the remaining syrup was treated with 150 ml of ethyl acetate and 70 ml of ice water, which was adjusted to pH 1.5–2 by the addition of 2N hydrochloric acid. The insoluble material was removed and triturated with ether to yield 5.3 g of crude product.

(F)

[3S(Z)]-2-[[1-(2-Amino-4-thiazolyl)-2-[[1-[[[[2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, disodium salt

[3S(Z)]-2-[[[1-(2-Amino-4-thiazolyl)-2-[[1-[[[[2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, diphenylmethyl ester (5.3 g, 0.0069 mol) was suspended in 10.6 ml of anisole. The suspension was cooled to −10° C. and 53 ml of trifluoroacetic acid was added with stirring. The mixture was stirred at this temperature for 1 hour, then 200 ml of ether was added at −10° C. to precipitate the trifluoroacetic acid salt of the free acid of the title compound; the yield was 7.3 g.

The crude material was dissolved in a mixture of 100 ml of water and 50 ml of acetone. The pH was adjusted to 5–5.5 and the acetone was removed in vacuo. The remaining aqueous solution was lyophilized to yield 8.1 g of crude product, which was purified by HP-20 chromatography, eluting with water. The chromatography yielded 1.05 g of product.

NMR (DMSOd$_6$): δ=1.40 (s, 3H); 1.42 (s, 3H); 3.25 (dd, 1H); 3.70 (dd, 1H); 5.10 (m, 1H); 6.75 (s, 1H); 7.40 (s, 1H); 7.80 (s, 1H); 11.32 (broad s, 1H).

EXAMPLE 3

[3S(Z)]-2-[[[1-(2-Amino-4-thiazolyl)-2-[[1-[[[3-[[(1,4-dihydro-5-hydroxy-4-oxo-2-pyridinyl)carbonyl]amino]-2-oxo-1-imidizolidinyl]sulfonyl]amino]carbonyl]-2-oxo-3-azetidinyl]amino]-2-oxoethylidene]amino]oxy]-2-acetic acid, disodium salt (A)

[3S(Z)]-2-[[[1-(2-Amino-4-thiazolyl)-2-[[1-[[[3-[[(1,4-dihydro-5-hydroxy-4-oxo-2-pyridinyl)carbonyl]amino]-2-oxo-1-imidizolidinyl]sulfonyl]amino]carbonyl]-2-oxo-3-azetidinyl]amino]-2-oxoethylidene]amino]oxy]-2-acetic acid, diphenylmethyl ester To a solution of 2.06 g (0.005 mol) of (Z)-2-amino-α-[[2-(diphenylmethoxy)-2-oxoethoxy]imino]-4-thiazoleacetic acid in 100 ml of dimethylformamide was added 2.1 ml (0.015 mol) of triethylamine. The mixture was cooled to −30° C. and 1.1 ml of diphenyl chlorophosphate (0.005 mol) was added with stirring. After stirring for 1 hour at −30° C., an additional 1.4 ml of triethylamine (0.1 mol) was added at −30° C., followed by 2.7 g of (3S)-3-amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, trifluoroacetate (1:2) salt.

The reaction mixture was stirred at −10° C. for 2 hours and at 0° C. for 1 hour. The solvent was evaporated off in vacuo, the oily residue suspended in water and the pH of the suspension adjusted to 2 by the addition of 2N hydrochloric acid. The suspension was stirred for 30 minutes at room temperature, filtered off, the solid resuspended in water and filtered off again. After drying in vacuo over phosphorous pentoxide, 5.0 g of crude product were obtained. The material was used in the next step without further purification.

(B)

[3S(Z)]-2-[[[1-(2-Amino-4-thiazolyl)-2-[[1-[[[[3-[[(1,-4-dihydro-5-hydroxy-4-oxo-2-pyridinyl)carbonyl-]amino]-2-oxo-1-imidizolidinyl]sulfonyl]amino]carbonyl]-2-oxo-3-azetidinyl]amino]-2-oxoethylidene]amino]oxy]-2-acetic acid, disodium salt 5.0 g of crude [3S(Z)]-2-[[[1-(2-amino-4-thiazolyl)-2-[[1-[[[[3-[[(1,4-dihydro-5-hydroxy-4-oxo-2-pyridinyl)carbonyl]amino]-2-oxo-1-imidizolidinyl]sulfonyl]amino]carbonyl]-2-oxo-3-azetidinyl]amino]-2-oxoethylidene]amino]oxy]-2-acetic acid, diphenylmethyl ester were suspended at −10° C. in a mixture of 10 ml of anisole and 50 ml of trifluoroacetic acid. The reaction mixture was stirred at −10° C. for 1 hour, followed by the careful addition of 100 ml of ether to precipitate the crude trifluoroacetate salt of the title compound. Yield 3.7 g. The crude material was dissolved in a mixture of 30 ml of water and 60 ml of acetone, and the pH of the mixture was adjusted to 5–5.5 by the addition of 0.1 N sodium hydroxide. The acetone was evaporated and the aqueous phase was lyophilized to yield 3.9 g of crude product. The crude material was purified by chromatography on HP-20. The product was eluted with water (fractions of 10 ml each). The fractions containing product were lyophilized to yield 0.6 g of material which was rechromatographed on HP-20 to yield 0.25 g of pure product.

EXAMPLE 4

[3S(Z)]-2-[[[1-(2-Amino-4-thiazolyl)-2-[[1-[[[[(1,4-dihydro-5-hydroxy-4-oxo-2-pyridinyl)methyl]amino]-sulfonyl]amino]carbonyl]-2-oxo-3-azetidinyl]amino]-2-oxoethylidene]amino]oxy]-2methylpropanoic acid (A)

2-(Hydroxymethyl)-5-(phenylmethoxy)-4(1H)-pyridinone

A mixture of 2-(hydroxymethyl)-5-(phenylmethoxy)-4H-pyran-4-one (9.65 g, 41.59 mole), 95 ml of concentrated ammonia and 20 ml of ethanol were heated at reflux overnight. An additional 75 ml of ammonium hydroxide was added, the mixture was refluxed for 2 hours and cooled. The resulting brown solid was filtered and washed with water until the washings were neutral. The crude product was suspended in ethanol, filtered, washed with ethanol and hexane and dried in vacuo. The yield of the title compound was 7.61 g.

(B)

2-(Chloromethyl)-5-(phenylmethoxy)-4(1H)pyridinone, monohydrochloride

A suspension of 2-(hydroxymethyl)-5-(phenylmethoxy)-4(1H)-pyridinone (3 g, 12.99 mmole) in chloroform (15 ml) was cooled to 0° under argon and treated with thionyl chloride (6.1 ml, 83.62 mmole). Within several minutes, a homogeneous solution was obtained. After stirring an additional 5 minutes, a cream colored solid precipitated. The cooling bath was removed and the mixture was heated at reflux for 45 minutes. The mixture was cooled to 0° and the white precipitate was filtered, washed with chloroform and hexane and dried in vacuo. The yield of the title compound was 3.65 g.

(C)

2-(Azidomethyl)-5-(phenylmethoxy)-4(1H)-pyridinone

A mixture of 2-(chloromethyl)-5-(phenylmethoxy)-4(1H)-pyridinone, monohydrochloride (3.59 g, 12.54 mmole), sodium azide (4.08 g, 62.7 mmole) and diisopropylethylamine (2.19 ml, 12.54 mmole) in 70 ml of dimethylformamide was stirred at room temperature under argon for 3.5 days. An additional 4.08 g of sodium azide was added and the mixture was heated at 45°–50° C. for 2 hours. After cooling, the reaction mixture was poured into 500 ml of water, producing an insoluble white solid. The pH of the supernatant liquid was lowered from 8.5 to 7.5 with dilute hydrochloric acid, and the white solid was filtered. After washing with water, acetone, and hexane the solid was dried in vacuo. The yield of the title compound was 2.81 g.

(D)

2-(Azidomethyl)-4-(phenylmethoxy)-4(1H)-pyridinone

A mixture of 2-(azidomethyl)-5-(phenylmethoxy)-4(1H)-pyridinone (2.03 g, 7.93 mmol) and platinum oxide (200 mg) in 100 ml of dimethylformamide was stirred for 6 hours at room temperature under one atmosphere of hydrogen. The catalyst was removed by filtration and the solution was concentrated in vacuo to afford 1.5 g (82% yield) of the title compound as a grey powder.

(E)

(3S)-[1-[[[[[[1,4-Dihydro-4-oxo-5-(phenylmethoxy)-2-pyridinyl]methyl]amino]sulfonyl]amino]carbonyl]-2-oxo-3-azetidinyl]carbamic acid, phenylmethyl ester To a stirred suspension of 2-(aminomethyl)-5-(phenylmethoxy)-4(1H)-pyridinone (2.330 g, 10.13 mmole) in 60 ml ethyl acetate was added N-methyl-N-(trimethylsilyl)trifluoroacetamide (3.76 ml, 20.26 mmole). The resulting solution was stirred for 30 minutes at room temperature and then cooled to 0° C. Concurrently, to a stirred suspension of (S)-3-[[(phenylmethoxy)carbonyl]amino]-2-azetidinone (2.228 g, 10.13 mmole) in 60 ml ethyl acetate was added chlorosulfonyl isocyanate (882 μl, 10.13 mmol). The resulting solution was stirred for 30 minutes at room temperature, cooled to 0° C., and finally treated with triethylamine (4.23 ml, 30.39 mmole) followed by the solution of silylated 2-(aminomethyl)-5-(phenylmethoxy)-4(1H)-pyridinone described above. The mixture was stirred for two days at room temperature.

The mixture was concentrated in vacuo, the residue dissolved in CH₃CN-water (40–60) and the pH lowered to 2.9 whereupon a thick oil separated. Upon cooling to 5° C., the oil solidified. The solid was separated, washed four times with water, and dried in vacuo to afford 3.4 g crude product. The crude product was dissolved in a minimum volume of dimethylformamide and loaded on a column (1 l) of HP-20 resin. The column was eluted with a stepwise acetone-water gradient Desired material eluted with ca. 65% acetone. The relevant fractions were combined and lyophilized to afford 2.69 g of the title compound.

(F)

[3S(Z)]-2-[[[1-(2-Amino-4-thiazolyl)-2-[[1-[[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid, diphenylmethyl ester (as a mixture of monopotassium and monotriethylammonium salts)

A mixture of (3S)-[1-[[[[[[1,4-dihydro-4-oxo-5-(phenylmethoxy)-2-pyridinyl]methyl]amino]sulfonyl]amino]carbonyl]-2-oxo-3-azetidinyl]carbamic acid, phenylmethyl ester (912 mg, 1.64 mmole), p-toluenesulfonic acid monohydrate (625 mg, 3.28 mmole), and 10% palladium on charcoal (190 mg) in 16 ml of dimethylformamide was stirred under one atmosphere of hydrogen until 3.28 mmole (73 ml) of hydrogen was consumed (ca. 3 hours).

To a stirred solution of (Z)-2-amino-α-[[2-(diphenylmethoxy)-1,1-dimethyl-2-oxoethoxy]imino]-4-thiazoleacetic acid (846 mg, 1.804 mmole) in 6 ml of dimethylformamide at −20° C. was added diphenyl chlorophosphate (374 μl, 1.804 mmole) followed by triethylamine (450 μl, 3.28 mmole). The solution was stirred for 1 hour at −20° C. whereupon the above-described mixture of hydrogenolyzed (3S)-[1-[[[[[[1,4-dihydro-4-oxo-5-(phenylmethoxy)-2-pyridinyl]methyl]amino]sulfonyl]amino]carbonyl]-2-oxo-3-azetidinyl]-carbamic acid, phenylmethyl ester was added. The resulting mixture was stirred at −20° C. for one hour and then at 5° C. overnight. The catalyst was removed by filtration, volatiles were removed in vacuo and the resulting oil was dissolved in a minimum volume of acetone-water (75–25, pH 5.2) and added dropwise to a stirred suspension of 20 ml of Dowex 50x2-400* (K+) in acetone-water 35–65. After 40 minutes, the mixture was filtered and the filtrate lyophilized to afford 2.1 g of solid. The solid was dissolved in a minimum amount of acetonitrile-water (40–60, pH 5.6) and loaded onto a column (800 ml) of HP-20 resin, eluting with a stepwise acetonitrile-water gradient. Desired material eluted with ca. 30% acetonitrile. The relevant fractions were combined and lyophilized to afford the impure title compound (254 mg).
*Dowex 50x2-400: Styrene-divinylbenzene copolymer gel with —SO₃— groups attached sold by Dow Chemical Co.

(G)

[3S(Z)]-2-[[[1-(2-Amino-4-thiazolyl)-2-[[1-[[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid Trifluoroacetic acid (4.7 ml) was added dropwise to a stirred suspension of the above impure [3S(Z)]-2-[[[1-(2-amino-4-thiazolyl)-2-[[1-[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid, diphenylmethyl ester (mixture of monopotassium and monotriethylammonium salts) (131 mg) in 3 ml dichloromethane and 0.3 ml anisole at 0° C. After stirring 45 minutes at 5° C., 2 ml of toluene was added and the volatiles were removed in vacuo. The resulting oil was washed with hexane (3×4 ml) and triturated to a solid with 10 ml ether. The solid was washed once with ether (10 ml) and dried in vacuo. The above reaction and work-up were repeated on 166 mg of [3S(Z)]-2-[[[1-(2-amino-4-thiazolyl)-2-[[1-[[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2methylpropanoic acid, diphenylmethyl ester (mixture of monopotassium and monotriethylammonium salts). The crude products were combined, dissolved in 2 ml CH₃CN-water 40–60 (pH 2.5) and chromatographed on a column (200 ml) HP-20 resin, using an acetonitrile-water gradient. The desired material eluted at CH₃CN-water 20–80. The relevant fractions were combined and lyophilized to afford 103 mg [3S(Z)]-2-[[[1-(2-amino-4--thiazolyl)-2-[[1-[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid as a white solid.

EXAMPLE 5

[3S(Z)]-2-[[[1-(2-Amino-4-thiazolyl)-2-[[1-[[[2-[[2-[-(1,4-dihydro-5-hydroxy-4-oxo-2-pyridinyl)carbonyl]hydrazino]carbonyl]hydrazino]sulfonyl]amino]carbonyl]-2-oxo-3-azetidinyl]amino]-2-oxoethylidene]amino]oxy]-2-methylpropanoic acid, di sodium salt (A)

1,4-Dihydro-4-oxo-5-(phenylmethoxy)-2-pyridinecarboxylic acid, 2-[[(4-methoxyphenyl)methoxy]-carbonyl]hydrazide A solution of 4.54 g (0.022 moles) dicyclohexylcarbodiimide in 25 ml dry of dimethylformamide was added to a stirred suspension of 4.90 g (0.020 moles) of 1,4-dihydro-4-oxo-5-(phenylmethoxy)-2-pyridinecarboxylic acid, 4.50 g (0.022 moles) of 4-methoxybenzyl carbazate, 0.12 g (1.0 mmol) of 4-dimethylamino-pyridine and 0.155 g (1.0 mmol) of 1-hydroxybenzotriazole hydrate in 25 ml of dry dimethylformamide at room temperature and stirring was continued overnight. The precipitate was filtered off and the filtrate was evaporated in vacuo. The residue solidified by stirring with ether and aqueous sodium bicarbonate and the solid was collected, washed with water and finally dried in vacuo. The crude material (8.14 g) was extracted in a soxhlet-apparatus with 800 ml CHCl₃ (7 hours). 5.70 g (67%) of pure 1,4-dihydro-4-oxo-5-(phenylmethoxy)-2-pyridinecarboxylic acid, 2-[[(4-methoxyphenyl)methoxy]carbonyl]hydrazide crystallized directly from the cold CHCl₃-extract, and an additional impure amount (1.5 g, 18%) of the title compound could be obtained by evaporation of the CHCl₃-solution in vacuo; melting point 174.5°–178° C.

(B)

1,4-Dihydro-4-oxo-5-(phenylmethoxy)-2pyridinecarboxylic acid, hydrazide, trifluoroacetate (1:2) salt A −10° C. solution of 3.81 ml (35.04 mmol) of anisole in 38 ml of trifluoroacetic acid was added to an ice-cold suspension of 3.71 g (8.76 mmol) of 1,4-dihydro-4-oxo-5-(phenylmethoxy)-1-pyridinecarboxylic acid, 2-[[(4methoxyphenyl)methoxy]carbonyl]hydrazide in 15 ml dry dichloromethane. After stirring at 0° C. for 20 minutes, the solution was evaporated in vacuo to leave the title compound as a solid which was stirred with few mls of dry ether, collected by suction and dried in vacuo. Yield: 3.25 g (99%); melting point 173°–175° C., dec.

(C)

1,4-Dihydro-4-oxo-5-(phenylmethoxy)-2pyridinecarboxylic acid, hydrazide 3.84 ml (19.64 mmol) of N-methyl-N-(trimethylsilyl)-trifluoroacetamide was added to a suspension of 3.19 g (8.55 mmol) of 1,4-dihydro-4-oxo-5-(phenylmethoxy)-2-pyridinecarboxylic acid, hydrazide, trifluoroacetate (1:2) salt in 35 ml dry acetonitrile and stirring was continued for 30 minutes at room temperature. After evaporation in vacuo, the residue was taken up in ether, followed by a dropwise addition of 1 ml methanol. The precipitate was collected by suction, washed with ether and petroleum ether and dried in vacuo to yield 2.05 g (92%) of the title compound (melting point 204°–208° C., dec.).

(D)
1,4-Dihydro-4-oxo-5-(phenylmethoxy)-2-pyridinecarboxylic acid, 2-[[2-(phenylmethoxy)carbonyl]hydrazino]carbonyl]-hydrazide With cooling, 11.69 ml (0.060 mol) N-methyl-N-trimethylsilyltrifluoroacetamide was added to a suspension of 5.19 g (0.020 mol) of 1,4-dihydro-4-oxo-5-(phenylmethoxy)-2-pyridinecarboxylic acid, hydrazide in 20 ml dry acetonitrile, and stirring was continued for 30 minutes at room temperature. The clear solution was evaporated in vacuo, and the residue was redissolved in 30 ml dry dichloromethane. Then this solution was added dropwise to a stirred solution of 4.57 g (0.020 mol) of

(J. Gante, Chem. Ber. 97, 2551 (1964) in 60 ml of dichloromethane at 0°–5° C. After being stirred at this temperature for 2.5 hours, the solution was evaporated in vacuo and the solid foam was redissolved in 20 ml methanol Evaporation in vacuo gave the title compound as a solid foam which became crystalline by stirring with dry ether. Yield 8.87 g (98%); melting point >120° C., dec.

(E) 1,4-Dihydro-5-hydroxy-4-oxo-2-pyridinecarboxylic acid, 2-(hydrazinocarbonyl)hydrazide, dihydrochloride A solution of 4.02 g (8.9 mmol) 1,4-dihydro-4-oxo-5-(phenylmethoxy)-2-pyridinecarboxylic acid, 2-[[2-(phenylmethoxy)carbonyl]hydrazino]carbonyl]hydrazide in 50 ml methanol containing 2.94 ml (35.6 mmol) conc. hydrochloric acid was hydrogenated in the presence of 0.4 g palladium (10%) on carbon for 10 minutes. The catalyst was filtered off and the solvent was distilled off in vacuo to leave the title compound as a solid (2.58 g) which was stirred with few ml dry ether, collected by suction and dried in vacuo. Yield: 2.47 g (92%); melting point 235°–236° C., dec.

(F)
(3S)-[1-[[[[2-[2-[(1,4-Dihydro-5-hydroxy-4-oxo-2-pyridinyl)carbonyl]hydrazino]carbonyl]hydrazino]sulfonyl]amino]carbonyl]-2-oxo-3-azetidinyl]carbamic acid, phenylmethyl ester 4.86 ml (25.0 mmol) of N-methyl-N-trimethylsilyltrifluoroacetamide was added to a suspension of 1.5 g (5.0 mmol) of 1,4-dihydro-5-hydroxy-4-oxo-2-pyridinecarboxylic acid, 2-(hydrazinocarbonyl)hydrazide, dihydrochloride in 20 ml of dry acetonitrile. After stirring for 45 minutes at room temperature, the clear solution was evaporated in vacuo, and the residue was dissolved in 20 ml of dry ethyl acetate (Solution A).

To a suspension of 1.10 g (5.0 mmmol) of (S)-3-[[(phenylmethoxy)carbonyl]amino]-2-azetidinone in 40 ml dry ethyl acetate was added 0.45 ml (5.0 mmol) of chlorosulfonyl isocyanate with stirring, and the mixture was stirred for 1 hour at room temperature and then cooled to 0° C. After the addition of 10 ml of dry dichloromethane and 2.09 ml (15.0 mmol) of triethylamine, Solution A was dropped in with stirring at 0° C. After stirring overnight at 0° C., the reaction mixture was poured into ice water and the organic layer was separated. Acidification of the aqueous phase to pH 2 by the addition of 1N hydrochloric acid gave the title compound as a sticky precipitate which was collected by suction, washed with water and dried in vacuo. Yield: 1.76 g (64%).

(G)
(3S)-3-Amino-N-[2-[[2-[(1,4-dihydro-5-hydroxy-4-oxo-2-pyridinyl)carbonyl]hydrazino]carbonyl]hydrazino]-sulfonyl]-2-oxo-1-azetidinecarboxamide, trifluoroacetate (1:2) salt At 0° C. 1.73 g (3.1 mmol) of (3S)-[1-[[[[2-[2-[(1,4-Dihydro-5-hydroxy-4-oxo-2-pyridinyl)carbonyl]hydrazino]carbonyl]hydrazino]sulfonyl]amino]carbonyl]-2-oxo-3-azetidinyl]carbamic acid, phenylmethyl ester were added to a mixture of 5.13 ml trifluoroacetic acid and 1.21 ml thioanisole. After stirring overnight at room temperature, the solution was evaporated in vacuo and the residue was stirred with dry dichloromethane. The precipitate was collected by suction, washed with dichloromethane and dried in vacuo to yield 1.78 g (88%) of the title compound.

(H)
[3S(Z)]-2-[[[1-(2-Amino-4-thiazolyl)-2-[[1-[[[[2-[[2-(1,4-dihydro-5-hydroxy-4-oxo-2pyridinyl)carbonyl]hydrazino]carbonyl]hydrazino]sulfonyl]amino]carbonyl]-2-oxo-3-azetidinyl]amino]-2-oxoethylidene]amino]oxy-2-methylpropanoic acid, diphenylmethyl ester Into a −30° C. solution of 1.10 g (2.5 mmol) of (Z)-2-amino-α-[(2-diphenylmethoxy)-1,1-dimethyl-2-oxoethoxy]imino]-4-thiazoleacetic acid in 22 ml of dry dimethylformamide was added 1.05 ml (7.5 mmol) of triethylamine followed by 0.53 ml (2.5 mmol) of diphenyl chlorophosphate. After stirring at −30° C. for 1 hour, 1.05 ml (7.5 mmol) of triethylamine was dropped in, followed by the addition of 1.62 g (2.5 mmol) of (3S)-3-amino-N-[[2-[[2-[(1,4-dihydro-5-hydroxy-4-oxo-2pyridinyl]carbonyl]hydrazino]carbonyl]hydrazino]-sulfonyl]-2-oxo-1-azetidinecarboxamide, trifluoroacetate (1:2) salt. The mixture was stirred for 2 hours at −10° C. and for an additional hour at 0° C. The solvent was removed in vacuo and the residue was taken up in few ml of ethyl acetate and ice water. The pH of the mixture was adjusted to pH=2 by the addition of dilute hydrochloric acid. The insoluble material was collected by suction and stirred with few ml ethyl acetate until it became crystalline to yield after drying in vacuo 1.72 g (82%) of the title compound.

(I)
[3S(Z)]-2-[[[1-(2-Amino-4-thiazolyl)-2-[[1-[[[[2-[[2--[(1,4-dihydro-5-hydroxy-4-oxo-2pyridinyl)carbonyl]-hydrazino]carbonyl]hydrazino]sulfonyl]amino]carbonyl]-2-oxo-3-azetidinyl]amino]-2-oxoethylidene]amino]oxy-2-methylpropanoic acid, disodium salt To a suspension of 1.68 g (2.0 mmol) of crude [3S(Z)]--2-[1-(2-amino-4-thiazolyl)-2-[[1-[[[[2-[[2-[(1,4-dihydro-5-hydroxy-4-oxo-2pyridinyl)carbonyl]hydrazino]-carbonyl]hydrazino]sulfonyl]amino]carbonyl]-2-oxo-3-azetidinyl]amino]-2-oxoethylidene]amino]oxy]-2-methylpropanoic acid, diphenylmethyl ester in 3 ml of dry dichloromethane was added 2.0 ml of anisole followed by 20 ml of trifluoroacetic acid at −10° . After stirring at 0° C. for 10 minutes, the solvent was removed in vacuo at 0°–5° C. The residue was taken up in ice water and ether and the pH was adjusted to 6.0 by the addition of dilute sodium hydroxide (1%). The organic phase and insoluble material (0.38 g) were separated and the aqueous phase was freeze dried (2.66 g). The residue from lyophilization was purified on XAD-2 resin* (eluting with water) to yield upon lyophilization 0.25 g (17%) of the title compound as a colorless powder (melting point >213° C., dec.).
*XAD-2 resin: Macroreticular styrene-divinylbenzene copolymer resin sold by Rohm and Haas Company.

EXAMPLE 6
[3S-[3α(Z),4β]]-2-[[[1-(2-amino-4-thiazolyl)-2-[[1-[[ [[2-[(1,4-dihydro-5-hydroxy-4-oxo-2-pyridinyl)carbonyl]hydrazino]sulfonyl]amino]carbonyl]-4-methyl-2-oxo-3-azetidinyl]amino]-2-oxoethylidene]amino]oxy]-2-methylpropionic acid, disodium salt (A)
(3S-trans)-[1-[[[[2-[[1,4-Dihydro-4-oxo-5-hydroxy-2-pyridinyl]carbonyl]hydrazino]sulfonyl]amino]carbonyl]-4-methyl-2-oxo-3-azetidinyl]carbamic acid, phenylmethyl ester To a suspension of 2.34 g of (3S-trans)-(4-methyl-2-oxo-3-azetidinyl)carbamic acid, phenylmethyl ester in 50 ml of dry ethyl acetate was added 1.41 g of chlorosulfonyl isocyanate. After stirring for 1 hour at room temperature, a clear solution was formed (Solution A).

To a suspension of 1.70 g of 1,4-dihydro-5-hydroxy-4-oxo-2-pyridinecarboxylic acid, hydrazide in 50 ml of dry ethyl acetate was added 6 g of N-methyl-N-(trimethylsilyl)trifluoroacetamide. After stirring at 50° C. for 1 hour, a clear solution formed (Solution B).

After cooling to −10° C., Solution B was added to Solution A, and the mixture was stirred overnight at room temperature. Upon cooling to −15°, 3 g of triethylamine was added, followed by 150 ml of ice water. After stirring for 1 hour at 0°, the organic phase was washed with 50 ml of water. The combined water phases were adjusted to pH 2 with 1N HCl and extracted three times with 100 ml of ethyl acetate. The combined organic phases were dried and the solvent was evaporated to yield 3.64 g of the title compound.

(B) (3S-trans)-3-Amino-N-[[2-[(1,4-dihydro-5-hydroxy-4-oxo-2-pyridinyl)carbonyl]hydrazino]sulfonyl]-4-methyl-2-oxo-1-azetidinecarboxamide, trifluoroacetate (1:2) salt To 3.5 g of (3S-trans)-[1-[[[[2-[[1,4-dihydro-4-oxo-5-hydroxy-2-pyridinyl]carbonyl]hydrazino]sulfonyl]amino]carbonyl]-4-methyl-2-oxo-3-azetidinyl]carbamic acid, phenylmethyl ester in 20 ml of thioanisole was added 50 ml of trifluoroacetic acid at room temperature, and the reaction was then stirred for 13 hours. After addition of 100 ml of ether, 3.2 g of a crude precipitate was obtained. This precipitate was then stirred for 1 hour in 50 ml of isopropanol/methylene chloride (1:1) to yield 2.21 g of the title compound.

(C)
[3S-[3α(Z),4β]]-2-[[[1-(2-amino-4-thiazolyl)-2-[[ 1-[[[[2-(1,4-dihydro-5-hydroxy-4-oxo-2-pyridinyl)carbonyl]hydrazino]sulfonyl]amino]carbonyl]-4-methyl-2-oxo-3-azetidinyl]amino]-2-oxoethylidene]amino]oxy]-2-methylpropionic acid, diphenylmethyl ester To a solution of 1.8 g of (Z)-2-amino-α-[[2-diphenylmethoxy)-1,1-dimethyl-2-oxoethoxy]imino]-4-thiazoleacetic acid and 1.2 g of triethylamine in 30 ml of dimethylformamide at −30° were added 2.1 g of diphenyl chlorophosphate. After stirring at −30° for 45 minutes, 1.95 g of (3S-trans)-3-amino-N-[[2-[(1,4-dihydro-5-hydroxy-4-oxo-2-pyridinyl)carbonyl]hydrazino]-sulfonyl]-4-methyl-2-oxo-1-azetidinecarboxamide, trifluoroacetate (1:2) salt in 10 ml of dimethylformamide was added, followed by 0.8 g of triethylamine. After stirring at −10° C. for 2 hours and at 0° C. for 1 hour, the dimethylformamide was removed in vacuo, the residue was stirred with 250 ml of ethyl acetate and 400 ml of ice water. The water phase was adjusted to pH 1.5 with 2N HCl and was extracted twice with 200 ml portions of ethyl acetate. The organic phase was dried over sodium sulfate and evaporated to yield 1.3 g of the crude title compound.

(D)
[3S-[3α(Z),4β]]-2-[[[1-(2-amino-4-thiazolyl)-2-[[1-[ [[[2-[(1,4-dihydro-5-hydroxy-4-oxo-2-pyridinyl)carbonyl]hydrazino]sulfonyl]amino]carbonyl]-4-methyl-2-oxo-3-azetidinyl]amino]-2-oxoethylidene]amino]oxy]-2-methylpropionic acid, disodium salt To a solution of 1.2 g of [3S-[3α(Z),4β]]-2-[[[1-(2-amino-4-thiazolyl)-2-[[1-[[[[2-[(1,4-dihydro5-hydroxy-4-oxo-2-pyridinyl)carbonyl]hydrazino]sulfonyl]amino]-carbonyl]-4-methyl-2-oxo-3-azetidiny l]amino]-2-oxoethylidene]amino]oxy]-2-methylpropionic acid, diphenylmethyl ester in a mixture of 10 ml methylene chloride and 15 ml of anisole was added 30 ml of trifluoroacetic acid at −5° C. After stirring for 30 minutes, 100 ml of ether was added to give 0.8 g of precipitate. This precipitate was suspended in 20 ml of water and the pH was adjusted to 6.5 with sodium bicarbonate. The clear solution was then chromatographed on XAD-2 with water as the eluent to give 0.28 g of pure title compound.

EXAMPLE 7

[3S(Z)]-1-[[[1-(2-Amino-4-thiazolyl)-2-[[1-[[[[3-[[(1,-4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]cyclopentanecarboxylic acid, disodium salt (A)

[3S(Z)]-1-[[[1-(2-Amino-4-thiazolyl)-2-[[1-[[[[3-[[(1,-4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]cyclopentanecarboxylic acid, diphenylmethyl ester To a suspension of 3.9 g (8.3 mmol) of (Z)-2-amino-α-[[[1-(diphenylmethoxy)carbonyl]cyclopentyl]oxy]imino]-4-thiazoleacetic acid in 100 ml of dry acetonitrile were added 3.5 ml (25 mmol) of triethylamine to form a clear solution. After cooling to −30° C., 1.8 ml (8.3 mmol) of diphenyl chlorophosphate were added, and the mixture was stirred at −30° C. for 1 hour (Solution A).

At the same time, 4.5 g (8.3 mmol) of (3S)-3-amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, trifluoroacetate (1:2) salt were suspended in 100 ml of dry ethyl acetate. Then, 7.2 ml of bis(trimethylsilyl)acetamide were added at room temperature to give a clear solution after 5 minutes. After stirring for 1 hour, the solution was cooled to 0° (Solution B).

Solution B was added dropwise with stirring to Solution A at −30° over 10 minutes. The mixture was stirred for 1 hour at −10° C. and for 1.5 hour at 0°. The volatiles were evaporated, and the residue was triturated with water. The residue solidified, and the solids were collected and resuspended in water at approximately pH 2. After stirring for 30 minutes, the solid was collected and dried to give 12.0 g of the crude title compound.

(B)

[3S(Z)]-1-[[[1-(2-Amino-4-thiazolyl)-2-[[1-[[[[3-[[(1,-4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]cyclopentanecarboxylic acid, disodium salt Crude [3S(Z)]-1-[[[1-(2-amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]cy clopentanecarboxylic acid, diphenylmethyl ester (12 g) was suspended in 20 ml of anisole, and, upon cooling to −10° C., 100 ml of trifluoroacetic acid was added. The mixture was stirred at −10° C. for 1 hour, and 300 ml of ether was added at −10° to yield a precipitate. After stirring for 1 hour, the precipitate was filtered off to give 5.7 g of material. This material was dissolved in a mixture of 30 ml of water and 60 ml of acetone and the pH of the solution was adjusted to 5.5 by the addition of 0.1N NaOH at 0° with stirring. The acetone was evaporated in vacuo, and the aqueous solution was freeze-dried to yield 5.7 g of a solid residue. This residue was chromatographed on HP-20 (eluting with water) to yield 1.69 g (27%) of pure title compound.

$^1$H-NMR (DMSO-d$_6$+CF$_3$COOH): δ=1.67 (s, 4H); 2.07 (2, 4H); 3.65 (t, 2H); 3.75 (dd, 1H); 3.97 (dd, 1H); 4.07 (t, 2H); 5.07 (dd, 1H); 7.00 (s, 1H); 7.67 (s, 1H); 8.07 (s, 1H); ppm.

EXAMPLE 8

[3S(Z)]-2-[[[1-(2-Amino-4-thiazolyl)-2-[[1-[[[[3-[(1,4-dihydro-5-hydroxy-4-oxo-2-pyridinyl)methyl]-2-oxo-1-imidazolidinyl]sulfonyl]amino]carbonyl]2-oxo-3-azetidinyl]amino]-2-oxoethylidene]amino]oxy]-2-methylpropanoic acid, disodium salt (A)

2-(Azidomethyl)-5-(phenylmethoxy)-1-(phenylmethyl)-4(1H)-pyridinone

To a suspension of 2.0 g (6 mmol) of 2-(chloromethyl)-5-(phenylmethoxy)-1-(phenylmethyl)-4(1H)-pyridinone in 20 ml of acetonitrile was added 3.9 g (60 mmol) of sodium azide and 0.1 g of 18-crown-6, and the mixture was heated to reflux for four hours. The salts were filtered off by suction, and the filtrate was evaporated in vacuo. The residue was purified by column chromatography on silica gel (ethyl acetate-methanol 8:2) yielding 1.86 g of the title compound, melting point 120° C.

(B)

2-(Aminomethyl)-5-(phenylmethoxy)-1-(phenylmethyl)-4(1H)-pyridinone 2-(Azidomethyl)-5-(phenylmethoxy)-1-(phenylmethyl)-4(1H)-pyridinone (1.0 g, 2.89 mmol) was dissolved in 50 ml of methanol and 0.10 g of platinic oxide was added. Hydrogen was bubbled through the mixture for 30 minutes and the catalyst filtered off by suction over Hyflo. The filtrate was evaporated in vacuo and the oily residue triturated with ether to afford crystalline title compound (0.89 g), melting point 207° C.

(C)

2-[[[[(2-Chloroethyl)amino]carbonyl]amino]methyl]-5-(phenylmethoxy)-2-(phenylmethyl)-4(1H)-pyridinone To a suspension of 48.0 g (0.15 mol) of 2-(aminomethyl)-5-(phenylmethoxy)-1-(phenylmethyl)-4(1H)-pyridinone in 1.5 l of ethyl acetate was added 12.8 ml (0.15 mol) of 2-chloroethylisocyanate. The mixture was stirred overnight at room temperature, the product filtered off by suction, washed with ethyl acetate, and dried in vacuo, yielding 59.6 g of the title compound, melting point 130° C.

(D)

2-[(2-Oxo-1-imidazolidinyl)methyl]-5-(phenylmethoxy)-1-(phenylmethyl)-4(1H)-pyridinone A solution of 7.29 g (0.13 mol) of potassium hydroxide in 500 ml of ethanol was added dropwise to a mixture of 60.8 g (0.13 mol) of 2-[[[[(2-chloroethyl)amino]carbonyl]amino]methyl]-5-(phenylmethoxy)-2-(phenylmethyl)-4(1H)-pyridinone and 1.3 l of ethanol. The reaction mixture was heated to reflux for three hours and the solvent evaporated in vacuo. The residue was purified by column chromatography on silica gel using a mixture of ethyl acetate and methanol (7:3) as eluent, yielding 23.1 g of product, which was further purified by recrystallization from acetonitrile, yielding 17.0 g of the title compound, melting point 190° C., dec.

(E)
5-Hydroxy-2-[(2-oxo-1-imidazolidinyl)methyl]--4(1H)-pyridinone, p-toluenesulfonate salt To a solution of 2-[(2-oxo-1-imidazolidinyl)methyl]-5-(phenylmethoxy)-1-(phenylmethyl)-4(1H)pyridinone (4.98 g; 12.8 mmol) in dimethylformamide (90 ml) was added p-toluenesulfonic acid monohydrate (4.86 g; 25.6 mmol) and palladium on charcoal (1.0 g), and hydrogen was bubbled through the mixture for 30 minutes. The catalyst was filtered off by suction and the filtrate evaporated in vacuo. The residue was triturated with dichloromethane and ether, and the product filtered off by suction, yielding 4.12 g of the title compound, melting point 195° C.

(F)
5-Hydroxy-2-[(2-oxo-1-imidazolidinyl)methyl]--4(1H)-pyridinone

5-Hydroxy-2-[(2-oxo-1-imidazolidinyl)methyl]-4(1H)-pyridinone, p-toluenesulfonate salt (4.0 g; 10.5 mmol) was dissolved in water (50 ml), and the pH was adjusted to 6.5 by the addition of 2N sodium hydroxide. The precipitate was filtered off by suction, washed with water, and dried in vacuo, yielding 1.5 g of the title compound, melting point 280° C., dec.

(G)
(S)-[1-[[[[3-[(1,4-Dihydro-5-hydroxy-4-oxo-2-pyridinyl)methyl]-2-oxo-1-imidazolidinyl]sulfonyl]amino]carbonyl]-2-oxo-3-azetidinyl]carbamic acid, phenylmethyl ester 1.10 g (5 mmol) of (S)-3-[[(phenylmethoxy)carbonyl]amino]-2-azetidinone was suspended in 20 ml of dry ethyl acetate, and 0.44 ml (5 mmol) of chlorosulfonyl isocyanate added. The mixture was stirred at room temperature for one hour (solution A).

To a suspension of 1.04 g (5 mmol) of 5-hydroxy-2-[(2-oxo-1-imidazolidinyl)methyl]-4(1H)pyridinone in 10 ml of dry ethyl acetate was added 3.70 ml (20 mmol) of N-methyl-N-(trimethylsilyl)trifluoroacetamide, and the mixture was heated to 60° C. The resulting clear solution was evaporated in vacuo at 60° C. and the residue dissolved in 10 ml of dry ethyl acetate (solution B).

Solution (B) was added to solution (A) and the reaction mixture stirred overnight at room temperature. The solvent was removed in vacuo and the residue triturated with ether, yielding 2.91 g of the title compound, melting point 180° C., dec.

(H)
(S)-3-Amino-N-[[3-[(1,4-dihydro-5-hydroxy-4-oxo-2-pyridinyl)methyl]-2-oxo-1-imidazolidinyl]sulfonyl]-2-oxo-1-azetidinecarboxamide, trifluoroacetate salt (S)-[1-[[[[3-[(1,4-Dihydro-5-hydroxy-4-oxo-2-pyridinyl)methyl]-2-oxo-1-imidazolidinyl]sulfonyl]amino]carbonyl]-2-oxo-3-azetidinyl]carbamic acid, phenylmethyl ester (0.50 g, 0.93 mmol) was added to a mixture of 0.5 ml of thioanisole and 2 ml of trifluoroacetic acid . The solution was stirred overnight at room temperature and evaporated in vacuo. The residue was triturated with ether, filtered off by suction, and dried in vacuo, yielding 0.49 g of the title compound, melting point 155° C.

(I)
[3S(Z)]-2-[[[1-(2-Amino-4-thiazolyl)-2-[[1-[[[[3-[(1,4-dihydro-5-hydroxy-4-oxo-2-pyridinyl)methyl]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a suspension of 0.41 g (0.93 mmol) of (Z)-2-amino-α-[[2-(diphenylmethoxy)-1,1-dimethyl-2-oxoethoxy]imino]-4-thiazoleacetic acid in 20 ml of dry acetonitrile was added 0.39 ml (2.8 mmol) of triethylamine. The mixture was cooled to −30° C., and 0.19 ml (0.93 mmol) of diphenylchlorophosphate were added dropwise. The reaction mixture was stirred for one hour at −30° C. (solution a).

(S)-3-Amino-N-[[3-[(1,4-dihydro-5-hydroxy-4-oxo-2-pyridinyl)methyl]-2-oxo-1-imidazolidinyl]sulfonyl]-2-oxo-1-azetidinecarboxamide, trifluoroacetate salt (0.48 g, 0.93 mmol) was suspended in 20 ml of dry acetonitrile, and 0.78 ml (3.2 mmol) of bis-trimethylsilylacetamide added. The suspension was stirred for 30 minutes at room temperature and then added to solution (a).

The reaction mixture was stirred for one hour at −10° C. and then for 1.5 hours at 0° C. The resulting clear solution was evaporated in vacuo, and 50 ml of water was added to the oily residue. The mixture was adjusted to pH 2 by the addition of 2N hydrochloric acid, and [3S(Z)]-2-[[[1-(2-amino-4-thiazolyl)-2-[[1-[[[[-3-[(1,4-dihydro-5-hydroxy-4-oxo-2-pyridinyl)methyl]-2-oxo-1-imidazolidinyl]sulfonyl]amino]carbonyl]-2-oxo-3azetidinyl]amino]-2-oxoethylidene]amino]oxy]-2-methylpropanoic acid, disodium salt crystallized from the solution. The product was filtered off by suction, washed with water, and dried in vacuo, yielding 0.7 g of the title compound.

(J)
[3S(Z)]-2-[[[1-(2-Amino-4-thiazolyl)-2-[[1-[[[3-[(1,-4-dihydro-5-hydroxy-4-oxo-2-pyridinyl)methyl]-2-oxo--1-imidazolidinyl]sulfonyl]amino]carbonyl]--2-oxo-3-azetidinyl]amino]-2-oxo-ethylidene]amino]oxy]-2-meth ylpropanoic acid, disodium salt

[3S(Z)]-2-[[[1-(2-Amino-4-thiazolyl)-2-[[1-[[[3-[(1,-4-dihydro-5-hydroxy-4-oxo-2-pyridinyl)methyl]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (0.7 g, 0.85 mmol) was suspended in 1.4 ml of anisole and cooled to −10° C. Trifluoroacetic acid was added, and the solution was stirred for one hour at -10° C. Ether (100 ml) was added, and the precipitate was filtered off by suction, washed with ether and dried in vacuo.

The trifluoroacetic acid salt was dissolved in a mixture of methanol and water and the pH adjusted to 6.5 by the addition of 2N sodium hydroxide. Methanol was removed in vacuo and the aqueous solution freeze-dried, yielding 0.5 g of the title compound. This was purified by MPLC: melting point 250° C., dec.

EXAMPLE 9

[3S(Z)]-2-[[[1-(2-Amino-4-thiazolyl)-2-[[1-[[[[4-[(1,4-dihydro-5-hydroxy-4-oxo-2-pyridinyl)methyl]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt (A)
2-(Chloromethyl)-5-(phenylmethoxy)-1-(phenylmethyl)-4(1H)-pyridinone, hydrochloride A suspension of 3.21 g (10 mmol) of 2-(hydroxymethyl)-5-(phenylmethoxy)-1-(phenylmethyl)-4(1H)-pyridinone in 20 ml of chloroform was cooled to 0° C., and 4.65 ml (64 mmol) of thionylchloride was added dropwise. The mixture was stirred for ten minutes at 0° C. and then heated to reflux for one hour. The solvent was evaporated in vacuo and the residue washed with petroleum ether and dried in vacuo, yielding 3.66 g of the title compound, melting point 85° C., dec.

(B)
2-(Chloromethyl)-5-(phenylmethoxy)-1-(phenylmethyl)-4(1H)-pyridinone 2-(Chloromethyl)-5-(phenylmethoxy)-1-(phenylmethyl)-4(1H)-pyridinone, hydrochloride (3.5 g, 9.3 mmol) was dissolved in a mixture of water/ethyl acetate and the layers separated. The organic phase was washed twice with water, dried over magnesium sulfate and evaporated in vacuo. The residue was triturated with petroleum ether, filtered off by suction and dried in vacuo, yielding 2.27 g of the title compound, melting point 115°-120° C., dec.

(C) N-(Triphenylmethyl)piperazine-2,3-dione

A mixture of 2,3-piperazinedione (11.4 g, 100 mmol), bistrimethylsilylacetamide (55.7 g, 270 mmol) and 150 ml of acetonitrile was heated under reflux for one hour. Within 30 minutes, triphenylmethylchloride (22.2 g, 80 mmol) was added dropwise and the mixture was again refluxed for two hours. After stirring overnight at room temperature, 21.6 ml of water was added to the clear solution. The resulting precipitate (3.13 g) was filtered off and the filtrate concentrated in vacuo. The residue was triturated with water and dried to yield 25.5 g of crude title compound which was recrystallized from ethanol. Yield of pure product: 12.19 g, melting point 230°-235° C.

(D)
1-[[1,4-Dihydro-4-oxo-5-(phenylmethoxy)-1-(phenylmethyl)-2-pyridinyl]methyl]-4-(triphenylmethyl)-2,3-piperazinedione To a solution of N-(triphenylmethyl)piperazine-2,3-dione (4.19 g, 11.77 mmol) in 95 ml of dry dimethylformamide was added 0.35 g (11.77 mmol) of sodium hydride (80% oil). After the hydrogen evolution had ceased, a solution of 2-(chloromethyl)-5-(phenylmethoxy)-1-(phenylmethyl)-4(1H)-pyridinone (4.0 g, 11.77 mmol) in 25 ml of dry dimethylformamide was added to the thick suspension which then turned into a clear solution. After one hour of stirring at room temperature, precipitation started. After two hours, the crystals were filtered off, washed and dried in vacuo, yielding 5.13 g of the title compound, melting point 165°-168° C.

(E)
1-[[1,4-Dihydro-4-oxo-5-(phenylmethoxy)-1-(phenylmethyl)-2-pyridinyl]methyl]-2,3-piperazinedione To a solution of 1-[[1,4-dihydro-4-oxo-5-(phenylmethoxy)-1-(phenylmethyl)-2-pyridinyl]-methyl]-4-(triphenylmethyl)-2,3-piperazinedione (8.77 g, 13.23 mmol) in 65 ml of dichloromethane was added dropwise at room temperature 65 ml of formic acid. After stirring for three days, the volatiles were distilled off in vacuo and the residue triturated twice with ether to give 5.24 g of 1-[[1,4-dihydro-4-oxo-5-(phenylmethoxy)-1-(phenylmethyl)-2-pyridinyl]methyl]-2,3-piperazinedione, melting point 260°-265° C.

(F)
(S)-[1-[[[[4-[[1,4-Dihydro-4-oxo-5-(phenylmethoxy)-1-(phenylmethyl)-2-pyridinyl]methyl]-2,3-dioxo-1-piperazinyl]sulfonyl]amino]carbonyl]-2-oxo-3-azetidinyl]carbamic acid, phenylmethyl ester To a solution of (S)-3-[[(phenylmethoxy)carbonyl]amino]-2-azetidinone (0.44 g, 2.0 mmol) in 25 ml of dry ethyl acetate was added 0.28 g (2.0 mmol) of chlorosulfonyl isocyanate and the solution was stirred for 30 minutes at room temperature. To this were added 12 ml of dichloromethane, 0.61 g (6 mmol) of triethylamine and a prestirred (three hours) mixture of 1-[[1,4-dihydro-4-oxo-5-(phenylmethoxy)-1-(phenylmethyl)-2-pyridinyl]methyl]-2,3-piperazinedione (0.83 g, 2.0 mmol) and N-methyl-N-(trimethylsilyl)trifluoroacetamide (1.59 g, 8.0 mmol) in 25 ml of dry ethyl acetate. After stirring for three days at room temperature, ice water was added and the pH was adjusted to one with hydrochloric acid. The insoluble residue was filtered off and dried in vacuo yielding 1.15 g of the title compound of 72% purity.

(G)
(S)-3-Amino-N-[[4-[(1,4-dihydro-5-hydroxy-4-oxo-2-pyridinyl)methyl]-2,3-dioxo-1-piperazinyl]sulfonyl]-2-oxo-1-azetidinecarboxamide, 4-methylbenzenesulfonic acid salt To a solution of (S)-[1-[[[[4-[[1,4-dihydro-4-oxo-5-(phenylmethoxy)-1-(phenylmethyl)-2-pyridinyl]methyl]-2,3-dioxo-1-piperazinyl]sulfonyl]amino]carbonyl]-2-oxo-3-azetidinyl]carbamic acid, phenylmethyl ester (0.98 g, 1.32 mmol) in 20 ml of dimethylformamide was added 0.5 g (2.64 mmol) of p-toluenesulfonic acid and 0.5 g of palladium on charcoal (10%). For one hour, hydrogen was bubbled through the mixture. The catalyst was filtered off, the solvent distilled off in vacuo and the residue triturated with dichloromethane to yield, after drying, 0.82 g of the title compound, melting point 160°-185° C., dec.

(H)
[3S(Z)]-2-[[[1-(2-Amino-4-thiazolyl)-2-[[1-[[[[4-[(1,4-dihydro-5-hydroxy-4-oxo-2-pyridinyl)methyl]-2,3-dioxo-1-piperazinyl]sulfonyl]amino]carbonyl]-2-oxo-3-azetidinyl]amino]-2-oxoethylidene]amino]oxy]-2-methylpropanoic acid, diphenylmethyl ester To a solution of (Z)-2-amino-α-[[2-(diphenylmethoxy)-1,1-dimethyl-2-oxoethoxy]imino]-4-thiazoleacetic acid (0.57 g, 1.3 mmol) in 30 ml of dimethylformamide was added at −30° C. triethylamine (0.39 g, 3.9 mmol) and triphenylchlorophosphate (0.31 g, 1.3 mmol). After stirring for one hour, triethylamine (0.39 g, 3.9 mmol) and (S)-3-amino-N-[[4-[(1,4-dihydro-5-hydroxy-4-oxo- 2-pyridinyl)methyl]-2,3-dioxo-1-piperazinyl]sulfonyl]-2-oxo-1-azetidinecarboxamide, 4-methylbenzenesulfonic acid salt (0.98 g, 1.3 mmol) were added. The mixture was stirred for two hours at −10° C. and 1.5 hours at 0° C. Water and ethyl acetate were added, and the pH was brought to one with 3N hydrochloric acid. The precipitate was filtered off, washed with ethyl acetate and dried in vacuo, yielding 0.86 g of the title compound, melting point 130°–190° C., dec.

(I)

[3S(Z)]-2-[[[1-(2-Amino-4-thiazolyl)-2-[[1-[[[[4-[(1,4-dihydro-5-hydroxy-4-oxo-2-pyridinyl)methyl]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt To a suspension of [3S(Z)]-2-[[[1-(2-amino-4-thiazolyl)-2-[[1-[[[[4-[(1,4-dihydro-5-hydroxy-4-oxo-2-pyridinyl)methyl]-2, 3-dioxo-1-piperazinyl]-sulfonyl]amino]carbonyl]-2-oxo-3-azetidinyl]amino]-2-oxoethylidene]amino]oxy]-2-methylpropanoic acid, diphenylmethyl ester (0.8 g, 0.94 mmol) in 1.4 ml of anisole was added at −10° C. 7 ml of trifluoroacetic acid. After stirring for one hour, 30 ml of ether was added and the resulting precipitate filtered off and dried in vacuo. This trifluoroacetic acid salt was suspended in water and the pH adjusted to 6.5 with 2N sodium hydroxide. Freeze-drying of the solution gave 0.66 g of crude product which was chromatographed together with a second sample prepared in the same way (total: 1.55 g) on macroreticular sytrene-divinylbenzene copolymer under MPLC conditions, yielding 0.34 g of the title compound. A second column chromatography on macroreticular styrene-divinylbenzene copolymer furnished 0.18 g of the title compound, melting point 242°–270° C.

EXAMPLE 10

[3S(Z)]-2-[[[1-(2-Amino-4-thiazolyl)-2-[[1-[[[3-[[(1,4--dihydro-5-hydroxy-4-oxo-2-pyridinyl)methylene]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt (A) 4,5-Bis(phenylmethoxy)-2-pyridinecarboxylic acid, phenylmethyl ester 21.5 g (156 mmol) of potassium carbonate was added to a suspension of 29.4 g (120 mmol) of O-benzylcomenamic acid in 350 ml of dimethylformamide and stirred for one hour at room temperature. Benzylbromide (31 ml, 264 mmol) was added and the mixture was heated to 100° C. under stirring for 25 hours. After cooling to room temperature, the dimethylformamide was distilled off in vacuo and the residue triturated with ethyl acetate with short heating to 60° C. 40 g of inorganic salts were filtered off, the filtrate was concentrated to ca. 75 ml and chromatographed on silica gel with ethyl acetate:-petroleum ether 90:10 as eluent, yielding 35.5 g of the title compound, melting point 116.7° C.

(B) 4,5-Bis(phenylmethoxy)-2-pyridinemethanol

To a suspension of 95 mg (25 mmol) of lithium aluminum hydride in 10 ml of ether and 10 ml of tetrahydrofuran was added 1.06 g (25 mmol) of 4,5-bis(phenylmethoxy)-2-pyridinecarboxylic acid, phenylmethyl ester in three portions at 0° C. After stirring for 20 minutes at 0° C., 0.2 ml of saturated sodium bicarbonate solution, 0.2 ml of 10% potassium hydroxide solution and additional saturated sodium bicarbonate solution were added until the inorganic precipitate flocked together. The clear organic phase was decanted and evaporated in vacuo to yield an oil which slowly crystallized. Yield: 0.6 g, melting point 96.6° C.

(C) 4,5-Bis(phenylmethoxy)-2-pyridinecarboxaldehyde

To a solution of 0.54 g (1.7 mmol) of 4,5-bis(phenylmethoxy)-2-pyridinemethanol in 15 ml of acetone was added 1.5 mg (17 mmol) of manganese dioxide and the mixture was stirred overnight at room temperature. The mixture was then filtered over a silica gel column (70–250 mesh), and the aldehyde eluated with acetone. Evaporation of the eluent and trituration of the residue with petroleum ether furnished 0.3 g of the title compound, melting point 104.3° C.

(D)

1,4-Dihydro-5-hydroxy-4-oxo-2-pyridinecarboxaldehyde

To a solution of 4,5-bis(phenylmethoxy)-2-pyridinecarboxaldehyde (1.9 g, 6.0 mmol) in 25 ml of dry dimethylformamide was added 0.2 g of palladium on charcoal catalyst and hydrogen was bubbled through the mixture for three hours. The catalyst was removed by filtration, the solvent distilled off in vacuo and the residue triturated with ether to give 0.64 g of the title compound, melting point 174°–177° C., dec.

(E)

[3S(Z)]-2-[[[1-(2-Amino-4-thiazolyl)-2-[[1-[[[3-[[(1,-4-dihydro-5-hydroxy-4-oxo-2-pyridinyl)methylene]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt To a solution of [3S(Z)]-2-[[[2-[[1-[[[(3- amino-2-oxo-1-imidazolidinyl)sulfonyl]amino]carbonyl]-2-oxo-3-azetidinyl]amino]-1-(2-amino-4-thiazolyl)-2-oxoethylidene]amino]oxy]-2-propanoic acid, monosodium salt (0.64 g, 1.1 mmol) in 15 ml of dry dimethylformamide 1,4-dihydro-5-hydroxy-4-oxo-2-pyridinecarboxaldehyde (0.18 g, 1.3 mmol) was added, and, after stirring for 4.5 hours, an additional 0.02 g (0.14 mmol) of 4 was added. After stirring overnight at room temperature, the solvent was evaporated in vacuo, the residue taken up in 30 ml of water, filtered and the solution freeze-dried. The crude material (0.82 g) was dissolved in 5 ml of water and chromatographed on macroreticular styrene-divinylbenzene copolymer resin with water as eluent, yielding 0.22 g of pure product, melting point 248° C., dec.

EXAMPLE 11

[3S(Z)]-2-[[[1-(2-Amino-4-thiazolyl)-2-[[1-[[[[4-[(1,4--dihydro-5-hydroxy-4-oxo-2-pyridinyl)carbonyl]amino]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt (A) 4,5-Bis(phenylmethoxy)-2-pyridinecarboxylic acid To a solution of 11.8 g (28 mmol) of 4,5-bis(phenylmethoxy)-2-pyridinecarboxylic acid, phenylmethyl ester in 115 ml of tetrahydrofuran was added 16 ml of water and 35 ml of 1N potassium hydroxide. After stirring overnight at room temperature, 115 ml of water was added and the pH was adjusted to 2.5 with 1N hydrochloric acid. The acid was filtered off, washed with water and dried in vacuo, yielding 8.6 g of the title compound, melting point 203.6° C.

(B)
N-(2,3-Dioxo-1-piperazinyl)-4,5-bis(phenylmethoxy)-2-pyridinecarboxamide

To a suspension of 4,5-bis(phenylmethoxy)-2-pyridinecarboxylic acid (7.1 g, 21.17 mmol), hydroxybenzotriazole (0.29 g, 2.12 mmol) and N-aminopiperazine-2,3-dione (2.73 g, 21.17 mmol) in 140 ml of dry dimethylformamide was added, after 15 minutes of stirring, 4.80 g (23.3 mmol) of dicyclohexylcarbodiimide. After stirring for 21 hours at room temperature, dicyclohexylurea was filtered off (4.0 g ) and the solvent was evaporated in vacuo. The solid residue was triturated for 40 minutes with 240 ml of tetrahydrofuran, filtered, washed with tetrahyrofuran and dried in vacuo to yield 7.76 g of the title compound, melting point 231.1° C.

(C)
(S)-[1-[[[[4-[[[4,5-Bis(phenylmethoxy)-2-pyridinyl]carbonyl]amino]-2,3-dioxo-1-piperazinyl]sulfonyl]amino]-carbonyl]-2-oxo-3-azetidinyl]carbamic acid, phenylmethyl ester To a suspension of (S)-3-[[(phenylmethoxy)carbonyl]amino]-2-azetidinone (2.02 g, 9.18 mmol) in 130 ml of ethyl acetate, chlorosulfonyl isocyanate (1.43 g, 10 mmol) was added, and, after stirring for one hour, triethylamine (2.79 g, 27.54 mmol) was added at 0° C. To this mixture, a prestirred solution (1.5 hours) of N-(2,3-dioxo-1-piperazinyl)-4,5-bis(phenylmethoxy)-2-pyridinecarboxamide (4.10 g, 9.18 mmol) and N-methyl-N-(trimethylsilyl)trifluoroacetamide (5.4 g, 27.54 mmol) in 150 ml of ethyl acetate was added. After stirring overnight at room temperature, 220 ml of ice water was added and the pH was adjusted to 2 (from 10.3) with 3N hydrochloric acid. When the separated organic phase was treated with brine, the title compound precipitated and was filtered, washed with water and dried in vacuo, yielding 5.35 g. When 2.5 g of this material was triturated for one hour with a mixture of 25 ml of water and 37.5 ml of acetone at pH 6.3, 2.12 g of the title compound was obtained.

(D)
(S)-N-[4-[[[(3-Amino-2-oxo-1-azetidinyl)carbonyl]amino]sulfonyl]-2,3-dioxo-1-piperazinyl]-1,4-dihydro-5-hydroxy-4-oxo-2-pyridinecarboxamide To a solution of (S)-[1-[[[[4-[[[4,5-bis(phenylmethoxy)-2-pyridinyl]carbonyl]amino]-2,3-dioxo-1-piperazinyl]sulfonyl]amino]carbonyl]-2-oxo-3-azetidinyl]carbamic acid, phenylmethyl ester (1.54 g, 2 mmol) in 30 ml of dimethylformamide was added 0.77 g of palladium on charcoal, and the mixture was hydrogenolyzed for 45 minutes. The catalyst was removed by filtration over Hyflo and the resulting solution was used for the next step without isolation of the title compound.

(E)
[3S(Z)]-2-[[[1-(2-Amino-4-thiazolyl)-2-[[1-[[[[4-[[(1,-4-dihydro-5-hydroxy-4-oxo-2-pyridinyl)carbonyl]amino]-2,3-dioxo-1-piperazinyl]sulfonyl]amino]carbonyl]-2-oxo-3-azetidinyl]amino]-2-oxoethylidene]amino]oxy]-2-methylpropanoic acid, diphenylmethyl ester To a solution of (Z)-2-amino-α-[[2-(diphenylmethoxy)-1,1-dimethyl-2-oxoethoxy]imino]-4-thiazoleacetic acid (0.88 g, 2.0 mmol) in 20 ml of dimethylformamide was added triethylamine (0.60 g, 6.0 mmol) and, at −30° C. and under nitrogen, triphenylchlorophosphate (0.54 g, 2.0 mmol). After stirring for one hour at −30° C., triethylamine (0.20 g, 2 mmol) and the dimethylformamide solution of (S)-N-[4-[[[(3-amino-2-oxo-1-azetidinyl)carbonyl]amino]sulfonyl]-2,3-dioxo-1-piperazinyl]-1,4-dihydro-5-hydroxy-4-oxo-2-pyridinecarboxamide were added dropwise. The mixture was stirred for two hours at −10° C. and for 17 hours at 0° C. The solvent was distilled off in vacuo and the residue partitioned between 40 ml of ethyl acetate and 20 ml of ice water. When the pH was adjusted to 1.5 with dilute hydrochloric acid, an oil separated which was separated from the solvent and dried in vacuo, yielding 1.35 g of the title compound.

(F)
[3S(Z)]-2-[[[1-(2-Amino-4-thiazolyl)-2-[[1-[[[[4-[[(1,-4-dihydro-5-hydroxy-4-oxo-2-pyridinyl)carbonyl]amino]-2,3-dioxo-1-piperazinyl]sulfonyl]amino]carbonyl]-2-oxo-3-azetidinyl]amino]-2-oxoethylidene]amino]oxy]-2-methylpropanoic acid, disodium salt To a mixture of 2.6 ml of anisole and 13 ml of trifluoroacetic acid, [3S(Z)]-2-[[[1-(2-amino-4-thiazolyl)-2-[[1-[[[[4-[[(1,4-dihydro-5-hydroxy-4-oxo-2-pyridinyl)carbonyl]amino]-2,3-dioxo-1 -piperazinyl]sulfonyl]amino]carbonyl]-2-oxo-3-azetidinyl]amino]-2-oxoethylidene]amino]oxy]-2-methylpropanoic acid, diphenylmethyl ester (1.3 g, 1.48 mmol) was added at −10° C., and the mixture was stirred for two hours at 0° C. The volatiles were distilled off in vacuo and the residue triturated with ether to give 1.06 g of trifluoroacetic acid salt after drying. This trifluoroacetic acid salt was suspended in 20 ml of water and the pH was adjusted to 6.5 with 1N sodium hydroxide. The freeze dried solution furnished 1.10 g of crude product which was chromatographed on macroreticular styrene-divinylbenzene copolymer under MPLC conditions with water as eluent. Yield: 0.48 g. This material was again chromatographed twice together with other samples, prepared in the same manner. The second column chromatography was run on macroreticular styrene-divinylbenzene copolymer the third on Organogen, each with water as eluent. Final yield 0.10 g, melting point >300° C.

EXAMPLE 12

[3S(Z)]-3-[[(2-Amino-4-thiazolyl)[(2-fluoroethoxy)imino]acetyl]amino]-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, ethyldiisopropylamine salt To a solution of (Z)-2-amino-α-[(2-fluoroethoxy)imino]-4-thiazoleacetic acid (0.33 g, 1.4 mmol) in 5 ml of dry dimethylformamide was added N-hydroxybenzotriazole (0.19 g, 1.4 mmol) and N-ethyl-diisopropylamine (0.18 g, 1.4 mmol). At 0° C., dicyclohexylcarbodiimide (0.29 g, 1.4 mmol) was added and the mixture was stirred for one hour. A solution of (3S)-3-amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide, trifluoroacetate (1:2) salt (0.87 g, 1.6 mmol; see Example 1G) and N-ethyldiisopropylamine (0.41 g, 3.2 mmol) in 3 ml of dry dimethylformamide was added and after stirring for 2 hours at 0° C., the mixture was stirred for an additional 16 hours at room temperature. The dicyclohexylurea was filtered off, and the solvent distilled off in vacuo. The residual oil was triturated with water until completion of crystallization. The solid (0.82 g) was collected by filtration, the filtrate brought to pH 6.1 and freeze dried. The solid was suspended in 40 ml of water and the pH brought to 6.0 with 0.25N sodium hydroxide. Undissolved material was filtered off and the filtrate freeze dried. Two portions of freeze dried material were combined (ca. 0.6 g) and chromatographed on macroreticular styrene-divnylbenzene copolymer with water and water: acetonitrile 95:5 as eluent. After freeze drying, the appropriate fractions yielded 0.22 g of the title compound, melting point 163°–165° C.

EXAMPLE 13

[3S(Z)]-2-[[[1-(2-Amino-4-thiazolyl)-2-[[1-[[[[2-(carboxymethyl)-2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, trisodium salt (A) N,O-Dibenzyl-comenamyl chloride, hydrochloride Into a suspension of 16.77 g (50.0 mmol) N,O-dibenzyl-comenamic acid in 360 ml of dry dichloromethane was added 11.45 g (55.0 mmol) of phosphorous pentachloride in portions at 0°–5° C. Stirring was continued for 1 hour at room temperature, and the precipitate was collected by suction, washed with 20 ml of dry dichloromethane and dried in vacuo, yielding 15.02 g of the title compound, melting point 126°–127° C., dec.

(B) [2-[(Phenylmethoxy)carbonyl]hydrazino]acetic acid, 1,1-dimethylethyl ester

Into a stirred solution of 6.65 g (0.040 mol) of N-[(phenylmethoxy)carbonyl]hydrazine in 40 ml of dimethylformamide was dropped a solution of 8.58 g (0.044 mol) of t-butyl bromoacetate in 20 ml of dimethylformamide followed by a solution of 8.2 ml (0.048 mol) of N,N-diisopropylethylamine in 8 ml of dimethylformamide. After the mixture had been stirred at room temperature for one day, the solvent was distilled off in vacuo and the residue was taken up in ether and water. The organic layer was washed three times with water, dried (magnesium sulfate) and evaporated in vacuo to leave an oil (10.6 g), which was purified by column chromatography on silica gel eluting with ethyl acetate/toluene (1:1). The appropriate fractions were evaporated in vacuo and the residue was stirred with petroleum ether yielding 6.0 g of the title compound, melting point 61°–62° C.

(C)
[1-[[1,4-Dihydro-4-oxo-5-(phenylmethoxy)-2-pyridinyl]carbonyl]-2-[(phenylmethoxy)carbonyl]hydrazino]acetic acid, 1,1-dimethylethyl ester 15.6 ml (80.0 mmol) of N-Methyl-N-trimethylsilyltrifluoroacetamide was added to a solution of 11.2 g (40.0 mmol) of [2-[(phenylmethoxy)carbonyl]hydrazino]acetic acid, 1,1-dimethylethyl ester in 60 ml of dry acetonitrile. After stirring for 30 minutes at room temperature, the clear solution was evaporated in vacuo and the residue was dissolved in 45 ml of dry dichloromethane. This solution was dropped into a suspension of 15.61 g of N,O-dibenzyl-comenamyl chloride, hydrochloride in 60 ml of dry dichloromethane at room temperature. After stirring overnight, the reaction mixture was evaporated in vacuo to leave a residue which was stirred with 10 ml of methanol, evaporated in vacuo again and then chromatographed on silica gel eluting with ethyl acetate and ethyl acetate/methanol (10:1). After evaporation in vacuo, the appropriate fractions yielded a solid foam which became crystalline by stirring with ether. Yield: 12.7 g; melting point 177°–178° C., dec.

(D)
[1-[(1,4-Dihydro-5-hydroxy-4-oxo-2-pyridinyl)carbonyl]hydrazino]acetic acid, 1,1-dimethylethyl ester A suspension of 7.17 g (12.0 mmol) of [1-[[1,4-dihydro-4-oxo-5-(phenylmethoxy)-2-pyridinyl]carbonyl]-2-(phenylmethoxy)carbonyl]hydrazino]acetic acid, 1,1-dimethylethyl ester in 400 ml of methanol was hydrogenated in the presence of 1.6 g of palladium on charcoal (10%) for 40 minutes. The catalyst and the precipitated product were filtered off and washed well with 300 ml of dry dimethylformamide to dissolve the precipitated product. From the combined filtrates the solvents were removed in vacuo to leave a residue which crystallized by stirring with ether (1.68 g; melting point 221° C., dec.). Recrystallization from methanol yielded the pure compound. Yield: 1.26 g; melting point 225° C., sint. 229° C., dec.

(E)
(3S)-[1-[(1,4-Dihydro-5-hydroxy-4-oxo-2-pyridinyl)carbonyl]-2-[[[[2-oxo-3-[[(phenylmethoxy)carbonyl]amino]-1-azetidinyl]carbonyl]amino]sulfonyl]hydrazino]acetic acid, 1,1-dimethylethyl ester 9.0 ml (46.2 mmol) of N-methyl-N-trimethylsilyltrifluoroacetamide was added to a suspension of 3.2 g (11.0 mmol) of [1-[(1,4-dihydro-5-hydroxy-4-oxo-2-pyridinyl)carbonyl]hydrazino]acetic acid, 1,1-dimethylethyl ester in 120 ml of dry ethyl acetate. At room temperature, stirring was continued for 1 hour to give a clear solution (solution A).

To a suspension of 2.42 g (11.0 mmol) (S)-3-[[(phenylmethoxy)carbonyl]amino]-2-azetidinone in 80 ml of dry ethyl acetate 0.99 ml (11.0 mmol) chlorosulfonyl isocyanate was added with stirring. The mixture was stirred for 1 hour at room temperature and then cooled to 0° C. Solution A was dropped in at 0° C. and stirring was continued overnight at room temperature. After the addition of 4 ml of triethylamine, the mixture was evaporated in vacuo. The residue was dissolved in 10 ml of methanol-water (4:1). This solution was dropped into a mixture of 30 ml methanol/water, the pH of which was maintained at pH 2 to leave a residue (10.25 g) which became crystalline by stirring with few ml of water and methanol. The precipitate was purified by successive washing (stirring) with isopropanol/water (4:1), methanol, methanol/ether (1:1) and ether. Yield after drying in vacuo: 2.39 g.

(F)
(S)-3-Amino-1-[[[[2-(carboxymethyl)-2-[(1,4-dihydro-5-hydroxy-4-oxo-2-pyridinyl)carbonyl]hydrazino]sulfonyl]amino]carbonyl]-2-azetidinone, trifluoroacetate salt At 0° C., 2.39 g (3.9 mmol) of (3S)-[1-[(1,4-dihydro-5-hydroxy-4-oxo-2-pyridinyl)carbonyl]-2-[[[[2-oxo-3-[[(phenylmethoxy)carbonyl]amino]-1-azetidinyl]carbonyl]amino]sulfonyl]hydrazino]acetic acid, 1,1-dimethylethyl ester was added to a mixture of 7.0 ml of trifluoroacetic acid and 1.66 ml of thioanisole. After stirring overnight at room temperature, the solution was evaporated in vacuo. The residue was successively washed (stirred) with ethyl acetate, ethyl acetate/petroleum ether (1:1), petroleum ether and dichloromethane and then dried in vacuo. This crude salt was used in the next step without any further purification. Yield: 2.15 g.

(G)
[3S(Z)]-2-[[[1-(2-Amino-4-thiazolyl)-2-[[1-[[[[2-(carboxymethyl)-2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, diphenylmethyl ester 0.70 ml (3.24 mmol) of diphenylchlorophosphate was dropped into a −30° C. cold mixture of 1.42 g (3.24 mmol) of (Z)-2-amino-α-[[2-(diphenylmethoxy)-1,1-dimethyl-2-oxoethoxy]imino]-4-thiazoleacetic acid and 1.81 ml (12.96 mmol) of triethylamine in 30 ml of dry acetonitrile (solution A).

3.27 ml (12.96 mmol) of bistrimethylsilyl acetamide was added to a suspension of 2.13 g (∼3.3 mmol) crude (S)-3-amino-1-[[[[2-(carboxymethyl)-2-[(1,4-dihydro-5-hydroxy-4-oxo-2-pyridinyl)carbonyl]hydrazino]sulfonyl]amino]carbonyl]-2-azetidinone, trifluoroacetate salt in 30 ml of dry ethyl acetate at room temperature. After stirring for 1 hour, the clear solution was cooled and dropped into the −30° C. solution A. The mixture was stirred for 1 hour at −10° C., for an additional 1.5 hours at 0° C., and it was then evaporated in vacuo. The residue was stirred with few ml of water, the pH of which was adjusted to pH 2 by the addition of dilute hydrochloric acid. The precipitate was filtered off, washed with water, redissolved in water/acetone at pH 5.5–6.0 (addition of dilute sodium hydroxide) and purified by MPLC on macroreticular styrene-divinylbenzene copolymer eluting with water-methanol gradient (0–100%). Freeze drying of the appropriate fractions yielded 270 mg of the purified products. A suspension of this salt, in a few ml of cold water, was acidified with dilute hydrochloric acid at pH 2 to precipitate the free acid, which was collected by suction and dried in vacuo; yielding 0.19 g; melting point >180° C., dec.

(H)
[3S(Z)]-2-[[[1-(2-Amino-4-thiazolyl)-2-[[1-[[[2-(carboxymethyl)-2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, trifluoroacetic acid salt 0.17 g (0.2 mmol) of [3S(Z)]-2-[[[1-(2-amino-4-thiazolyl)-2-[[1-[[[[2-(carboxymethyl)-2-[(1,4-dihydro-5-hydroxy-4-oxo-2-pyridinyl)carbonyl ]hydrazino]sulfonyl]amino]carbonyl]-2- oxo-3-azetidinyl]amino]-2-oxo-ethylidene]amino]]oxy-2-methylpropanoic acid, diphenylmethyl ester was slowly added to a −10° C. cold, stirred solution of 0.62 ml (8.0 mmol) of trifluoroacetic acid and 0.087 ml (0.8 mmol) of thioanisole. Stirring was continued for 15 minutes at 0° C. The suspension was evaporated in vacuo at 0°–5° C., and the residue was stirred with dry ether, collected by suction, washed with dry ether and dried in vacuo, yielding 0.14 g; melting point >230° C., dec.

(I)
[3S(Z)]-2-[[[1-(2-Amino-4-thiazolyl)-2-[[1-[[[[2-(carboxymethyl)-2-[(1,4-dihydro-5-hydroxy-4-oxo-2-pyridinyl)carbonyl]hydrazino]sulfonyl]am ino]carbonyl]-2-oxo-3-azetidinyl]amino]-2-oxoethylidene]amino]oxy]-2-methylpropanoic acid, trisodium salt 115 mg (0.146 mmol) of [3S(Z)]-2-[[[1-(2-amino-4-thia zolyl)-2-[[1-[[[[2-(carboxymethyl)-2-[(1,4-dihydro-5-hydroxy-4-oxo-2-pyridinyl)carbonyl]hydrazino]sulfonyl]amino]carbonyl]-2-oxo-3-azetidinyl]amino]-2-oxoethylidene]amino]oxy]-2-methylpropanoic acid, trifluoroacetic acid salt was suspended in 1.5 ml of water and the pH was adjusted to 5.5 by dropwise addition of dilute sodium hydroxide. The solution was passed through two successive columns of macroreticular styrene-divinylbenzene copolymer (0.05–0.1 mm) and cross-linked dextran gel (25–100 μm) eluting with water. The appropriate fractions were combined and lyophilized yielding 100 mg of the title compound.

EXAMPLE 14
[3S(Z)]-2-[[[1-(2-Amino-4-thiazolyl)-2-[[1-[[[3-[[(-1,4-dihydro-5-hydroxy-4-oxo-2-pyridinyl)acetyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt

(A)
2-(Cyanomethyl)-5-(phenylmethoxy)-1-(phenylmethyl)-4(1H)-pyridinone

To a suspension of 2.0 g (6 mmol) of 2-(chloromethyl)-5-(phenylmethoxy)-1-(phenylmethyl)-4(1H)-pyridinone in 20 ml of acetonitrile was added 3.9 g (60 mmol) of potassium cyanide and 0.1 g of 18-crown-6; the mixture was heated to reflux for 2.5 hours. The salts were filtered off by suction, and the filtrate was evaporated in vacuo. The resulting residue was purified by column chromatography on silica gel using ethyl acetate/methanol (8:2) as eluent; yielding 0.55 g of the title compound, melting point 175°–180° C.

(B)
1,4-Dihydro-5-hydroxy-4-oxo-1-(phenylmethyl)-2-pyridineacetic acid

A mixture of 2.45 g (7.16 mmol) of 2-(cyanomethyl)-5-(phenylmethoxy)-1-(phenylmethyl)-4(1H)-pyridinone and 40 ml of concentrated hydrochloric acid (37%) was stirred for 4 hours at 70° C. and then evaporated in vacuo. The residue was suspended in 15 ml of ice cold water and the pH was adjusted to 2.0 by the addition of 5N sodium hydroxide. The precipitate was filtered off, washed with ice water and ether and dried in vacuo (1.71 g). The crude acid was dissolved in 20 ml of 0.5N sodium hydroxide, reprecipitated by acidification (pH 1.8) with 2N hydrochloric acid, collected by suction and washed with ice water. Yield: 1.52 g; melting point 231°–235° C.

(C)

1,4-Dihydro-5-hydroxy-4-oxo-N-(2-oxo-1-imidazolidinyl)-1-(phenylmethyl)-2-pyridineacetamide 4.99 ml (35.83 mmol) of triethylamine was added to a suspension of 9.29 g (35.83 mmol) of 1,4-dihydro-5-hydroxy-4-oxo-1-(phenylmethyl)-2-pyridineacetic acid, 0.28 g (1.79 mmol) of N-hydroxybenzotriazole, 0.22 g (1.79 mmol) of N-dimethylaminopyridine, 3.62 g (35.83 mmol) of N-aminoimidazolidinone and 8.13 g (39.41 mmol) of dicyclohexylcarbodiimide in 115 ml of dry dimethylformamide. Stirring was continued overnight at room temperature. The precipitated dicyclohexylurea was filtered off, washed with dimethylformamide, and the filtrate was evaporated in vacuo to leave a residue, which became crystalline by stirring with 110 ml of dichloromethane. The precipitate was collected by suction and dried in vacuo. To a suspension of this crude material in 65 ml of dry acetonitrile, 14.0 ml (71.6 mmol) of N-methyl-N-trimethylsilyltrifluoroacetamide was added. After having been stirred for 30 minutes at room temperature, the undissolved dicyclohexylurea was filtered off and the filtrate was evaporated in vacuo. The oily residue was boiled in 70 ml of methanol for 15 minutes and cooled. The precipitate was collected by suction, washed successively with methanol, methanol/ether (1:1) and ether and dried in vacuo. Yield: 8.7 g; sint. 242° C., melting point 260°–265° C. dec.

(D)

(S)-[1-[[[[3-[[[1,4-Dihydro-5-hydroxy-4-oxo-1-(phenylmethyl)-2-pyridinyl]acetyl]amino]-2-oxo-1-imidazolidinyl]sulfonyl]amino]carbonyl]-2-oxo-3-azetidinyl]carbamic acid, phenylmethyl ester, monosodium salt 5.86 ml (30.0 mmol) of N-methyl-N-trimethylsilyltrifluoroacetamide was added to a suspension of 3.42 g (10.0 mmol) of 1,4-dihydro-5-hydroxy-4-oxo-N-(2-oxo-1-imidazolidinyl)-1-(phenylmethyl)-2-pyridineacetamide in 50 ml of dry ethyl acetate and stirring was continued for 1 hour at room temperature (solution A).

To a solution of 2.20 g (10.0 mmol) of (S)-3-[[(phenylmethoxy)carbonyl]amino]-2-azetidinone in 50 ml of dry ethyl acetate, 0.90 ml (10.0 mmol) of chlorosulfonyl isocyanate was added with stirring, and the mixture was stirred for 1 hour at room temperature and then cooled to 0° C. Solution A was dropped in with stirring at 0° C. After stirring overnight at room temperature, the mixture was evaporated in vacuo and the residue was taken up in a few ml of methanol and water. The pH was adjusted to 5.5 by the addition of dilute sodium hydroxide and the filtered solution was freeze dried. MPLC on macroreticular styrene-divinylbenzene copolymer eluting with water/acetone (8:1) and freeze drying of the relevant pure fractions yielded 0.40 g of the title compound. The impure fractions were purified by a second MPLC using the same conditions. Yield: 0.60 g.

(E)

(S)-N-[3-[[[(3-Amino-2-oxo-1-azetidinyl)carbonyl]amino]sulfonyl]-2-oxo-1-imidazolidinyl]-1,4-dihydro-5-hydroxy-4-oxo-2-pyridineacetamide, trifluoroacetate salt A solution of 0.90 g (1.3 mmol) of (S)-[1-[[[[3-[[[1,4-dihydro-5-hydroxy-4-oxo-1-(phenylmethyl)-2-pyridinyl]acetyl]amino]-2-oxo-1-imidazolidinyl]sulfonyl]amino]carbonyl]-2-oxo-3-azetidinylcarbamic acid, phenylmethyl ester, monosodium salt in 13 ml of dry dimethylformamide containing 0.50 ml (6.5 mmol) of trifluoroacetic acid was hydrogenated in the presence of 0.15 g palladium on carbon (10%) for 20 minutes. The catalyst was filtered off and washed with a few ml of dimethylformamide. Evaporation of the filtrate in vacuo gave an oily residue which became crystalline by stirring with a few ml of ethyl acetate. Yield: 0.675 g; melting point >150° C., dec.

Simple stirring of this crude title compound in dry ethyl acetate for 1 hour, followed by filtration, washing with ethyl acetate and drying in vacuo improved the purity; yield: 80%, melting point >165° C., dec.

(F)

[3S(Z)]-2-[[[1-(2-Amino-4-thiazolyl)-2-[[1-[[[[3-[[(1,4-dihydro-5-hydroxy-4-oxo-2-pyridinyl)acetyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester 1.1 ml (4.45 mmol) of bistrimethylsilyl acetamide was added to a suspension of 0.75 g (1.35 mmol) of (S)-N-[3-[[[(3-amino-2-oxo-1-azetidinyl)carbonyl]amino]sulfonyl]-2-oxo-1-imidazolidinyl]-1,4-dihydro-5-hydroxy-4-oxo-2-pyridineacetamide, trifluoroacetate salt in 12 ml of dry ethyl acetate. After stirring for 1 hour at room temperature, the clear solution was evaporated in vacuo and the oily residue was dissolved in 12 ml of dry ethyl acetate (solution A).

Into a −30° C. cold suspension of 0.60 g (1.35 mmol) of (Z)-2-amino-α-[[2-(diphenylmethoxy)-1,1-dimethyl-2-oxoethoxy]imino]-4-thiazoleacetic acid in 12 ml of dry acetonitrile, 0.57 ml (5.4 mmol) of triethylamine was dropped, followed by 0.29 ml (1.35 mmol) diphenylchlorophosphate. Stirring was continued for 1 hour at −30° C. and an additional hour at 0° C. The solvent was removed in vacuo and the residue was precipitated by stirring with a few ml of water (0° C.). The precipitate was collected by suction, washed with cold water, suspended in water at pH 2 (addition of few drops of dilute hydrochloric acid), filtered off, washed successively with water, methanol and ether and dried in vacuo. Yield: 1.07 g; melting point >180° C., dec. This crude material was used in the next step without any further purification.

(G)

[3S(Z)]-2-[[[1-(2-Amino-4-thiazolyl)-2-[[1-[[[[3-[[(1,4-dihydro-5-hydroxy-4-oxo-2-pyridinyl)acetyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt 1.01 g (1.17 mmol) of crude [3S(Z)]-2-[[[1-(2-amino-4-thiazolyl)-2-[[1-[[[[3-[[(1,4-dihydro-5-hydroxy-4-oxo-2-pyridinyl)acetyl]amino]-2-oxo-1-imidazolidinyl]-sulfonyl]amino]carbonyl]-2-oxo-3-azetidinyl]amino]-2-oxoethylidene]amino]oxy]-2-methylpropanoic acid, diphenylmethyl ester was added to a −10° C. solution of 2.0 ml of anisole in 10 ml of trifluoroacetic acid. After being stirred for 20 minutes at −10° C., the solvent was removed in vacuo at +10° C. The residue was stirred with a few ml of dichloromethane, filtered off, stirred once more with a few ml of dichloromethane, collected by suction, washed with hexane and dried in vacuo. This crude product (1.06 g) was suspended in a few ml of water/acetonitrile and then dissolved by adjusting the pH to 6.0 by the addition of 1N sodium hydroxide. After concentrating in vacuo, the aqueous solution was chromatographed (MPLC) on macroreticular styrene-divinylbenzene copolymer eluting with water. The appropriate fractions were combined and freeze dried. Yield: 0.10 g, melting point >255° C.

EXAMPLE 15

[3S(Z)]-2-[[[1-(2-Amino-4-thiazolyl)-2-[[1-[[[[3-[[3-(1,4-dihydro-5-hydroxy-4-oxo-2-pyridinyl)-1-oxo-2-propenyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt

(A)

2-((1-Hydroxy-1-methoxy)methyl)-5-(phenylmethoxy)-4(1H)-pyridinone 9.0 g of 2-(hydroxymethyl)-5-(phenylmethoxy)-4(1H)-pyridinone and 26 g of manganese dioxide (activated) were stirred in 100 ml of methanol overnight at room temperature. Crystals of product were formed. After boiling the reaction mixture for ten minutes, followed by hot filtration through Hyflo, and washing the filtercake two times with 50 ml of boiling methanol, the combined filtrates were evaporated and the residue stirred with 50 ml of ethyl acetate. White crystals of product were formed. Yield: 9.7 g, melting point 156° C. dec.

(B)

3-[1,4-Dihydro-4-oxo-5-(phenylmethoxy)-2-pyridinyl]-2-propenoic acid, ethyl ester 0.5 g of p-toluenesulfonic acid, 6.26 g of 2-(1-hydroxy-1-methoxymethyl)-5-(phenylmethoxy)-4(1H)-pyridinone and 8.35 g of carbethoxymethylenetriphenylphosphorane were stirred for 3 hours in 100 ml of dioxane at 70° C. A clear, dark-colored solution was formed. Evaporation of the solvent in vacuo yielded an oily residue of the title compound and triphenylphosphine oxide. The residue was dissolved in 30 ml of isopropanol and crystals of product began to separate. After standing in a refrigerator overnight, the crystals were filtered off, washed with ether and recrystallized from isopropanol. Yield: 5.72 g, melting point 188° C.

(C)

3-[1,4-Dihydro-4-oxo-5-(phenylmethoxy)-2-pyridinyl]-2-propenoic acid 3-1,4-dihydro-4-oxo-5-(phenylmethoxy)-2-pyridinyl]-2-propenoic acid (1.5 g) and 0.29 g of potassium hydroxide were stirred in 30 ml of ethanol for 2 hours at 50° C. After evaporation of the solvent, the residue was dissolved in 100 ml of water and filtered. To the filtrate was added 2N hydrochloric acid until pH 5.0. Crystals of the title compound separated from the solution. They were filtered and washed with water and dried in vacuo. Yield: 1.14 g, melting point 236° C.

(D)

3-[1,4-Dihydro-4-oxo-5-(phenylmethoxy)-2-pyridinyl]-N-(2-oxo-1-imidazolidinyl)-2-propenamide 3-[1,4-Dihydro-4-oxo-5-(phenylmethoxy)-2pyridinyl-]-2-propenoic acid (10.85 g), 1 g of N-hydroxybenzotriazole, 0.01 g of N,N-dimethylaminopyridine and 8.24 g of dicyclohexylcarbodiimide were stirred for 30 minutes in 100 ml of dimethylformamide. After cooling to 0° C., 4 g of N-aminoimidazolidinone was added and stirring continued for 1 hour at 0° C. and 10 hours at room temperature. The resulting suspension was then heated to 60° C. and filtered. It was again suspended in 50 ml of dimethylformamide and heated to 60° C. and filtered again. The combined filtrates were evaporated at 40° C. (oil vacuo). The oily residue was stirred with 50 ml of water containing 2 g of sodium bicarbonate. After the filtration, the solid was washed with water, acetone and ether. 12.3 g of solid was obtained after drying. It was stirred together with 8 g of p-toluenesulfonic acid in 100 ml of dichloromethane for 1 hour. Filtration yielded 12.98 g of a white solid. This material was suspended in water. Recrystallization from water/dimethylformamide yielded 8.49 g of the title compound, melting point 271° C.

(E)

(3S)-[1-[[[[3-[[3-[1,4-Dihydro-4-oxo-5-(phenylmethoxy)-2-pyridinyl]-1-oxo-2-propenyl]amino]-2-oxo-1-imidazolidinyl]sulfonyl]amino]carbonyl]-2-oxo-3-azetidinyl]carbamic acid, phenylmethyl ester 3-[1,4-Dihydro-4-oxo-5-(phenylmethoxy)-2-pyridinyl]-N-(2-oxo-1-imidazolidinyl)-2-propenamide (3.55 g) was suspended in 100 ml of ethyl acetate and 6.3 g of N-methyl-N-(trimethylsilyl)trifluoroacetamide was added. After stirring for 1 hour, a clear solution was obtained. The solution was then added within 10 minutes to a cooled solution (0° C.) of 3.3 g of (S)-1-[[(chlorosulfonyl)amino]carbonyl]-3-[[(phenylmethoxy)carbonyl]amino]-2-azetidinone in 50 ml of ethyl acetate. After stirring overnight, the solvent was evaporated and the oily residue was stirred for 1 hour with 50 ml of isopropanol. The resultant precipitate was isolated by filtration and washed with isopropanol and ether. Yield: 5.91 g.

(F)

(3S)-3-Amino-N-[[3-[[(1,4-dihydro-5-hydroxy-4-oxo-2-pyridinyl]-1-oxo-2-propenyl]amino]-2-oxo-1-imidazolidinyl]sulfonyl]-1-azetidinecarboxamide, trifluoroacetate salt (3S)-[1-[[[[3-[[3-[1,4-Dihydro-4-oxo-5-(phenylmethoxy)-2-pyridinyl]-1-oxo-2-propenyl]amino]-2-oxo-1-imidazolidinyl]sulfonyl]amino]carbonyl]-2-oxo-3-azetidinyl]carbamic acid, phenylmethyl ester (6.8 g) was stirred at room temperature overnight in 60 ml of trifluoroacetic acid/thioanisole (3:1). After evaporation of the resulting solution to 1/3 of its volume, 50 ml of isopropanol and 10 ml of ether were added. (3S)-3-Amino-N-[[3-[[(1,4-dihydro-5-hydroxy-4-oxo-2-pyridinyl]-1-oxo-2-propenyl]amino]-2-oxo-1-imidazolidinyl]sulfonyl]1-azetidinecarboxamide, trifluoroacetate salt was obtained as a white precipitate. It was washed with ether several times and dried. Yield: 4.30 g.

(G)

[3S(Z)]-2-[[[1-(2-Amino-4-thiazolyl)-2-[[1-[[[[3-[[3-(1,4-dihydro-5-hydroxy-4-oxo-2-pyridinyl)1-oxo-2-propenyl]amino]-2-o xo-1-imidazolidinyl]-sulfonyl]amino]carbonyl]-2-oxo-3-azetidinyl]amino]2-oxoethylidene]amino]oxy]-2-methylpropanoic acid, disodium salt (Z)-2-amino-α-[[2-(diphenylmethoxy)-1,1-dimethyl-2-oxoethoxy]imino]-4-thiazoleacetic acid (2.2 g) and 1.5 g of triethylamine was dissolved in 150 ml of acetonitrile. At −30° C., 1.4 g of diphenylchlorophosphate was added dropwise and the mixture was stirred for 1 hour.

(3S)-3-Amino-N-[[3-[[(1,4-dihydro-5-hydroxy-4-oxo-2-pyridinyl]-1-oxo-2-propenyl]amino]-2-oxo-1imidazolidinyl]sulfonyl]-1-azetidinecarboxamide, 2.0 trifluoroacetate salt (3.3 g) suspended in 100 ml of ethyl acetate was treated with 6 ml of N-methyl-N-(trimethylsilyl)trifluoroacetamide and stirred for 1 hour at room temperature. The solution was added dropwise to the activated acid at −30° C. (15 minutes). It was then stirred for 1 hour at −10° C., and 30 minutes at 0° C. The solvent was evaporated in vacuo and the remaining oil was stirred with ice water at pH 2 (2N phosphoric acid). The ice water was discarded and the residue washed with ice water again and then dissolved in 100 ml of tetrahydrofuran. The solution was dried over sodium sulfate and the filtrate evaporated. The diphenylmethyl ester of the title compound was isolated as a solid foam, 1.81 g.

1.5 g of the material was stirred in 30 ml of trifluoroacetic acid/anisole at 0° C. for 30 minutes and after adding 100 ml of ether, 1.7 g of the trifluoroacetic acid salt of the title compound was isolated by filtration. This was dissolved in 10 ml of water, and sodium bicarbonate was added until the pH was 5.5. The filtered solution was chromatographed on macroreticular styrene-divinylbenzene copolymer (400 g) using water as the eluent. Appropriate fractions contained 0.64 g of product. Bioautography showed one minor bioactive side product. The material was subjected to a second column chromatography on Merck Lobar C using water as an eluent. Appropriate fractions contained 0.17 g of the title compound.

EXAMPLE 16

[3S(Z)]-2-[[[1-(2-Amino-4-thiazolyl)-2-[[1-[[[[2-[3-(1,4-dihydro-5-hydroxy-4-oxo-2-pyridinyl)-1-oxo-2-propenyl]hydrazino]sulfonyl]amino]carbonyl]-2-oxo-3-azetidinyl]amino]-2-oxoethylidene]amino]oxy]-2-methylpropanoic acid, disodium salt (A)
3-[1,4-Dihydro-4-oxo-5-(phenylmethoxy)-2-pyridinyl]-2-propenoic acid, 2-[(1,1-dimethyl-ethoxy)carbonyl]hydrazide 3-[1,4-Dihydro-4-oxo-5-(phenylmethoxy)-2pyridinyl]-2-propenoic acid (1.36 g), 0.75 g of N-hydroxybenzotriazole, 0.01 g of N,N-dimethylaminopyridine and 1.06 g of dicyclohexylcarbodiimide were stirred in 20 ml of dimethylformamide at 0° C. for 20 minutes. 0.66 g of N-(t-butoxycarbonyl)hydrazine was added. After stirring overnight, the formed dicyclohexylurea was filtered off and the filtrate was washed with 10 ml of dimethylformamide. The filtrate was evaporated to dryness and the residue was suspended in 30 ml of water, 1 g of sodium bicarbonate was added, and after stirring, the title compound was isolated by filtration. Recrystallization from dimethylformamide/water gave white crystals. Yield: 1.47 g, melting point 141° C.

(B)
3-[1,4-Dihydro-4-oxo-5-(phenylmethoxy)-2-pyridinyl]-2-propenoic acid, hydrazide 3-[1,4-Dihydro-4-oxo-5-(phenylmethoxy)-2-pyridinyl]-2-propenoic acid, 2-[(1,1-dimethylethoxy)-carbonyl]hydrazide (3.86 g) was stirred for one-half hour in 30 ml of trifluoroacetic acid at 0°–5° C. The trifluoroacetic acid salt of the title compound precipitated after adding 50 ml of diethylether. The salt was suspended in 30 ml of water, stirred with 2 g of sodium bicarbonate for 20 minutes, and the title compound was filtered off, washed with water and dried yielding a beige powder. Yield: 2.75 g.

(C)
(3S)-1,4-Dihydro-4-oxo-5-(phenylmethoxy)-2-pyridinecarboxylic acid, 2-[[[[2-oxo-3-[[(phenylmethoxy)carbonyl]amino]-1-azetidinyl]carbonyl]amino]sulfonyl]hydrazide 3-[1,4-Dihydro-4-oxo-5-(phenylmethoxy)-2-pyridinyl]-2-propenoic acid, hydrazide (2.86 g) and 8.1 g of N-methyl-N-(trimethylsilyl)trifluoroacetamide were stirred for 1 hour in 50 ml of ethyl acetate. To the resulting clear solution was added a solution of 3.27 g of (S)-1-[[(chlorosulfonyl)amino]carbonyl]-3-[[(phenylmethoxy)carbonyl]amino]-2-azetidinone in 30 ml of ethyl acetate (addition within 10 minutes) at 0° C. After stirring overnight, the solvent was evaporated and the residue was stirred with 50 ml of isopropanol and one drop of acid. The title compound was filtered off and washed with isopropanol and ether. Yield: 5.42 g.

(D)
(3S)-3-[1,4-Dihydro-5-hydroxy-4-oxo-2-pyridinyl]2-propenoic acid, 2-[[[(3-amino-2-oxo-1-azetidinyl)carbonyl]amino]sulfonyl]hydrazide, trifluoroacetate salt (3S)-1,4-Dihydro-4-oxo-5-(phenylmethoxy)-2-pyridinecarboxylic acid, 2-[[[[2-oxo-3-[[(phenylmethoxy)carbonyl]amino]-1-azetidinyl]carbonyl]amino]sulfonyl]hydrazide (5.2 g) was stirred in 50 ml of trifluoroacetic acid/thioanisole (3:1) at room temperature overnight. To the clear solution was added a mixture of 100 ml of ether/isopropanol (8:2). The resultant precipitate was filtered off and washed with ether. Yield: 4.01 g after drying.

(E)
[3S(Z)]-2-[[[1-(2-Amino-4-thiazolyl)-2-[[1-[[[[2-[3-(1,4-dihydro-5-hydroxy-4-oxo-2-pyridinyl)-1-oxo-2-propenyl]hydrazino]sulfonyl]amino]carbonyl]2-oxo-3-azetidinyl]amino]-2-oxoethylidene]amino]oxy]-2-methylpropanoic acid, disodium salt (Z)-2-Amino-α-[[2-(diphenylmethoxy)-1,1-dimethyl-2-oxoethoxy]imino]-4-thiazoleacetic acid (1.5 g) and 1 g of triethylamine were dissolved in 100 ml of acetonitrile. At −30° C., 1 g of diphenylchlorophosphate was added dropwise and the mixture was stirred for 1 hour.

(3S)-3-[1,4-Dihydro-5-hydroxy-4-oxo-2-pyridinyl]-2-propenoic acid, 2-[[[(3-amino-2-oxo-1-azetidinyl)carbonyl]amino]sulfonyl]hydrazide, trifluoroacetate salt (2.0 g) and 5.5 ml of N-methyl-N-(trimethylsilyl)trifluoroacetamide were stirred in 50 ml of ethyl acetate at room temperature for 1 hour. A clear solution was formed and after cooling was added dropwise to the activated acid at −30° C. The mixture was stirred for 1 hour at −30° C., 30 minutes at −10° C. and 1 hour at 0° C. The solvents were then evaporated in vacuo, and the residue stirred with 50 ml of isopropanol. A solid was formed. It was isolated by filtration and stirred with 100 ml of ice water for 20 minutes at pH 2 (phosphoric acid). Filtration yielded the diphenylmethyl ester of the title compound which was washed three times with 50 ml portions of ice water and dried (1.78 g). 1.5 g of the ester was stirred with 50 ml of trifluoroacetic acid-/anisole (4:1) for 30 minutes at 0° C. After adding 150 ml of ether, the trifluoroacetic acid salt of the free acid of the title compound was isolated by filtration (1.65 g).

1 g of that material was suspended in 5 ml of water and the pH was adjusted to 6.0 (sodium bicarbonate). The clear solution was then chromatographed on 400 g of macroreticular styrenedivinylbenzene copolymer using water as eluent, yielding 413 gm of the title compound. 400 mg of that material was rechromatographed on Merck Lobar C using water as eluent; yield: 160 mg.

EXAMPLE 17

[3S(Z)]-2-[[[1-(2-Amino-4-thiazolyl)-2-[[1-[[[[2[[(1,4-dihydro-5-hydroxy-4-oxo-2-pyridinyl)-carbonyl]amino]ethyl]amino]sulfonyl]amino]carbonyl]-2-oxo-3-azetidinyl]amino]-2-oxoethylidene]amino]oxy]-2-methylpropanoic acid, disodium salt

(A) N-(4-Methoxybenzyl)-O-benzylcomenamic acid

O-Benzylcomenic acid (10 g) and 10 ml of 4-methoxybenzylamine in 60 ml of water were refluxed for four hours. Acidification of the reaction mixture at room temperature with 2N hydrochloric acid to pH 2 yielded 15 g of crystals. Recrystallization from dioxane yielded 12.3 g of the title compound, melting point 175° C.

(B) 1,4-Dihydro-1-[(4-methoxyphenyl)methyl]-4-oxo5-(phenylmethoxy)-N-[2-[(phenylmethyl)amino]ethyl]2-pyridinecarboxamide N-(4-Methoxyphenyl)methyl]-O-benzyl-comenamic acid (3.69 g), 1.50 g of N-hydroxybenzotriazole and 2.05 g of dicyclohexylcarbodiimide were stirred for 1 hour at room temperature in 50 ml of dioxane. A solution of 1.35 g of N-benzylethylenediamine in 5 ml of dioxane was then added dropwise. After stirring overnight, the formed dicyclohexylurea was filtered off and the dioxane of the filtrate evaporated. The residue (oil) was dissolved in 50 ml of dichloromethane and extracted with two 50 ml portions of 10% sodium bicarbonate, and washed with water. After drying the dichloromethane solution over sodium sulfate and evaporation, the remaining solid was recrystallized from ethanol yielding crystals (4.2 g) of the title compound, melting point 112° C.

(C) N-(2-Aminoethyl)-1,4-dihydro-5-hydroxy-4-oxo-2-pyridinecarboxamide, p-toluenesulfonate salt 1,4-Dihydro-1-[(4-methoxyphenyl)methyl]-4-oxo-5-(phenylmethoxy)-N-[2-[(phenylmethyl)amino]ethyl]-2-pyridinecarboxamide (9.95 g) and 7.7 g of p-toluenesulfonic acid in 100 ml of methanol were treated with 3 g of palladium on charcoal (10%) and hydrogen was bubbled through the reaction mixture at 45°–50° C. over six hours. A stream of argon was then bubbled through the reaction mixture for 10 minutes. Filtration and evaporation of the filtrate yielded beige crystals of the title compound which were washed first with 20 ml of cold methanol and then 50 ml of ether. Yield: 10.5 g, melting point 271° C.

(D) N-(2-Aminoethyl)-1,4-dihydro-5-hydroxy-4-oxo-2-pyridinecarboxamide, dihydrochloride N-(2-Aminoethyl)-1,4-dihydro-5-hydroxy-4-oxo-2-pyridinecarboxamide, p-toluenesulfonate salt (5.42 g) was dissolved in 50 ml of formic acid and 7.5 ml of formic acid/hydrochloric acid gas (2.2 equivalents hydrochloric acid) was added followed by 150 ml of ether; white crystals of were obtained. Isolation by filtration and washing with 200 ml of ether yielded 2.60 g of the title compound, melting point 287° C.

(E) (3S)-]1-[[[[[2-[[(1,4-Dihydro-5-hydroxy-4-oxo-2-pyridinyl)carbonyl]amino]ethyl]amino]sulfonyl]amino]carbonyl]-2-oxo-3-azetidinyl]-carbamic acid, phenylmethyl ester To a 4.38 g of (S)-3-[[(phenylmethoxy)carbonyl]amino]-2-azetidinone suspended in 50 ml of ethyl acetate was added 2.83 g of chlorosulfonyl isocyanate at room temperature. A clear solution was obtained after 30 minutes of stirring.

N-(2-Aminoethyl)-1,4-dihydro-5-hydroxy-4-oxo-2-pyridinecarboxamide, dihydrochloride (5.40 g) in 50 ml of acetonitrile was stirred together with 24 g (6 equivalents) of N-methyl-N-(trimethylsilyl)trifluoroacetamide at 50° C. for 1 hour. The volatiles were then evaporated in vacuo. To the remaining oily residue was added 50 ml of ethyl acetate.

The above-prepared solutions were cooled to 0° C. and the second solution was added to the first while stirring. After stirring overnight, 200 ml of isopropanol was added under stirring at 0° C. to yield the title compound in the form of beige crystals. Yield: 8.77 g, melting point 145° C.

(F) (3S)-N-[[[[(3-Amino-2-oxo-1-azetidinyl)carbonyl]amino]sulfonyl]amino]ethyl]-1,4-dihydro-5-hydroxy-4-oxo-2-pyridinecarboxamide, 2.0 trifluoroacetate salt (3S)-[1-[[[[2-[[(1,4-Dihydro-5-hydroxy-4-oxo-2-pyridinyl)carbonyl]amino]ethyl]amino]sulfonyl]amino]carbonyl]-2-oxo-3-azetidinyl]carbamic acid, phenylmethyl ester (2 g) was stirred in 20 ml of thioanisole/40 ml of trifluoroacetic acid at 0° C. for 12 hours. After adding 100 ml of ether, white crystals (fine) of the title compound were isolated by filtration. Washing with 50 ml of isopropanol and 100 ml of ether yielded 2.12 g of the title compound, melting point 136° C., dec.

(G) [3S(Z)]-2-[[[1-(2-Amino-4-thiazolyl)-2-[[1-[[[[2-[[(1,4--dihydro-5-hydroxy-4-oxo-2-pyridinyl)carbonyl]amino]ethyl]amino]sulfonyl]amino]carbonyl]2-oxo-3-azetidinyl]amino]-2-oxoethylidene]amino]oxy]-2-methylpropanoic acid, diphenylmethyl ester (Z)-2-Amino-α-[[2-(diphenylmethoxy)-1,1-dimethyl-2-oxoethoxy]imino]-4-thiazoleacetic acid (4.40 g) and 3 g of triethylamine were dissolved in 150 ml of acetonitrile. At −30° C., 2.8 g of diphenylchlorophosphate was added dropwise and the mixture was stirred for 1 hour. (3S)-N-[[[[(3-Amino-2-oxo-1-azetidinyl)carbonyl]amino]sulfonyl]amino]ethyl]-1,4-dihydro-5-hydroxy-4-oxo-2-pyridinecarboxamide, 2.0 trifluoroacetate salt (6.13 g) and 17 g of N-methyl-N-(trimethylsilyl)trifluoroacetamide were stirred for 2 hours in 100 ml of ethyl acetate. The solvent of the clear solution was distilled off in vacuo and the remaining oil was evaporated for 2 hours at 30° C. (oil vacuo<0.01 mm). The residue was dissolved again in 100 ml of ethyl acetate and added dropwise to the activated acid at −30° C. (30 minutes). The mixture was stirred for 1 hour at −10° C. and 1 hour at 0° C. The solvent was evaporated and the remaining oily residue stirred with ice water at pH 3

(2N phosphoric acid). The ice water was discarded and the residue washed with ice water and dried. Yield: 7.8 g beige crystals.

(H)

3S(Z)]-2-[[[1-(2-Amino-4-thiazolyl)-2-[[1[[[[2-[[(1,4-dihydro-5-hydroxy-4-oxo-2-pyridinyl)-carbonyl]amino]ethyl]amino]sulfonyl]amino]carbonyl]2-oxo-3-azetidinyl]amino]-2-oxoethylidene]amino]oxy]-2-methylpropanoic acid, disodium salt

[3S(Z)]-2-[[[1-(2-Amino-4-thiazolyl)-2-[[-1[[[2-[[(1,4-dihydro-5-hydroxy-4-oxo-2-pyridinyl)- carbonyl]amino]ethyl]amino]sulfonyl]amino]carbonyl]2-oxo-3-azetidinyl]amino]-2-oxoethylidene]amino]oxy]-2-methylpropanoic acid, diphenylmethyl ester (3 g) was stirred for 30 minutes in 30 ml of trifluoroacetic acid/anisole. The trifluoroacetic acid salt of the free acid was isolated after precipitation with ether. 7.9 g of this material was suspended in 20 ml of water and the pH was adjusted to 6.0 with sodium bicarbonate. After stirring for one-half hour, the suspension was filtered and the solution chromatographed on macroreticular styrene-divinylbenzene copolymer with water as eluent yielding 0.24 g. This material was chromatographed again on a Merck Lobar C Column; yield: 0.078 g, melting point 275° C., dec.

EXAMPLE 18

2S2α,3β(Z)]]-2-[[[1-(2-Amino-4-thiazolyl)-2-[[1-[[[3-[[(1,4-dihydro-5-hydroxy-4-oxo-2-pyridinyl)carbonyl]amino]-2-oxo-1-imid azolidinyl]-sulfonyl]amino]carbonyl]-2-methyl-4-oxo-3azetidinyl]amino]-2-oxoethylidene]amino]oxy]-2methylpropanoic acid, disodium salt (A)

(2S-trans)-[1-[[[[3-[[[1,4-Dihydro-4-oxo-5-(phenylmethoxy)-2-pyridinyl]carbonyl]amino]-2-oxo-1-imidazolidinyl]sulfonyl]amino]carbonyl]-2-methyl4-oxo-3-azetidinyl]carbamic acid, phenylmethyl ester (3S-trans)-(4-methyl-2-oxo-3-azetidinyl)carbamic acid, phenylmethyl ester (2.35 g) and 1.41 g of chlorosulfonyl isocyanate were stirred for 1 hour at 0°–5° C. in 50 ml of ethyl acetate. A clear solution was obtained (solution A). 1,4-Dihydro-4-oxo-N-(2-oxo-1-imidazolidinyl)-5-(phenylmethoxy)-2-pyridinecarboxamide (3.28 g) and 6 g of N-methyl-N-(trimethylsilyl)trifluoroacetamide were stirred in 50 ml of ethyl acetate for 1 hour at 40° C. (solution B).

To the cooled (0° C.) solution A was added solution B during 30 minutes of stirring. After continuous stirring overnight, the solvent was evaporated and the residue (oily) stirred with 50 ml of isopropanol and 1 drop of acetic acid. The title compound was formed as a beige precipitate; melting point 163° C., dec.; 4.3 g.

(B)

(2S-trans)-N-[3-[[[(3-Amino-2-methyl-4-oxo-1-azetidinyl)carbonyl]amino]sulfonyl]-2-oxo-1-imidazolidinyl]-1,4-dihydro-5-hydroxy-4-oxo-2-pyridinecarboxamide, di-p-toluenesulfonate (2S-trans)-[1-[[[[3-[[[1,4-Dihydro-4-oxo-5-(phenylmethoxy)-2-pyridinyl]carbonyl]amino]-2-oxo-1-imidazolidinyl]sulfonyl]amino]carbonyl]-2-methyl-4-oxo-3-azetidinyl]carbamic acid, phenylmethyl ester (5.9 g) in 50 ml of dimethylformamide and 3.8 g of hydrated p-toluenesulfonic acid and 2.5 g of palladium on charcoal (10%) were hydrogenated at room temperature for 1 hour. After filtration over Hyflo, the dimethylformamide was distilled off in vacuo. The oily residue was stirred with 100 ml of dichloromethane. The title compound (5.8 g) was immediately formed as a white crystalline material.

(C)

[2S-[2α,3β(Z)]]-2-[[[1-(2-Amino-4-thiazolyl)-2-[[1-[[[3-[[(1,4-dihydro-5-hydroxy-4-oxo-2-pyridinyl)carbonyl]amino]-2-oxo-1-imidazolidinyl]sulfonyl]amino]carbonyl]-2-methyl-4-oxo-3-azetidinyl]amino]-2-oxoethylidene]amino]oxy]-2-methylpropanoic acid, disodium salt (Z)-2-Amino-α-[[2-(diphenylmethoxy)-1,1-dimethyl-2-oxoethoxy]imino]-4-thiazoleacetic acid (4.40 g) and 3.0 g of triethylamine were dissolved in 150 ml of acetonitrile. At −30° C., 2.8 g of diphenylchlorophosphate was added dropwise and stirred for 1 hour.

(2S-trans)-N-[3-[[[(3-Amino-2-methyl-4-oxo-1-azetidinyl)carbonyl]amino]sulfonyl]-2-oxo-1-imidazolidinyl]-1,4-dihydro-5-hydroxy-4-oxo-2-pyridinecarboxamide, di-p-toluenesulfonate (7.90 g) and 2.02 g of triethylamine were stirred for 5 minutes at −20° C. in 50 ml of dimethylformamide.

The above-prepared suspension and solution were combined at −30° C. and stirred for 1 hour at −30° C., 1 hour at −10° C. and overnight at 0°–10° C. The solvents were then distilled off in vacuo and the residue stirred with 100 ml of ice water at pH 3 (phosphoric acid). The diphenylmethyl ester of the title compound was filtered off and washed with water. Yield: 6.13 g, beige powder.

2 g of the ester was stirred in 30 ml of trifluoroacetic acid/anisole (4:1) for 30 minutes at 0° C. By adding 100 ml of ether, the trifluoroacetic acid salt of the free acid was precipitated. It was suspended in 10 ml of water and the pH was adjusted to 6.0. After filtration, the filtrate was passed through an macroreticular styrenedivinylbenzene copolymer column (water as eluent). Yield: 0.48 g.

A second column chromatography on Merck Lobar C with water as eluent gave 0.17 g of the title compound.

EXAMPLE 19

[3S(Z)]-2-Amino-N-[1-[[[[3-[[(1,4-dihydro-5-hydroxy-4-oxo-2-pyridinyl)carbonyl]amino]-2-oxo-1-imidazolidinyl]sulfonyl]amino]carbonyl]2-oxo-3-azetidinyl]-α-(methoxyimino)-4-thiazoleacetamide, monopotassium salt To a suspension of 0.6 g of (Z)-2-amino-α-(methoxyimino)-4-thiazoleacetic acid (0.003 mol) was added, at room temperature, 2.14 ml (0.009 mol) of tributylamine. The suspension was cooled to −30° C., at which temperature 0.66 ml of diphenylchlorophosphate (0.003 mol) was added. The reaction mixture was stirred at −30° C. for 1 hour (mixture A).

To a suspension of 1.62 g of (3S)-3-amino-N-[[3-[[(1,4-dihydro-5-hydroxy-4-oxo-2-pyridinyl)carbonyl]amino]-2-oxo-1-imidazolidinyl]sulfonyl]-2-oxo-1-azetidinecarboxamide (0.003 mol) in 20 ml of ethyl acetate was added, at room temperature, 2.6 ml of bis-trimethylsilylacetamide to form a clear, brownish solution, which was stirred for 1 hour at room temperature, then cooled to 0° C. (solution B).

Solution B was added dropwise with stirring to mixture A, while the temperature was maintained at −30° C. (ca. 10 minutes). The mixture was stirred at −10° C. for 1 hour and at 0° C. for an additional 1½ hours and evaporated in vacuo. The remaining syrup was dissolved in 50 ml of acetone. To the solution was added 6 ml of 1-molar potassium ethylhexanoate to precipitate 3.0 g of crude product. Addition of ether to the filtrate provided an additional 0.2 g of crude material. Chromatography of the crude material on macroreticular styrene-divinylbenzene copolymer yielded 1.85 g of the title compound.

EXAMPLE 20

[3S(Z)]-2-[[[1-(2-Amino-4-thiazolyl)-2-[[1-[[[[3-[[(1,-4-dihydro-5-hydroxy-4-oxo-2-pyridinyl)carbonyl-]amino]-2-oxo-1-imidazolidinyl]sulfonyl]amino]carbonyl]-2-oxo-3-azetidinyl]amino]-2-oxoethylidene]amino]oxy]-2-methylpropanoic acid

[3S(Z)]-2-[[[1-(2-Amino-4-thiazolyl)-2[[1-[[[[3-[[(1,4-dihydro-5-hydroxy-4-oxo-2-pyridinyl)carbonyl]amino]-2-oxo-1-imidazolidinyl]sulfon yl]amino]carbonyl]-2-oxo-3-azetidinyl]amino]2-oxoethylidene]amino]oxy]-2-methylpropanoic acid, disodium salt (2.2 g; see Example 1) was dissolved in 20 ml of acetone/water (1:1) and the pH was adjusted to pH 2 with 2N hydrochloric acid. Chromatography using macroreticular styrene-divinylbenzene copolymer yielded 0.7 g of the title compound.

EXAMPLE 21

[3S(Z)]-2-[[[1-(2-Amino-4-thiazolyl)-2-[[1-[[[[3-[[(1-,4-dihydro-5-hydroxy-4-oxo-2-pyridinyl)carbonyl]-amino]2-oxo-1-imidazolidinyl]sulfonyl]amino]carbonyl]2-oxo-3-azetidinyl]amino]-2-oxoethylidene]amino]oxy]-N-hydroxy-2-methylpropanamide, monosodium salt (Z)-2-Amino-α-[[1,1-dimethyl-2-oxo-2-[(triphenylmethoxy)amino]ethoxy]imino]-4-thiazoleacetic acid (4.72 g) was suspended in 65 ml of acetonitrile and, at −30° C., 3.72 ml of triethylamine was added. After 10 minutes of stirring, 1.97 ml of diphenylchlorophosphate was dropped in. Stirring was then continued for 90 minutes (solution A).

(3S)-3-amino-N-[[3-[[(1,4-dihydro-5-hydroxy-4-oxo-2-pyridinyl)carbonyl]amino]-2-oxo-1-imidazolidinyl]-sulfonyl]-2-oxo-1-azetidinecarboxamide (8.9 ml) was suspended in 70 ml of acetonitrile, and 7.7 ml of bis-trimethylsilylacetamide was added. A clear solution was obtained after stirring for 1 hour at −10° C. and 1½ hours at 0° C. The solvent and formed trifluoroacetic acid trimethylsilyl ester were evaporated in vacuo and the remaining oil was dissolved in 70 ml of ethyl acetate (solution B).

Solution A was then dropped into the stirred solution B at −20° C. during 30 minutes. Continuous stirring at −10° C. for 1½ hours and at 0° C. for 1 hour finished the reaction.

The solvents were then distilled off in vacuo and the oily residue was stirred with 300 ml of ice water whose pH was adjusted to 4.0 with phosphoric acid (10%). The formed solid was then filtered off, washed with water and dried in vacuo overnight. Yield: 9 g of crude.

The crude product (4.5 g) was stirred with 45 ml of formic acid (98%) and 4.5 ml of dichloromethane at 0° C. for one hour. The title compound (2.3 g) was obtained by precipitation with diethylether.

EXAMPLE 22

[3S(Z)]-2-[[[1-(2-Amino-4-thiazolyl)-2-[[1-[[[[2-[[3-[[(-1,4-dihydro-5-hydroxy-4-oxo-2-pyridinyl)carbonyl-]amino]-2-oxo-1-imidazolidinyl]carbonyl]hydrazino]-sulfonyl]amino]carbonyl]-2-oxo-3-azetidinyl]amino]-2-oxoethylidene]amino]oxy]-2methylpropanoic acid, disodium salt (A)

2-[[(Phenylmethoxy)carbonyl]amino]-2-imidazolidinone

1-Amino-2-imidazolidinone (26 g, 0.257 mol) was dissolved in 200 ml of water. The solution was layered with 200 ml of ethyl acetate and 43.8 g of chloroformic acid, benzyl ester (0.257 mol) was dropped into the mixture with stirring while maintaining the pH of 8.5–9 by the addition of saturated sodium bicarbonate solution. After stirring overnight at room temperature, the title compound was filtered off, washed first with water and then with ethyl acetate. Yield: 46.7 g, melting point 140°–144° C.

(B)

1-[[(Phenylmethoxy)carbonyl]amino]-3-(chlorocarbonyl)-2-imidazolidinone

To a suspension of 69.9 g (0.297 mol) of 2-[[(phenylmethoxy)carbonyl]amino]-2-imidazolidinone in 1 liter of dichloromethane was added a solution of 35 g of phosgene in 200 ml of dichloromethane. The mixture was stirred overnight at room temperature to form a clear solution. The solvent was removed in vacuo and the remaining syrup triturated with ether. Yield: 76.0 g, melting point 102°–105° C.

(C)

3-[[(Phenylmethoxy)carbonyl]amino]-2-oxo-limidazolidinecarboxylic acid, 2-[(1,1-dimethylethoxy)carbonyl]hydrazide 1-[[(Phenylmethoxy)carbonyl]amino]-3-(chlorocarbonyl)-2-imidazolidinone (76 g, 0.255 mol) was added at room temperature to 1.5 liters of ethyl acetate. After cooling to 0°–5° C., a solution of 39.6 g (0.9 mol) of N-(t-butoxycarbonyl)hydrazide and 41.8 ml of triethylamine (0.3 mol) in 150 ml of ethyl acetate were dropped in within 30 minutes. The mixture was stirred overnight. The precipitate was filtered off, dried, stirred with 800 ml of water to remove triethylamine hydrochloride, filtered, washed with water and dried. Yield: 71.2 g, melting point 195°–198° C.

(D)

2-[[3-[[[1,4-Dihydro-4-oxo-5-(phenylmethoxy)2-pyridinyl]carbonyl]amino]-2-oxo-1-imidazolidinyl]carbonyl]hydrazinecarboxylic acid, 1,1-dimethylethyl ester 3-[[(Phenylmethoxy)carbonyl]amino]-2-oxo-limidazolidinecarboxylic acid, 2-[(1,1-dimethylethoxy)-carbonyl]hydrazide (31.5 g, 0.08 mol) was dissolved in 400 ml of dimethylformamide, 16 g of palladium on charcoal (10%) was added and hydrogen was passed through the stirred reaction mixture. After 1 hour, the catalyst was filtered off. To the filtrate was added 19.62 g of 0-benzylcomenamic acid (0.08 mol), 0.48 g of dimethylaminopyridine and 0.64 g of N-hydroxybenzotriazole. The mixture was stirred for one hour at room temperature. A solution of 18.13 g of dicyclohexylcarbodiimide (0.088 mol) was added at room temperature and the mixture was stirred overnight. The precipitate (dicyclohexylurea) was filtered off, the filtrate evaporated in vacuo, and the residue triturated with water to which sodium bicarbonate was added to adjust the pH to 7.5. The precipitate was filtered off to yield 36 g of the title compound.

(E)
3-[[[1,4-Dihydro-4-oxo-5-(phenylmethoxy)-2pyridinyl]-carbonyl]amino]-2-oxo-1-imidazolidinecarboxylic acid, hydrazide 2-[[3-[[[1,4-Dihydro-4-oxo-5-(phenylmethoxy)2-pyridinyl]carbonyl]amino]-2-oxo-1-imidazolidinyl]carbonyl]hydrazinecarboxylic acid, 1,1-dimethylethyl ester (36g) was added, at −10° C. with stirring, to 300 ml of trifluoroacetic acid. The mixture was stirred at 0° C. for 1 hour, the trifluoroacetic acid was removed in vacuo and the residue triturated with ether to yield 41 g of the trifluoroacetate salt of the title compound. The trifluoroacetate salt was suspended with cooling in water and the pH was adjusted to 7 by the addition of 2N sodium hydroxide. The precipitate was filtered off to yield 21.9 g of the title compound.

(F)
3-[[(1,4-Dihydro-5-hydroxy-4-oxo-2-pyridinyl)carbonyl]amino]-2-oxo-1-imidazolidinecarboxylic acid, hydrazide 3-[[[1,4-Dihydro-4-oxo-5-(phenylmethoxy)-2pyridinyl]carbonyl]amino]-2-oxo-1-imidazolidinecarboxylic acid, hydrazide (21.9 g) was suspended in 250 ml of acetonitrile. To the suspension was added 75 ml of bis-trimethylsilylacetamide and the mixture was stirred to form a solution. To the solution was added 10 g of palladium on charcoal (10%) and hydrogen was passed through the vigorously stirred mixture. The debenzylation was complete after 1 hour. After filtration, 15 ml of methanol and 10 drops of acetic acid were added to precipitate the title compound. Yield: 10.8 g. This crude material was stirred with 150 ml of ethanol to yield 8.8 g of the title compound, melting point <205° C., dec.

(G)
(S)-[1-[[[[2-[3-[[(1,4-Dihydro-5-hydroxy-4-oxo-2-pyridinyl)carbonyl]amino]-2-oxo-1-imidazolidinyl]carbonyl]hydrazino]sulfonyl]amino]carbonyl]2-oxo-3-azetidinyl]carbamic acid, phenylmethyl ester To a suspension of 5.9 g (0.02 mol) of crude 3-[[(1,4-dihydro-5-hydroxy-4-oxo-2-pyridinyl)carbonyl]amino]-2-oxo-1-imidazolidinecarboxylic acid, hydrazide, 14.9 ml (0.08 mol) of N-methyl-N(trimethylsilyl)trifluoroacetamide was added and the mixture was stirred at 50° C. to form a solution (solution A).

To a suspension of 4.4 g of (S)-3-[[(phenylmethoxy)-carbonyl]amino]-2-azetidinone (0.02 mol) in 160 ml of ethyl acetate, 1.76 ml of chlorosulfonyl isocyanate was added at room temperature. The mixture was stirred for 1 hour (solution B).

Solution A was added (with cooling, ice) to solution B. After stirring for 1 hour, 2.8 ml (0.02 mol) of triethylamine was added to the mixture, which was then stirred overnight at room temperature. An additional 2.8 ml of triethylamine (0.02 mol) was added, followed by ice water. The mixture was stirred thoroughly for 1 hour and the layers were separated. The aqueous phase was acidified to pH 3 and the precipitate isolated by filtration. Yield: 5.3 g of crude title compound.

The crude material was dissolved in acetone/water and the pH of the solution was adjusted to 6.5 by the addition of 2N sodium hydroxide. After removal of the acetone in vacuo, the aqueous solution was filtered and lyophilized to yield 5.5 g of the crude sodium salt of the title compound. Chromatography of the crude sodium salt on macroreticular styrene-divinylbenzene copolymer yielded 0.64 g of purified material. This was dissolved in water and acidified with 2N hydrochloric acid to precipitate the title compound. Yield: 0.5 g.

(H)
(S)-N-[3-[[2-[[[(3-Amino-2-oxo-1-azetidinyl)carbonyl]amino]sulfonyl]hydrazino]carbonyl]-2-oxo-1-imidazolidinyl]-1,4-dihydro-5-hydroxy-4-oxo-2-pyridinecarboxamide 0.5 g of (S)-[1-[[[[2-[[3-[[(1,4-dihydro-5-hydroxy-4-oxo-2-pyridinyl)carbonyl]amino]-2-oxo-1imidazolidinyl]carbonyl]hydrazino]sulfonyl]amino]carbonyl]-2-oxo-3-azetidinyl]carbamic acid, phenylmethyl ester was added to a mixture of 0.5 ml of thioanisole and 2 ml of trifluoroacetic acid. The mixture was stirred overnight at room temperature and evaporated in vacuo. The residue was triturated with ethyl acetate to provide the title compound in quantitative yield.

(I)
[3S(Z)]-2-[[[1-[2-Amino-4-thiazolyl]-2-[[1-[[[[2-[[3-[[(1,4-dihydro-5-hydroxy-4-oxo-2pyridinyl)carbonyl]amino]-2-oxo-1-imi-dazolidinyl]carbonyl]hydrazino]sulfonyl]amino]carbonyl]-2-oxo--azetidinyl]amino]-2-oxoethylidene]amino]oxy]-2methylpropanoic acid, diphenylmethyl ester To a solution of 0.35 g (0.0008 mol) of (Z)-2-amino-α-[[2-(diphenylmethoxy)-1,1-dimethyl-2- -oxoethoxy]imino]-4-thiazoleacetic acid in 10 ml of acetonitrile, 0.34 ml of triethylamine was added. The mixture was cooled to −30° C. and 0.17 ml of diphenylchlorophosphate was added. The reaction mixture was stirred at −30° C. for 1 hour (solution A).

To a suspension of 0.008 mol (S)-N-[3-[[2[[[(3-amino-2-oxo-1-azetidinyl)carbonyl]amino]-sulfonyl]hydrazino]carbonyl]-2-oxo-1-imidazolidinyl]1,4-dihydro-5-hydroxy-4-oxo-2-pyridinecarboxamide in 6 ml of ethyl acetate, 0.7 ml of bis-trimethylsilylacetamide was added (solution B).

Solution B was added to solution A at −30° C. The mixture was stirred at −10° C. for 2 hours and at 0° C. for 1 hour and evaporated in vacuo. After treatment of the residue with water, 0.7 g of crude title compound was obtained, melting point 155° C., dec.

(J)
[3S(Z)]-2-[[[1-(2-Amino-4-thiazolyl)-2-[[1-[[[[2-[[3-[[(1,4-dihydro-5-hydroxy-4-oxo-2-pyridinyl)carbonyl]amino]-2-oxo-1-imidazolidinyl]carbonyl]hydrazino]-sulfonyl]amino]carbonyl]-2-oxo-3-azetidinyl]amino]--2-oxoethylidene]amino]oxy]-2-methylpropanoic acid, disodium salt To a suspension of 0.7 g 3S(Z)]-2-[[[1-[2-amino-4-thiazolyl]-2-[[1-[[[[2-[3-[[(1,4-dihydro-5-hydroxy-4-oxo--2-pyridinyl)carbonyl]amino]-2-oxo-1-imidazolidinyl]-carbonyl]hydrazino]sulfonyl]amino]carbonyl]-2-oxo-3-azetidinyl]amino]-2-oxoethylidene]amino]oxy]-2-methylpropanoic acid diphenylmethyl ester (0.00077 mol) in 1 ml of anisole, 6 ml of trifluoroacetic acid was added at −10° C. The mixture was kept at −10° C. for 1 hour. At −10° C., ether was added to precipitate the trifluoroacetate of the free acid of the starting material, yield 0.5 g.

The precipitate was suspended in water with cooling and the pH was adjusted to 5.5 by the addition of 2N sodium hydroxide. Freeze drying yielded 0.55 g of crude material. The crude material was purified by chromatography on macroreticular styrene-divinylbenzene copolymer to yield 0.1 g of purified title compound.

EXAMPLE 23

[3S(Z)]-2-[[[1-(2-Amino-4-thiazolyl)-2-[[1-[[[2-[(1,-4-dihydro-5-hydroxy-4-oxo-2-pyridinyl)carbonyl-2-methylhydrazino]sulfonyl]amino]carbonyl]-2-oxo-3-azetidinyl]amino]-2-oxoethylidene]amino]oxy-2methylpropanoic acid, disodium salt

(A)

1,4-Dihydro-4-oxo-5-(phenylmethoxy)-1-(phenylmethyl)-2-pyridinecarboxylic acid, 1-methylhydrazide N,O-Dibenzylcomenamyl chloride (0.15 mol) was suspended in 150 ml of dichloromethane with ice cooling. To the suspension, 26.2 ml (0.5 mol) of methylhydrazine was added, followed by 150 ml of acetonitrile. The mixture was stirred overnight at room temperature. The turbid solution was evaporated in vacuo and triturated with 300 ml of water. The solid material obtained was filtered and dried to yield 26.3 g of crude material. Recrystallization of the crude material from water yielded 12.7 g of pure title compound, melting point 138°–142° C.

(B)

(S)-1,4-Dihydro-4-oxo-5-(phenylmethoxy)-1-(phenylmethyl)-2-pyridinecarboxylic acid, 1-methyl-2-[[[[2-oxo-3-[[(phenylmethoxy)carbonyl]amino]-1-azetidinyl]carbonyl]amino]sulfonyl]hydrazide 1,4-Dihydro-4-oxo-5-(phenylmethoxy)-1-(phenylmethyl)-2-pyridinecarboxylic acid, 1-methylhydrazide (1.82 g, 0.005 mol) was suspended in 20 ml of ethyl acetate. At room temperature, a total of 1.85 ml of N-methyl-N-(trimethylsilyl)trifluoroacetamide (0.01 mol) was added. The mixture was stirred for 4 hours at 60° C. (suspension A).

(S)-3-[[(Phenylmethoxy)carbonyl]amino]-2-azetidinone (1.1 g, 0.005 mol) was suspended in 40 ml of ethyl acetate at room temperature and 0.5 ml of chlorosulfonyl isocyanate was added. The mixture was stirred at room temperature for 1 hour to form a solution (solution B).

To solution B, 1.2 ml of triethylamine was added (with ice cooling) followed by 20 ml of dichloromethane and suspension A. The suspension was stirred overnight at room temperature. To the slightly turbid solution, 30 ml of dichloromethane and 20 ml of water was added and the mixture was stirred for 1 hour at room temperature.

The pH of the aqueous phase was 6.5–7. 60 ml of ethyl acetate was added, the organic layer separated and the aqueous phase washed twice with a mixture of dichloromethane/ethyl acetate (1:3). The combined organic phases were dried (magnesium sulfate) and evaporated to yield 4.5 g of a syrup which crystallized on standing over the weekend. After treatment with ether, 2.6 g of crude title compound was obtained.

(C)

1,4-Dihydro-5-hydroxy-4-oxo-2-pyridinecarboxylic acid, 2-[[[(3-amino-2-oxo-1-azetidinyl)carbonyl]amino]sulfonyl]-1-methylhydrazide, trifluoroacetate salt To a solution of 2 g of (S)-1,4-dihydro-4-oxo-5-(phenylmethoxy)-1-(phenylmethyl)-2-pyridinecarboxylic acid, 1-methyl-2-[[[[2-oxo-3-[[(phenylmethoxy)carbonyl]amino]-1-azetidinyl]carbonyl]amino]sulfonyl]hydrazide in 60 ml of dimethylformamide, 1.1 ml of trifluoroacetic acid was added, followed by one gram of palladium on charcoal (10%). After flushing with nitrogen, hydrogen was passed through the solution for 60 minutes with stirring, the catalyst was removed by filtration, the filtrate evaporated in vacuo and the residue triturated with ether to yield 1.1 g of crude title compound. Yield: 86.6%.

(D)

[3S(Z)]-2-[[[1-(2-Amino-4-thiazolyl)-2-[[1-[[[2-(-1,4-dihydro-5-hydroxy-4-oxo-2-pyridinyl)carbonyl]-2-methylhydrazino]sulfonyl]amino]carbonyl]2-oxo-3-azetidinyl]amino]-2-oxoethylidene]amino]oxy]-2-methylpropanoic acid, diphenylmethyl ester To a suspension of 0.88 g of (Z)-2-amino-α-[[2-(diphenylmethoxy)-1,1-dimethyl-2-oxoethoxy]imino]-4-thiazoleacetic acid (0.002 mol) in 30 ml of acetonitrile 0.7 ml (0.005 mol) of triethylamine was added, followed, at −30° C., by 0.44 ml of diphenylchlorophosphate (0.002 mol). The mixture was stirred at −30° C. for 1 hour (solution A).

To a suspension of 1.2 g (0.002 mol) of 1,4-dihydro-5-hydroxy-4-oxo-2-pyridinecarboxylic acid, 2-[[[(3-amino-2-oxo-1-azetidinyl)carbonyl] amino]sulfonyl]-1-methylhydrazide, trifluoroacetate salt in 30 ml of ethyl acetate, 2 ml of bis-trimethylsilylacetamide (ca. 0.008 mol) was added at room temperature to form, after 30 minutes, a clear solution (solution B).

At −30° C., solution B was added dropwise to solution A.(ca. 10 minutes). The temperature was kept at −10° C. for 1 hour and at 0° C. for another hour. The solvent was evaporated and the residue treated with water, to yield, after filtration and drying, 2.4 g of crude title compound.

(E)

[3S(Z)]-2-[[[1-(2-Amino-4-thiazolyl)-2-[[1-[[[2-[(1,-4-dihydro-5-hydroxy-4-oxo-2-pyridinyl)carbonyl-2-methylhydrazino]sulfonyl]amino]carbonyl]2-oxo-3-azetidinyl]amino]-2-oxoethylidene]amino]oxy]-2-methylpropanoic acid, disodium salt At −10° C., 2.4 g of crude [3S(Z)]-2-[[[1-(2-amino-4-thiazolyl)-2-[[1-[[[2-[(1,4-dihydro-5-hydroxy-4-oxo-2-pyridinyl)carbonyl]-2-methylhydrazino]sulfonyl]amino]carbonyl]-2-oxo-3azetidinyl]amino]-2-oxoethylidene]amino]oxy]2-methylpropanoic acid, diphenylmethyl ester was added to a mixture of 20 ml of trifluoroacetic acid and 4 ml of anisole. The mixture was stirred at −10° C. for 1 hour and the reaction product was precipitated by the addition of ether at −10° C.; Yield: 1.12 g of the crude trifluoroacetate of the title compound.

The crude material was converted to the sodium salt by the addition of 2N sodium hydroxide to a suspension in acetone-water and lyophilization. The sodium salt was purified by chromatography on macroreticular styrene-divinylbenzene copolymer (elution with water). Yield: 0.25 g.

EXAMPLE 24

(3S)-2-[[[1-(2-Amino-4-thiazolyl)-2-[[1-[[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid

(A)
2-(Hydroxymethyl)-5-(phenylmethoxy)-4H-pyran-4-one

A suspension of 5-hydroxy-2-(hydroxymethyl)-4H-pyran-4-one (56.8 g, 0.4 mole) in 400 ml of methanol was treated with sodium hydroxide, (16 g, 0.4 mole) in 200 ml of warm methanol followed by 50.6 g (46 ml, 0.4 mole) of benzyl chloride. The mixture was heated to reflux for 3.5 hours, cooled, and poured in 1 L of water. The resulting solid was filtered and washed with ca. 1.5 L of water, 200 ml of ethanol and 400 ml of hexane. After drying under high vacuum, the weight of product was 55.7 g.

(B)
1,4-Dihydro-2-(hydroxymethyl)-5-(phenylmethoxy)4-pyridinone

A mixture of 2-hydroxymethyl-5-(phenylmethoxy)4H-pyran-4-one (9.65 g, 41.59 mmole), 95 ml of concentrated ammonia and 20 ml of ethanol and heated at reflux overnight. An additional 75 ml of ammonium hydroxide was added, the mixture was refluxed for 2 hours and cooled. The resulting brown solid was filtered and washed with water until the washings were neutral. The crude product was suspended in ethanol, filtered, washed with ethanol and hexane and dried in vacuo. The yield of the title compound was 7.61 g.

(C)
1-(Chloromethyl)-1,4-dihydro-5-(phenylmethoxy)4-pyridinone, hydrochloride A suspension of 1,4-dihydro-2-(hydroxymethyl)5-(phenylmethoxy)-4-pyridinone (3 g, 12.99 mmole) in chloroform (15 ml) was cooled to 0° C. under argon and treated with thionyl chloride (6.1 ml, 83.62 mmole). Within several minutes, a homogeneous solution was obtained. After stirring an additional 5 minutes, a cream colored solid precipitated. The cooling bath was removed and the mixture was heated at reflux for 45 minutes. The mixture was cooled to 0° C. and the white suspended material was filtered, washed with chloroform and hexane and dried in vacuo. The yield of the title compound was 3.65 g.

(D)
2-(Azidomethyl)-1,4-dihydro-5-(phenoxymethyl)4-pyridinone

A mixture of 1-(chloromethyl)-1,4-dihydro-5-(phenylmethoxy)-4-pyridinone, hydrochloride (3.59 g, 12.54 mmole), sodium azide (4.08 g, 62.7 mmole) and diisopropylethylamine (2.19 ml, 12.54 mmole) in 70 ml of dimethylformamide was stirred at room temperature under argon for 3.5 days. An additional 4.08 g of sodium azide was added and the mixture was heated at 45°-50° C. for 2 hours. After cooling, the reaction was poured into 500 ml of water, producing an insoluble white solid. The pH of the supernatant liquid was lowered from 8.5 to 7.5 with dilute hydrochloric acid, and the white solid was filtered. After washing with water, acetone, and hexane, the solid was dried in vacuo. The yield of the title compound was 2.81 g.

(E)
2-(Aminomethyl)-4-oxo-5-(phenylmethoxy)pyridine

A suspension of 2-(azidomethyl)-1,4-dihydro-5-(phenoxymethyl)-4-pyridinone (2.030 g, 7.93 mmole) and platinum oxide (200 mg) in 100 ml of dimethylformamide was stirred for six hours at room temperature under one atmosphere of hydrogen. The catalyst was removed by filtration and the solution was concentrated in vacuo to afford 1.5 g of the title compound as a grey powder.

(F)
(3S)-1-[[[[[(1,4-Dihydro-5-hydroxy-4-oxo-2pyridinyl)methyl]amino]sulfonyl]amino]carbonyl]2-oxo-3-[[(phenylmethoxy)carbonyl]amino]azetidine To a stirred suspension of 2-(aminomethyl)-4-oxo-5-(phenylmethoxy)pyridine (2.330 g, 10.13 mmole) in 60 ml of ethyl acetate was added N-methyl-N(trimethylsilyl)trifluoroacetamide (3.76 ml, 20.26 mmole). The resulting solution was stirred for 30 minutes at room temperature and then cooled to 0° C. Concurrently, to a stirred suspension of (S)-3-[[(phenylmethoxy)carbonyl]amino]-2-azetidinone (2.228 g, 10.13 mmole) in 60 ml of ethyl acetate was added chlorosulfonyl isocyanate (882 μl, 10.13 mmol). The resulting solution was stirred for 30 minutes at room temperature then cooled to 0° C. and treated with triethylamine (4.23 ml, 30.39 mmole) followed by the solution of silylated 2-(aminomethyl)-4-oxo-5-(phenylmethoxy)pyridine described above. The mixture was stirred for two days at room temperature.

The mixture was concentrated in vacuo, the residue dissolved in acetonitrile-water (40–60) and the pH lowered to 2.9 whereupon a thick oil separated. Upon cooling to 5° C., the oil solidified. The solid was separated, washed four times with water, and dried in vacuo to afford 3.4 g of crude title compound. The crude was dissolved in a minimum volume of dimethylformamide and loaded on a column (1L) of macroreticular styrene-divinylbenzene copolymer. The column was eluted with a stepwise acetone-water gradient. Desired material eluted with ca. 65% acetone. The relevant fractions were combined and lyophilized to afford 2.69 g of the title compound.

(G)
(3S)-2-[[[1-(2-Amino-4-thiazolyl)-2-[[1[[[[[(1,4-dihydro-5-hydroxy-4-oxo-2-pyridinyl)methyl]amino]sulfonyl]amino]carbonyl]-2-oxo-3azetidinyl]amino]-2-oxoethylidene]amino]oxy]-2methylpropanoic acid, diphenylmethyl ester (3S)-1-[[[[[(1,4-Dihydro-5-hydroxy-4-oxo-2pyridinyl)methyl]amino]sulfonyl]amino]carbonyl]2-oxo-3-[[(phenylmethoxy)carbonyl]amino]azetidine (912 mg, 1.64 mmole), p-toluenesulfonic acid monohydrate (625 mg, 3.28 mmole) and 10% palladium on charcoal (190 mg) in 16 ml of dimethylformamide were stirred under one atmosphere of hydrogen until 3.28 mmole (73 ml) of hydrogen was consumed (ca. 3 hours).

To a stirred solution of (Z)-2-amino-α-[[2- (diphenylmethoxy)-1,1-dimethyl-2-oxoethoxy]imino]4-thiazoleacetic acid (846 mg, 1.804 mmole) in 16 ml of dimethylformamide at −20° C. was added diphenylchlorophosphate (374 1, 1.804 mmole) followed by triethylamine (450 μl, 3.28 mmole). The solution was stirred for 1 hour at −20° C. whereupon the above-described mixture of hydrogenolyzed compound was added. Triethylamine (921 μl 6.6 mmole) was then added. The resulting mixture was stirred at −20° C. for one hour and then at 5° C. overnight. The catalyst was removed by filtration, volatiles Were removed in vacuo and the resulting oil was dissolved in a minimum volume of acetone-water (75-25) (pH 5.2) and added dropwise to a stirred suspension of 20 ml of Dowex 50×2-400 (K+) in acetone-water (35-65). After 40 minutes, the mixture was filtered and the filtrate lyophilized to afford 2.1 g of solid. The solid was dissolved in a minimum amount of acetonitrile-water (40-60) (pH 5.6) and loaded onto a column (800 ml) of macroreticular styrene-divinylbenzene copolymer, eluting with a stepwise acetonitrile-water gradient. Desired material eluted with ca. 30% acetonitrile. The relevant fractions were combined and lyophilized to afford the title compound.

(H)
(3S)-2-[[[1-(2-Amino-4-thiazolyl)-2-[[1[[[[(1,4-dihydro-5-hydroxy-4-oxo-2-pyridinyl)methyl]amino]sulfonyl]amino]carbonyl]-2-oxo-3azetidinyl]amino]-2-oxo-ethylidene]amino]oxy]-2methylpropanoic acid Trifluoroacetic acid (4.7 ml) was added dropwise to a stirred suspension of (3S)-2-[[1(2-amino-4-thiazolyl)-2-[-[1-[[[[(1,4-dihydro-5-hydroxy-4-oxo-2-pyridinyl)methyl]amino]sulfonyl]amino]carbonyl]-2-oxo-3-azetidinyl]amino]-2-oxoethylidene]amino]oxy]-2-methylpropanoic acid, diphenylmethyl ester (131 mg, 0.113 mmole) in 3 ml of dichloromethane and 0.3 ml anisole at 0° C. After stirring 45 minutes at 5° C., 2 ml of toluene was added and the volatiles were removed in vacuo. The resulting oil was washed with hexane (3×4 ml) and triturated to a solid with 10 ml of ether. The solid was washed once with ether (10 ml) and dried in vacuo. The above reaction and work-up were repeated on 0.166 mmole of (3S)-2-[[[1-(2-amino-4-thiazolyl)-2-[[1-[[[[(1,4-dihydro-5-hydroxy-4-oxo-2-pyridinyl)methyl]amino]sulfonyl]amino]carbonyl-2-oxo-3-azetidinyl]amino]-2-oxoethylidene]amino]oxy]-2-methylpropanoic acid, diphenylmethyl ester. The crude solids were combined, dissolved in 2 ml of acetonitrile-water (40-60) (pH 2.5) and chromatographed on a column (200 ml) of macroreticular styrene-divinylbenzene copolymer, using an acetonitrile-water gradient. The desired material eluted at acetonitrile-water (20-80). The relevant fractions were combined and lyophilized to afford 103 mg of the title compound as a white solid, melting point 180° C., dec.

What is claimed is:
1. A compound having the formula

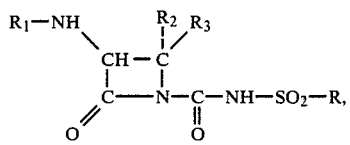

or a pharmaceutically acceptable salt thereof wherein R is

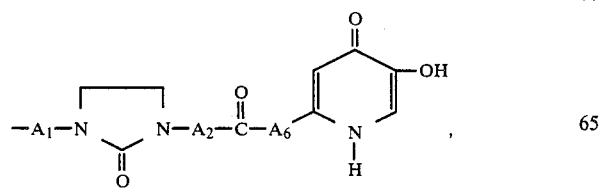

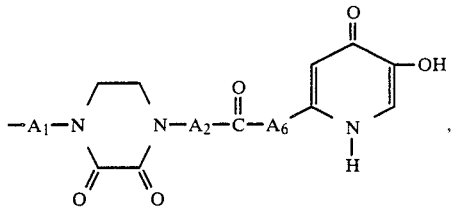

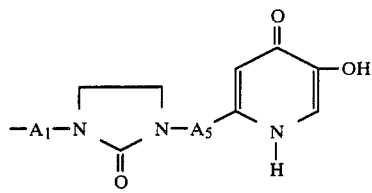

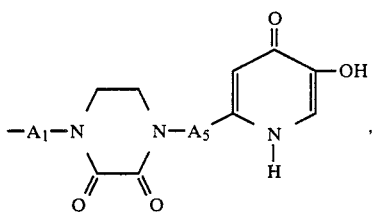

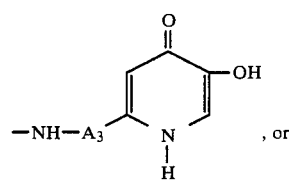, or

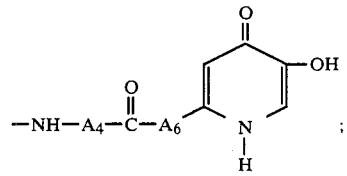;

$R_1$ is an acyl group derived from a carboxylic acid; $R_2$ and $R_3$ are the same or different and each is hydrogen, alkyl, alkenyl, alkynyl, cycloalkyl, phenyl, substituted phenyl or a 4, 5, 6 or 7- membered heterocycle or one of $R_2$ and $R_3$ is hydrogen and the other is azido, halomethyl, dihalomethyl, trihalomethyl, alkoxycarbonyl, 2-phenylethyenyl, 2-phenylethynyl, carboxyl, —CH$_2$X$_1$, —S—X$_2$, —O—X$_2$,

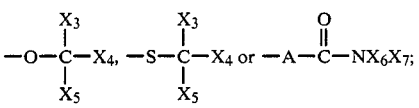

$X_1$ is azido, amino, hydroxy, carboxyl, alkoxycarbonyl, alkanoylamino, phenylcarbonylamino, (substituted pheynyl) carbonylamino, alkylsulfonyl-oxy, phenylsulfonyloxy, (substituted phenyl)-sulfonyloxy, phenyl, substituted phenyl, cyano,

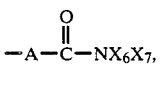

—S—X$_2$, or —O—X$_2$;

X₂ is alkyl, substituted alkyl, phenyl, substituted phenyl, phenylalkyl, (substituted phenyl) alkyl, alkanoyl, phenylalkanoyl, (substituted phenyl) alkanoyl, phenylcarbonyl, (substituted phenyl) carbonyl, or heteroarylcarbonyl;

one of X₃ and X₄ is hydrogen and the other is hydrogen or alkyl, or X₃ and X₄ when taken togehter with the carbon atom to which they are attached form a cycloalkyl group;

X₅ is formyl, alkanoyl, phenylcarbonyl, (substittuted phenyl) carbonyl, phenylalkylcarbonyl, (substituted phenyl)alkylcarbonyl, carboxyl, alkoxycarbonyl, aminocarbonyl, (substituted amono) carbonyl, or cyano;

X₆ and X₇ are the same or different and each is hydrogen, alkyl, phenyl or substituted phenyl, or X₆ is hydrogen and X₇ is amino, substituted amino, alkanoylamino or alkoxy, or X₆ and X₇ when taken together with the nitrogen atom to which they are attached form a 4, 5, 6 or 7-membered heterocycle;

A is —CH=CH—, —(CH₂)ₘ—, —(CH₂)ₘ—O—, —(CH₂)ₘ—NH—or —CH₂—S—CH₂—;

m is 0, 1 or 2;

A₁ is a single bond, $$-NH-\overset{O}{\overset{\|}{C}}-, \quad -NH- \quad or \quad -NH-NH-\overset{O}{\overset{\|}{C}}-;$$

A₂ is a single bond, —NH—, —CH₂—CH₂—NH—, or $$-\overset{O}{\overset{\|}{C}}-NH-NH-;$$

A₃ is —(CH₂)ₚ—, $$-NH-\overset{O}{\overset{\|}{C}}-NH-, \quad -NH-\overset{O}{\overset{\|}{C}}-NH-CH_2-,$$

—NH—CH₂—, —O—CH₂—, $$-CH_2-\overset{O}{\overset{\|}{C}}-NH-, \quad or \quad -CH_2-\overset{O}{\overset{\|}{C}}-NH-CH_2-;$$

A₄ is —NH—, —(CH₂)ₚ—, —(CH₂)ᵧ—NH—, $$-NH-\overset{O}{\overset{\|}{C}}-NH-NH-, \quad -\overset{O}{\overset{\|}{C}}-NH-NH-, \quad or \quad -\overset{CH_2X}{\overset{|}{N}}-;$$

A₅ is a single bond, —CH₂—, —NH—CH₂—, —N=CH—, or $$-\overset{O}{\overset{\|}{C}}-NH-(CH_2)_q-;$$

A₆ is a single bond, —CH=CH— or —(CH₂)ₜ—;
p is 0 or 1;
y is 2, 3 or 4;
q is 0 or 1;
t is 1, 2, 3 or 4; and
X is hydrogen, carboxyl or carbamoyl;
wherein the term "substituted alkyl" refers to alkyl groups substituted with azio, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "substituted phenyl" refers to a phenyl group substituted with 1, 2 or 3 amino, halogen, hydroxyl, trifluoromethyl, alkyl of 1 or 4 carbon atoms, alkoxy of 1 to 4 carbon atoms, alkanoyloxy, aminocarbonyl, or carboxy groups;

the term "substituted amino" refers to a group having the formula —NX₈X₉ wherein X₈ is hydrogen, alkyl, phenyl, substituted phenyl, phenylalkyl or (substituted phenyl)alkyl, and X₉ is alkyl, phenyl, substituted phenyl, phenylalkyl, (substituted phenyl) alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imdazolyl, thiazolyl, thiadiazolyl, pyrimidinyl, oxazolyl, triazinyl, teterazol, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4,5,6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, teterazolyl, azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluorometehyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atom, groups.

2. A compound in accordance with claim 1 wherein R is

[chemical structure]

3. A compound in accordance with claim 1 wherein R is

[chemical structure]

4. A compound in accordance with claim 1 wherein R is

5. A compound in accordance with claim 1 wherein R is

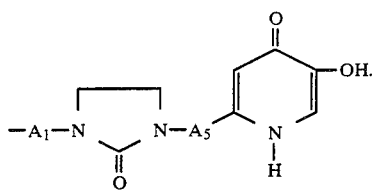

6. A compound in accordance with claim 1 wherein R is

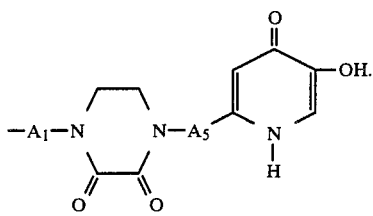

7. A compound in accordance with claim 1 wherein R is

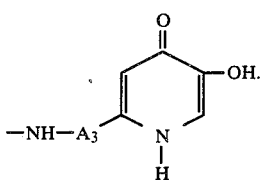

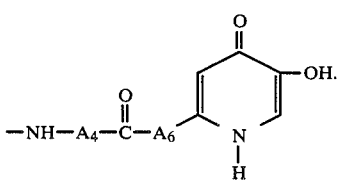

8. A compound in accordance with claim 2 wherein $A_1$ is a single bond.

9. A compound in accordance with claim 2 wherein $A_2$ is —NH—.

10. A compound in accordance with claim 2 wherein $A_6$ is a single bond.

11. A compound in accordance with claim 1 wherein $R_1$ is

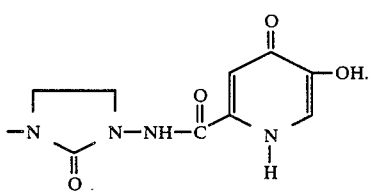

12. A compound in accordance with claim 1 wherein $R_2$ and $R_3$ are each hydrogen.

13. A compound in accordance with claim 1 wherein $R_1$ is

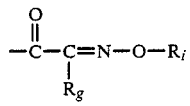

and $R_g$ is 2-amino-4thiazolyl and $R_i$ is methyl, ethyl, carboxymethyl, 1-carboxy-1-methylethyl, 1-carboxy-1-ethyl, or CH$_2$—(CH$_2$)$_s$—C—COOH, wherein s is 1, 2 or 3.

14. A compound in accordance with claim 1 wherein $R_1$ is

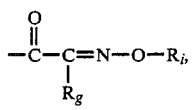

$R_g$ is 2-amino-4-thiazolyl and $R_i$ is carboxymethyl, 1-carboxy-1-methylethyl, 1-carboxy-1-ethyl, or

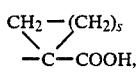

wherein is 1, 2 or 3.

15. A compound in accordance with claim 2 wherein $R_1$ is

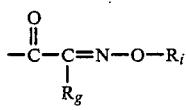

and $R_g$ is 2-amino-4thiazolyl and $R_i$ is methyl, ethyl, carboxymethyl, 1-carboxy-1-methylethyl, 1-carboxy-1-ethyl or

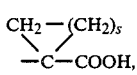

wherein s is 1, 2 or 3.

16. A compound in accordance with claim 2 wherein $R_1$ is

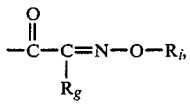

$R_g$ is 2-amino-4-thiazolyl and $R_i$ is carboxymethyl, 1-carboxy-1-methylethyl, 1-carboxy-1-ethyl or

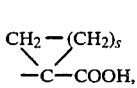

wherein s is 1, 2 or 3.

17. A compound in accordance with claim 11 wherein $R_1$ is

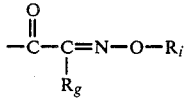

and $R_g$ is 2-amino-4thiazolyl and $R_i$ is methyl, ethyl, carboxymethyl, 1-carboxy-1-methylethyl, 1-carboxy-1-ethyl or

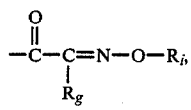

wherein s is 1, 2 or 3.

18. A compound in accordance with claim 11 wherein $R_1$ is

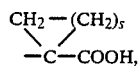

$R_g$ is 2-amino-4-thiazolyl and $R_i$ is carboxymethyl or 1-carboxy-1-methylethyl.

19. A compound in accordance with claim 11 wherein $R_2$ and $R_3$ are each hydrogen.

20. The compound in accordance with claim 1, [3-S(Z)]-2-[[[1-(2-amino-4-thiazolyl)-2-[[1-[[[[3-[[(1,4-dihydro-5-hydroxy-4-oxo-2-pyridinyl)carbonxyl-[amino[-2-oxo-1-imidazolidinyl]sulfonyl]amino]carbonyl]-amino-]-2-oxo-3-azetidinyl[amino[-2-oxoethylidene-]amino]oxy]-2-methylpropanoic acid, or a pharmaceutically acceptable salt thereof.

21. The compound in accordance with claim 1, [3S(Z)]-2-[[[1-(2-amino-4-thiazolyl)-2-[[1-[[[[2[(1,4-dihydro-5-hydroxy-4-oxo-2-pyridinyl)carbonyl]hydrazino]sulfonyl]amino]carbonyl]-2-oxo- 3-azetidinyl]amino]-2-oxoethylidene]amino]oxy]-2-methylpropanoic acid, or a pharmaceutically acceptable salt thereof.

22. The compound in accordance with claim 1, [3S(Z)]-2-[[[1-(2-amino-4-thiazolyl)-2-[[1[[[[3-[[(1,4-dihydro-5-hydroxy-4-oxo-2-pyridinyl)carbonyl]amino]-2-oxo-1-imidizolidinyl]sulfonyl]amino]carbonyl]-2-oxo-3-azetidinyl]amino]2-oxoethylidene]amino]oxy]-2-acetic acid, or a pharmaceutically acceptable salt thereof.

23. The compound in accordance with claim 1, [3S(Z)]-2-[[[1-(2-amino-4-thiazolyl)-2-[[1[[[[(1,4-dihydro-5-hydroxy-4-oxo-2-pyridinyl)methyl]amino]sulfonyl]amino]carbonyl]-2-oxo-3azetidi nyl]amino]-2-oxoethylidene]amino]oxy]-2methylpropanoic acid, or a pharmaceutically acceptable salt thereof.

24. The compound in accordance with claim 1, [3S(Z)]-2-[[[1-(2-amino-4-thiazolyl)-2-[[1-[[[[2[[2--[(1,4-dihydro-5-hydroxy-4-oxo-2-pyridinyl)carbonyl]-hydrazino]carbonyl]hydrazino]sulfonyl]amino]carbonyl]-2-oxo-3-azetidinyl]amino]2-oxoethylidene]amino]oxy]-2-methylpropanoic acid, or a pharmaceutically acceptable salt thereof.

25. The compound in accordance with claim 1, [3S-3α(Z),4β]-2-[[[1-(2-amino-4-thiazolyl)-2[[1-[[[2-[(1,4-dihydro-5-hydroxy-4-oxo-2-pyridinyl)carbonyl]hydrazino]sulfonyl]amino]carbonyl-4-methyl2-oxo-3-azetidinyl]amino]-2-oxoethylidene-amino]oxy]2-methylpropionic acid, or a pharmaceutically acceptable salt thereof.

26. The compound in accordance with claim 1, [3-S(Z)]-1-[[[1-(2-amino-4-thiazolyl)-2-[1-[[[[3[[(1,4-dihydro-5-hydroxy-4-oxo-2-pyridinyl)carbonyl]amino]-2-oxo-1-imidazolidinyl]sulfonyl]amino]carbonyl]2-oxo-3-azetidinyl]amino]-2-oxoethylidene]amino]oxy]cyclopentanecarboxylic acid, or a pharmaceutically acceptable salt thereof.

* * * * *